(12) United States Patent
Niazi

(10) Patent No.: US 11,779,637 B2
(45) Date of Patent: Oct. 10, 2023

(54) TARGETED NEOEPITOPE VECTORS AND METHODS THEREFOR

(71) Applicant: NANTCELL, INC., Culver City, CA (US)

(72) Inventor: Kayvan Niazi, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

(21) Appl. No.: 16/606,993

(22) PCT Filed: Apr. 23, 2018

(86) PCT No.: PCT/US2018/028889
§ 371 (c)(1),
(2) Date: Oct. 21, 2019

(87) PCT Pub. No.: WO2018/200389
PCT Pub. Date: Nov. 1, 2018

(65) Prior Publication Data
US 2020/0054730 A1 Feb. 20, 2020

Related U.S. Application Data

(60) Provisional application No. 62/489,102, filed on Apr. 24, 2017.

(51) Int. Cl.
| | | |
|---|---|---|
| *A61K 39/00* | (2006.01) | |
| *A61K 39/39* | (2006.01) | |
| *A61P 35/00* | (2006.01) | |
| *C07K 14/705* | (2006.01) | |
| *C12N 15/70* | (2006.01) | |
| *C12N 15/861* | (2006.01) | |
| *C12N 15/81* | (2006.01) | |

(52) U.S. Cl.
CPC ...... *A61K 39/001102* (2018.08); *A61K 39/39* (2013.01); *A61P 35/00* (2018.01); *C07K 14/70596* (2013.01); *C12N 15/70* (2013.01); *C12N 15/81* (2013.01); *C12N 15/861* (2013.01); *A61K 2039/51* (2013.01); *A61K 2039/523* (2013.01); *A61K 2039/5256* (2013.01); *A61K 2039/53* (2013.01); *A61K 2039/585* (2013.01); *C12N 2710/10011* (2013.01); *C12N 2710/10021* (2013.01); *C12N 2710/10043* (2013.01); *C12N 2799/022* (2013.01)

(58) Field of Classification Search
None
See application file for complete search history.

(56) References Cited

U.S. PATENT DOCUMENTS

| | | | |
|---|---|---|---|
| 7,179,797 B2 | 2/2007 | McNeel | |
| 7,473,532 B2 | 1/2009 | Darfler et al. | |
| 7,758,891 B2 | 7/2010 | Desai et al. | |
| 7,771,751 B2 | 8/2010 | Desai et al. | |
| 7,780,984 B2 | 8/2010 | Desai et al. | |
| 7,981,445 B2 | 7/2011 | De et al. | |
| 8,034,375 B2 | 10/2011 | Desai et al. | |
| 8,445,268 B2 | 5/2013 | Lee et al. | |
| 2005/0095648 A1 | 5/2005 | Geysen et al. | |
| 2007/0123487 A1 | 5/2007 | McNeel | |
| 2010/0196411 A1 | 8/2010 | Duke et al. | |
| 2011/0071214 A1 | 3/2011 | Allen | |
| 2011/0293637 A1 | 12/2011 | Hacohen et al. | |
| 2012/0059670 A1 | 3/2012 | Sanborn et al. | |
| 2012/0066001 A1 | 3/2012 | Sanborn et al. | |
| 2012/0107347 A1 | 5/2012 | Hodge et al. | |
| 2014/0178438 A1 | 6/2014 | Sahin et al. | |
| 2014/0363465 A1 | 12/2014 | Letvin et al. | |
| 2016/0058853 A1 | 3/2016 | Sahin et al. | |
| 2016/0339090 A1 | 11/2016 | Hacohen et al. | |
| 2017/0224794 A1 | 8/2017 | Franzusoff et al. | |
| 2017/0246276 A1 | 8/2017 | Palena et al. | |
| 2017/0312351 A1 | 11/2017 | Niazi et al. | |

FOREIGN PATENT DOCUMENTS

| | | |
|---|---|---|
| CA | 3 018 741 A1 | 12/2017 |
| CN | 109563521 A | 4/2019 |
| CN | 110662841 A | 1/2020 |
| JP | 2016-501870 A | 1/2016 |
| JP | 2019-513021 A | 5/2019 |
| KR | 10-2016-0101073 A | 8/2016 |
| KR | 10-2018-0117227 A | 10/2018 |
| KR | 10-2019-0137165 A | 12/2019 |
| TW | 201742923 A | 12/2017 |
| WO | 00/78806 A1 | 12/2000 |
| WO | 2009/006479 A3 | 3/2009 |
| WO | 2011/139345 A2 | 11/2011 |

(Continued)

OTHER PUBLICATIONS

Kreiter et al., Nature, Apr. 2015, 520(7549):692-696. (Year: 2015).*
Kreiter et al., Journal of Immunology, 2008, 180:309-318. (Year: 2008).*
Niazi et al., Immunology, 2007,122, 522-531. (Year: 2007).*
Van Allen et al., Science, 2015, 350(6257):207-211. (Year: 2015).*
Sinah et al., BMC Biotechnology, 2012, 12:54. (Year: 2012).*
Notice of Allowance received for U.S. Appl. No. 15/468,046 dated Aug. 18, 2021, 14 pages.

(Continued)

*Primary Examiner* — Nicole Kinsey White

(74) *Attorney, Agent, or Firm* — Martin Fessenmaier; Umberg Zipser LLP

(57) ABSTRACT

Systems and methods are presented that allow for selection of tumor neoepitopes that are then used to generate recombinant nucleic acids that encode one or more polytopes that are optimized for proper trafficking and processing. In preferred methods, the polytopes are encoded in a plasmid and/or a viral expression system for use as a therapeutic agent.

10 Claims, 11 Drawing Sheets

Specification includes a Sequence Listing.

(56) References Cited

FOREIGN PATENT DOCUMENTS

| | | |
|---|---|---|
| WO | 2012/159754 A2 | 11/2012 |
| WO | 2013/062505 A1 | 5/2013 |
| WO | 2014/031178 A1 | 2/2014 |
| WO | 2014/082729 A1 | 6/2014 |
| WO | 2014/168874 A2 | 10/2014 |
| WO | 2015/095811 A2 | 6/2015 |
| WO | 2016/061087 A1 | 4/2016 |
| WO | 2016/172722 A1 | 10/2016 |
| WO | 2016/187508 A2 | 10/2016 |
| WO | 2016/191545 A1 | 12/2016 |
| WO | 2016/207859 A1 | 12/2016 |
| WO | 2017/035392 A1 | 3/2017 |
| WO | 2017/066256 A2 | 4/2017 |
| WO | 2017/222619 A2 | 12/2017 |
| WO | 2018/094309 A2 | 5/2018 |
| WO | 2018/200389 A1 | 11/2018 |
| WO | 2017/222619 A3 | 3/2019 |

OTHER PUBLICATIONS

Non Final Office Action received for U.S. Appl. No. 16/874, 104 dated Aug. 19, 2021, 51 pages.

Non Final Office Action received for U.S. Appl. No. 16/874,104 dated Dec. 2, 2020, 116 pages.

Sorber (NIH Medical Research Scholars Program, 2014-2015 Scholars and Abstracts, pp. 1-48 Abstract p. 39). (Year: 2014).

Xu et al., "Efficacy and mechanism-of-action of a novel superagonist interleukin-15: interleukin-15 receptor αSu/Fc fusion complex in syngeneic murine models of multiple myeloma", Cancer Research, 2013, vol. 73, No. 10, pp. 3075-3086.

Amalfitano et al., "Production and characterization of improved adenovirus vectors with the E1, E2b, and E3 genes deleted", Journal of Virology, 1998, vol. 72, No. 2, pp. 926-933.

Habib-Agahi., "Co-stimulation with 4-1BB ligand allows extended T-cell proliferation, synergizes with CD80/CD86 and can reactivate anergic T cells", International Immunology, 2007, vol. 19, No. 2, pp. 1383-1394.

Andarini et al., "Adenovirus vector-mediated in vivo gene transfer of OX40 ligand to tumor cells enhances antitumor Immunity of tumor-bearing hosts", Cancer Research, 2004, vol. 64, 3281-3287.

Hodi et al., "Improved survival with ipilimumab in patients with metastatic melanoma", The New England Journal of Medicine, 2010, vol. 363, No. 8, pp. 711-723.

Notice of Reasons for Refusal received for Japanese Patent Application Serial No. 2019557605 dated Feb. 2, 2021, 7 pages (Including English Translation).

Final Office Action received for U.S. Appl. No. 16/874,104 dated Apr. 15, 2021, 109 pages.

Noting of loss of rights pursuant to Rule 112(1) EPC received for European Patent Application Serial No. 17815840.8 dated Feb. 18, 2021, 2 pages.

Notice of Allowance received for U.S. Appl. No. 15/468,046 dated Sep. 14, 2021, 33 pages.

Boyer et al., "Vaccination of Seronegative Volunteers with a Human Immunodeficiency Virus Type 1 env/rev DNA Vaccine Induces Antigen-Specific Proliferation and Lymphocyte Production of β-Chemokines", The Journal of Infectious Diseases, Feb. 2000, vol. 181, pp. 476-483.

Fejer et al., "Adenovirus-Triggered Innate Signalling Pathways", European Journal of Microbiology and Immunology, 2011, vol. 1, No. 4, pp. 279-288.

International Search Report and Written Opinion received for PCT Application Serial No. PCT/US2018028889 dated Aug. 14, 2018, 22 pages.

Mincheff et al., "Naked DNA and Adenoviral Immunizations for Immunotherapy of Prostate Cancer: A Phase I/II Clinical Trial", European Urology, 2000, vol. 38, 2 pages.

International Preliminary Report received in PCT Application Serial No. PCT/US2018/028889, dated Aug. 28, 2019, 9 pages.

Office Action received for Canadian patent Application Serial No. 3061240 dated Dec. 9, 2020, 6 pages.

Notice of Reasons for Refusal received for Japanese Patent Application Serial No. 2019557605, dated Oct. 22, 2021, 4 Pages. (Including English Translation).

Office Action received for Canadian patent Application Serial No. 3061240 dated Oct. 12, 2021, 3 pages.

Office Action received for Taiwanese Patent Application Serial No. 106110045 dated Sep. 14, 2020, 16 pages (Including English Translation).

Extended European search report received for European Patent Application Serial No. 18791753.9 dated Jan. 28, 2021, 11 pages.

Office Action received for Taiwanese Patent Application Serial No. 106110045 dated Jan. 4, 2021, 4 pages (Including English Translation).

Notice of acceptance received for Australian Patent Application Serial No. 2018258119 dated Mar. 18, 2021, 3 pages.

Non Final Office Action received for U.S. Appl. No. 15/468,046 dated Feb. 4, 2021, 73 pages.

Final Rejection received for U.S. Appl. No. 15/468,046 dated Aug. 31, 2020, 40 pages.

Extended European search report received for European Patent Application Serial No. 17815840.8 dated Jun. 25, 2020, 14 pages.

Communication pursuant to Rules 70(2) and 70a(2) EPC received for European Patent Application Serial No. 17815840.8 dated Jul. 14, 2020, 1 page.

Decision of Refusal received for Japanese Patent Application Serial No. 2018550347 dated Aug. 25, 2020, 2 pages (Including English Translation).

Notice of Final Rejection received for Korean Patent Application Serial No. 10-2018-7030362 dated Jul. 6, 2020, 2 pages (Including English Translation).

Notice of Allowance received for U.S. Appl. No. 15/468,046 dated Sep. 29, 2021, 43 pages.

Notice of Allowance received for U.S. Appl. No. 15/468,046 dated Jul. 23, 2021, 56 pages.

Notice of Final Rejection received for Korean Patent Application Serial No. 10-2019-7034742 dated Jul. 8, 2021, 8 pages (Including English Translation).

Notification of Reason for Refusal received for Korean Patent Application Serial No. 10-2019-7034742 dated Jan. 5, 2021, 13 pages (Including English Translation).

Grant of Patent received for Korean Patent Application Serial No. KR10-2019-7034742 dated Sep. 7, 2021, 2 pages (Including English Translation).

Briken et al., "Intracellular trafficking pathway of newly synthesized CD1b molecules", The EMBO Journal, 2002, vol. 21, No. 4, pp. 825-834.

International Search Report and Written Opinion received for PCT Application Serial No. PCT/US2017/023894 dated Feb. 18, 2019, 13 pages.

Fukuda et al., "Cloning of cDNAs Encoding Human Lysosomal Membrane Glycoproteins, h-lamp-1 and h-lamp-2", The Journal of Biological Chemistry, Dec. 15, 1988, vol. 263, No. 35, pp. 18920-18928.

Fritsch et al., "HLA-binding properties of tumor neoepitopes in humans", Cancer Immunology Research, Jun. 2014, vol. 2, No. 6, pp. 522-529.

Zhang et al., "An adenoviral vector cancer vaccine that delivers a tumor-associated antigen/CD40-ligand fusion protein to dendritic cells", PNAS, Dec. 9, 2003, vol. 1 00, No. 25, p. 1-25.

Sloan et al., "MHC class I and class II presentation of tumor antigen in retrovirally and adenovirally transduced dendritic cells", Cancer Gene Therapy, 2002, vol. 9, No. 11, pp. 946-950.

International Preliminary Report on Patentability received for PCT Application Serial No. PCT/US2017/023894 dated Feb. 26, 2019, 08 pages.

International Search Report and Written Opinion received for Singapore Application Serial No. 11201807770R dated Jan. 22, 2020, 13 pages.

Mateo et al., "An HLA-A2 polyepitope vaccine for melanoma immunotherapy", The Journal of Immunology, Oct. 1, 1999, vol. 163, No. 7, pp. 4058-4063.

(56) References Cited

OTHER PUBLICATIONS

Cong et al., "Cytoskeletal protein PSTPIP1 directs the PEST-type protein tyrosine phosphatase to the c-Abl kinase to mediate Abl dephosphorylation", Molecular Cell, Dec. 2000, vol. 6, pp. 1413-1423.
Partial European Search Report received for European Patent Application Serial No. 17815840.8 dated Mar. 2, 2020, 16 pages.
Notice of Grounds for Rejection received for Korean Patent Application Serial No. 1020187030362 dated Feb. 27, 2020, 14 pages (Including English Translation).
Jones et al., "A Subset of Latency-Reversing Agents Expose HIV-Infected Resting CD4+ T-Cells to Recognition by Cytotoxic T-Lymphocytes", PLOS Pathogens, 2016, vol. 12, No. 4, e1005545, pp. 1-25.
Mincheff et al., "Naked DNA and Adenoviral Immunizations for Immunotherapy of Prostate Cancer: A Phase I/II Clinical Trial", European Urology, 2000, vol. 38, pp. 208-217.
Chu et al., "Indigenous enteric eosinophils control DCs to initiate a primary Th2 immune response in vivo" The Journal of Experimental Medicine 2014, vol. 211, pp. 1657-1672.
Kouchakzadeh Hasan et al., "Efficient Delivery of Therapeutic Agents by Using Targeted Albumin Nanoparticles", Elsevier Inc, 2015, vol. 98, pp. 121-143.
Feltquate et al., "Different T helper cell types and antibody isotypes generated by saline and gene gun DNA Immunization", The journal of Immunology, 1997, vol. 158, No. 5, 4 pages.
Non Final Rejection received for U.S. Appl. No. 15/468,046 dated Dec. 31, 2018, 77 pages.
Final Rejection received for U.S. Appl. No. 15/468,046 dated Jul. 11, 2019, 53 pages.
Non Final Rejection received for U.S. Appl. No. 15/468,046 dated Apr. 17, 2020, 42 pages.
Charoentong et al., "Bioinformatics for cancer immunology and immunotherapy", Cancer Immunol. Immunother., 2012, vol. 61, pp. 1885-1903.
Brennick et al., "Neoepitopes as cancer immunotherapytargets: key challenges and opportunities", Immunotherapy, 2017, vol. 9, No. 4, pp. 361-371.
McCluskie et al., "Route and Method of Delivery of DNA VaccineInfluence Immune Responses in Mice and NonHumanPrimates", Molecular Medicine, 1999, vol. 5, pp. 287-300.
Pierre et al., "Genetic adjuvants for DNA vaccines", Vaccine, 2001, vol. 19, pp. 2647-2656.
Niazi et al., "Activation of human CD4+ T cells by targeting MHC class II epitopes to endosomal compartments using human CD1 tail sequences", Immunology, 2007, vol. 122, No. 4, pp. 522-531.
Kreiter et al., "Increased Antigen Presentation Efficiency by Coupling Antigens to MHC Class I Trafficking Signals", The Journal of Immunology, 2008, vol. 180, pp. 309-318.
Kim et al., "Engineering Human Tumor-specific CytotoxicT Cells to function in a Hypoxic Environment", Molecular Therapy, 2008, vol. 16 No. 3, pp. 599-606.
First Examiner's Report received for Canadian Patent Application Serial No. 3018741 dated Oct. 17, 2019, 4 pages.
Li et al., "Mapping short DNA sequencing reads and calling variants using mapping quality scores", Genome Research, vol. 18, No. 11, pp. 1851-1858.
Goya et al., SNVMix: predicting single nucleotide variants from next-generation sequencing of tumors, Bioinformatics, vol. 26, No. 6, pp. 730-736.
Sykulev et al., "Evidence that a Single Peptide-MHC Complex on a Target Cell Can Elicit a Cytolytic T Cell Response", Immunity, Jun. 1, 1996, vol. 4, No. 6, pp. 565-571.
Lawrence et al., "Discovery and saturation analysis of cancer genes across 21 tumour types", Nature, Jan. 23, 2014, vol. 505, No. 7484, pp. 495-501.
Reimand et al., "Systematic analysis of somatic mutations in phosphorylation signaling predicts novel cancer drivers", Molecular Systems Biology, 2013, vol. 9, No. 637, p. 1-18.
Dees et al., "MuSiC: Identifying mutational significance in cancer genomes", Genome Research, Jul. 3, 2012, vol. 22, No. 8, pp. 1589-1598.
Tamborero et al., "OncodriveCLUST: exploiting the positional clustering of somatic mutations to identify cancer genes", Bioinformatics, 2013, vol. 29, No. 18, pp. 2238-2244.
Gonzalez-Perez et al., "Functional impact bias reveals cancer drivers", Nucleic Acids Research, Aug. 16, 2012, vol. 40, No. 21, p. 1-10.
Mularoni et al., "OncodriveFML: a general framework to identify coding and non-coding regions with cancer driver mutations", Genome Biology, 2016, vol. 17, No. 1, p. 1-13.
Davoli et al., "Cumulative Haploinsufficiency and Triplosensitivity Drive Aneuploidy Patterns and Shape the Cancer Genome", Cell, Nov. 7, 2013, vol. 155, No. 4, pp. 948-962.
Schroeder et al., "OncodriveROLE classifies cancer driver genes in loss of function and activating mode of action", Bioinformatics, 2014, vol. 30, No. 17, pp. i549-i555.
Lundegaard et al., "NetMHC-3.0: accurate web accessible predictions of human, mouse and monkey MHC class I affinities for peptides of length 8-11", Nucleic Acids Research, May 7, 2008, vol. 36, Web Server issue, pp. W509-W512.
Zhang et al., "Machine learning competition in immunology—Prediction of HLA class I binding peptides", Journal of Immunological Methods, 2011, vol. 374, No. (1-2), p. 1-4.
Amalfitano et al., "Production and Characterization of Improved Adenovirus Vectors with the E1, E2b, and E3 Genes Deleted", Journal of Virology, Feb. 1998, vol. 72, No. 2, pp. 926-933.
Heijne G.V, "A new method for predicting signal sequence cleavage sites", Nucleic Acids Research, Jun. 11, 1986, vol. 14, No. 11, pp. 4683-4690.
Kall et al., "A Combined Transmembrane Topology and Signal Peptide Prediction Method", Journal of Molecular Biology, 2004, vol. 338, No. 5, pp. 1027-1036.
Kouchakzadeh et al., "Efficient Delivery of Therapeutic Agents by Using Targeted Albumin Nanoparticles", Advances in Protein Chemistry and Structural Biology, 2015, vol. 98, 23 pages.
First Office Action received for Japanese Patent Application Serial No. 2018550347 dated Jan. 21, 2020, 07 pages (Including English Translation).
First Office Action received for korean Patent Application Serial No. 10-2018-7030362 dated Aug. 30, 2019, 11 pages (Including English Translation).
Examination Report No. 1 received for Australian Patent Application Serial No. 2018258119 dated Mar. 1, 2021, 4 pages.
Notification of Grant received for Chinese Patent Application Serial No. 201880027376.8 dated May 31, 2023, 4 pages. (Including English Translation).
Office Action received for Israel Patent Application Serial No. 270132 dated May 31, 2023, 4 pages. (Including English Translation).
Second Office Action received for Chinese Patent Application Serial No. 201880027376.8 dated Mar. 16, 2023, 9 pages. (Including English Translation).

\* cited by examiner

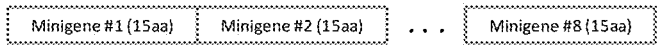
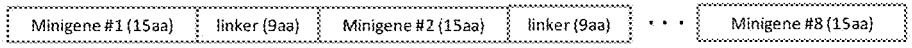
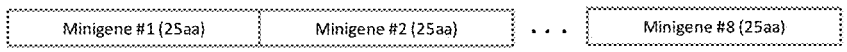
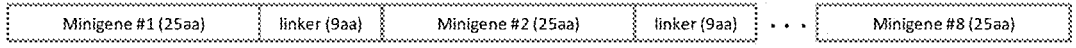
Figure 1
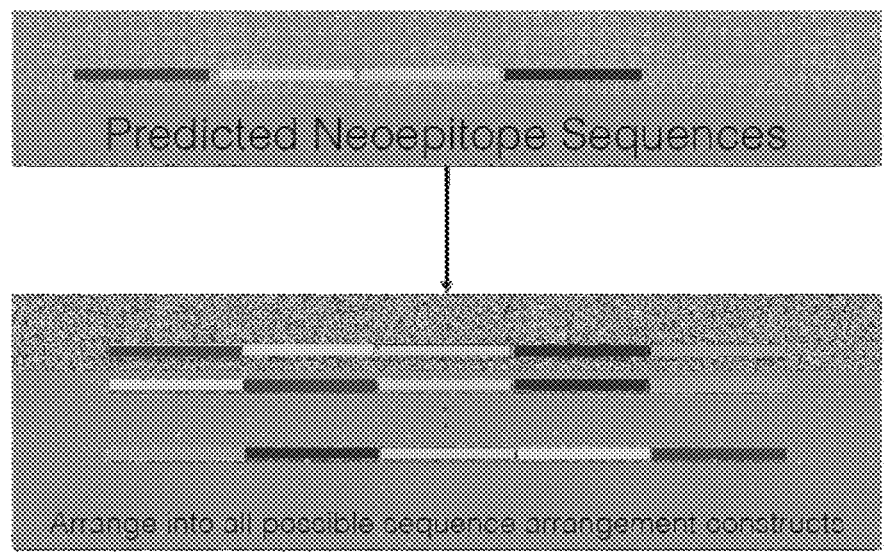
Figure 2

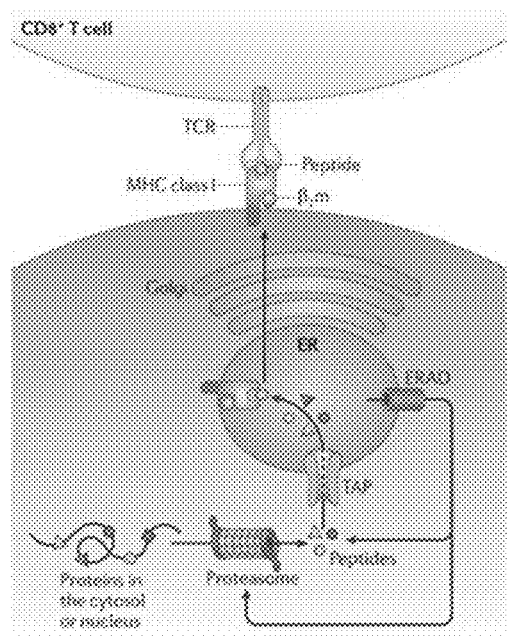
Prior Art Figure 3
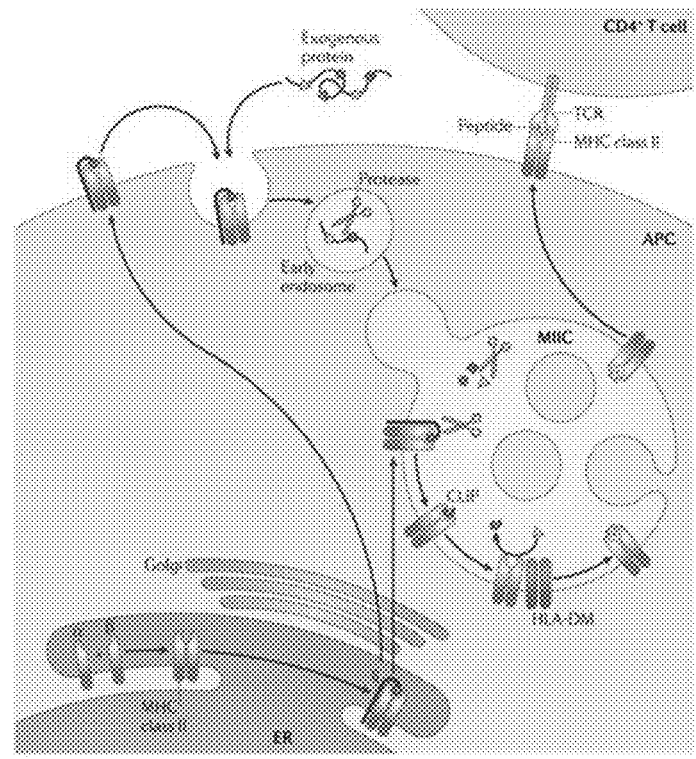
Prior Art Figure 4

MDKITQYEKSLYYCSFLEALVRDVCIAAAACVDCLDRTNTAQVMVGKCALAYQLYAAAAVVKAY
LPVNESFAFTADLRSNTGGQAAAANILAVSFAPLVQLSKNDNGTPDSVGAAAAQSNYQHITNFE
WCISILVELTRLEGAAAAYYTVFDRDNNRVSFANAVVLAAAAHSGLVTFQAFIDVMSRETTDTD
TADAAAALDLAALEDVSANCLTETLEDKNEGVAAAAVLSFVGQTRVLMINGEEVEETELMGAAA
AEVSGLEQLESIINFEKLTEWTSSNVAAAA*MTEQQWNFAGIEAAASAIQGNVTSIHSLLD*AAAAE
QKLISEEDL (SEQ ID NO.: 4)

Figure 5A

*MQIFVKTLTGKTITLEVEPSDTIENVKAKIQDKEGIPPDQQRLIFAGKQLEDGRTLSDYNIQKESTLHLVLRL*
*RGGR*DKITQYEKSLYYCSFLEALVRDVCIAAAACVDCLDRTNTAQVMVGKCALAYQLYAAAAVV
KAYLPVNESFAFTADLRSNTGGQAAAANILAVSFAPLVQLSKNDNGTPDSVGAAAAQSNYQHIT
NFEWCISILVELTRLEGAAAAYYTVFDRDNNRVSFANAVVLAAAAHSGLVTFQAFIDVMSRETT
DTDTADAAAALDLAALEDVSANCLTETLEDKNEGVAAAAVLSFVGQTRVLMINGEEVEETELMG
AAAAEVSGLEQLESIINFEKLTEWTSSNVAAAA*MTEQQWNFAGIEAAASAIQGNVTSIHSLLD*AA
AAEQKLISEEDL (SEQ ID NO.: 5)

Figure 5B

*MQIFVKTLTGKTITLEVEPSDTIENVKAKIQDKEGIPPDQQRLIFAGKQLEDGRTLSDYNIQKESTLHLVLRL*
*RG*DKITQYEKSLYYCSFLEALVRDVCIAAAACVDCLDRTNTAQVMVGKCALAYQLYAAAAVVKAYLPVNE
SFAFTADLRSNTGGQAAAANILAVSFAPLVQLSKNDNGTPDSVGAAAAQSNYQHITNFEWCISILVELTRL
EGAAAAYYTVFDRDNNRVSFANAVVLAAAAHSGLVTFQAFIDVMSRETTDTDTADAAAALDLAALEDVSA
NCLTETLEDKNEGVAAAAVLSFVGQTRVLMINGEEVEETELMGAAAA*EVSGLEQLESIINFEKLTEWTSSN*
*V*AAAA*MTEQQWNFAGIEAAASAIQGNVTSIHSLLD*AAAAEQKLISEEDL (SEQ ID NO.: 6)

Figure 5C

MLLLPFQLLAVLFPGGNSEDKITQYEKSLYYCSFLEALVRDVCIGPGPGCVDCLDRTNTAQVMVGKCALA
YQLYGPGPGVVKAYLPVNESFAFTADLRSNTGGQGPGPGNILAVSFAPLVQLSKNDNGTPDSVGGPGP
GQSNYQHITNFEWCISILVELTRLEGGPGPGYYTVFDRDNNRVSFANAVVLGPGPGHSGLVTFQAFIDVM
SRETTDTDTADGPGPGLDLAALEDVSANCLTETLEDKNEGVGPGPGVLSFVGQTRVLMINGEEVEETEL
MGGPGPGEVSGLEQLESIINFEKLTEWTSSNVGGPGPG<u>MTEQQWNFAGIEAAASAIQGNVTSIHSLLD</u>*DY*
*KDDDDKGSDYKDHDGDYKDHD*<u>MLIPIAVGGALAGLVLIVLIAYLIG</u>*RKRSHAGYQTI*

(SEQ ID NO.: 10)

Figure 6A

MLLLPFQLLAVLFPGGNSEDKITQYEKSLYYCSFLEALVRDVCIGPGPGCVDCLDRTNTAQVMVGKCALAYQLYGPG
PGVVKAYLPVNESFAFTADLRSNTGGQGPGPGNILAVSFAPLVQLSKNDNGTPDSVGGPGPGQSNYQHITNFEWCIS
ILVELTRLEGGPGPGYYTVFDRDNNRVSFANAVVLGPGPGHSGLVTFQAFIDVMSRETTDTDTADGPGPGLDLAALE
DVSANCLTETLEDKNEGVGPGPGVLSFVGQTRVLMINGEEVEETELMGGPGPGEVSGLEQLESIINFEKLTEWTSSN
VGGPGPG<u>MTEQQWNFAGIEAAASAIQGNVTSIHSLLD</u>*DYKDDDDKGSDYKDHDGDYKDHD*<u>MLIPIAVGGALAGLVL
IVLIAYLIG</u>*RKRCFC*

(SEQ ID NO.: 11)

Figure 6B

MLLLPFQLLAVLFPGGNSEDKITQYEKSLYYCSFLEALVRDVCIGPGPGCVDCLDRTNTAQVMVGKCALA
YQLYGPGPGVVKAYLPVNESFAFTADLRSNTGGQGPGPGNILAVSFAPLVQLSKNDNGTPDSVGGPGP
GQSNYQHITNFEWCISILVELTRLEGGPGPGYYTVFDRDNNRVSFANAVVLGPGPGHSGLVTFQAFIDVM
SRETTDTDTADGPGPGLDLAALEDVSANCLTETLEDKNEGVGPGPGVLSFVGQTRVLMINGEEVEETEL
MGGPGPGEVSGLEQLESIINFEKLTEWTSSNVGGPGPG<u>MTEQQWNFAGIEAAASAIQGNVTSIHSLLD</u>*DY*
*KDDDDKGSDYKDHDGDYKDHD*<u>MLIPIAVGGALAGLVLIVLIAYLIG</u>*KKHCSYQDIL*

(SEQ ID NO.: 12)

Figure 6C

MLLLPFQLLAVLFPGGNSEALQAYHLDPQCWGVNVQPYSGSPANVAVYTALVEPHGRIMGLD
LPDGGHLTGPGPGDTDEAEDPEKMLANFESGKHKYRQTAMFTATMPPAVERLARSYLRRPAV
VYGPGPGRRYLLQNTALEVFMANRTSVMFNFPEQATVKKVVYSLPRVGVGTSYGLPQAGPGP
GKIEPDMMSMEHSFETASHDGEAGPSPEVLQGPGPGKVLMASTSYLPSQVTEMFNQGRAFA
AVRLPFCGHKNICSLTTIQKIPRLLVGPGPGMPAAELALSAFLVLVFLWVHSLRRLLECFYVSVF
SNAAIHVVQYCFGLVYYGPGPGLLELLHCPLGHCHLCSEPMFTFVYPTIFPLRETPMAGLHQRR
TSIGFVAYCGPGPGAHFRLVSKEKMPWDSIKLTFEATGPRHMSFYVRTHKGSTLSQWSLGNGI
PVGPGPGGRTQQMLIPAWQQVTPMAPAAATLTFEGMAGSQRLGDWGKMIPHSNHYNSVGP
GPGELQLVQLEGGGGSGTYRVGNAQPSLADCLDAGDLAQRLREHGAEVPTEPKEGPGPGEL
EKFRKSEEGKQRAAAPSAASSPADVQSLKKAMSSLQNDRDRLLKELKNLGPGPGGKHDRDLLI
GTAKHGLNRTDYYIMNGPQLSFLDAYRNYAQHKRTDTQAPGSGPGPGILEVDKSGPITLLVQG
HMEGEVWGLSTHPYLPICATVSDDKTLRIWDLSPSGPGPGMLTARLLLPRLLCLQGRTTSYST
AAVLPNPIPNPEICYNKLFINNEWHDAVGPGPG<u>EVSGLEQLESIINFEKLTEWTSSNV</u>GGPGPG
<u>MTEQQWNFAGIEAAASAIQGNVTSIHSLLD</u>*DYKDDDDKGSDYKDHDGDYKDHD*<u>**MLIPIAVGG
ALAGLVLIVLIAYLIG**RKRSHAGYQTI</u>

(SEQ ID NO.: 16)

Figure 7A

MLLLPFQLLAVLFPGGNSEALQAYHLDPQCWGVNVQPYSGSPANVAVYTALVEPHGRIMGLDLPDGGH
LTGPGPGDTDEAEDPEKMLANFESGKHKYRQTAMFTATMPPAVERLARSYLRRPAVVYGPGPGRRYLL
QNTALEVFMANRTSVMFNFPEQATVKKVVYSLPRVGVGTSYGLPQAGPGPGKIEPDMMSMEHSFETAS
HDGEAGPSPEVLQGPGPGKVLMASTSYLPSQVTEMFNQGRAFAAVRLPFCGHKNICSLTTIQKIPRLLVG
PGPGMPAAELALSAFLVLVFLWVHSLRRLLECFYVSVFSNAAIHVVQYCFGLVYYGPGPGLLELLHCPLG
HCHLCSEPMFTFVYPTIFPLRETPMAGLHQRRTSIGFVAYCGPGPGAHFRLVSKEKMPWDSIKLTFEATG
PRHMSFYVRTHKGSTLSQWSLGNGIPVGPGPGGRTQQMLIPAWQQVTPMAPAAATLTFEGMAGSQRL
GDWGKMIPHSNHYNSVGPGPGELQLVQLEGGGGSGTYRVGNAQPSLADCLDAGDLAQRLREHGAEVP
TEPKEGPGPGELEKFRKSEEGKQRAAAPSAASSPADVQSLKKAMSSLQNDRDRLLKELKNLGPGPGGK
HDRDLLIGTAKHGLNRTDYYIMNGPQLSFLDAYRNYAQHKRTDTQAPGSGPGPGILEVDKSGPITLLVQG
HMEGEVWGLSTHPYLPICATVSDDKTLRIWDLSPSGPGPGMLTARLLLPRLLCLQGRTTSYSTAAVLPNPI
PNPEICYNKLFINNEWHDAVGPGPG<u>EVSGLEQLESIINFEKLTEWTSSNV</u>GGPGPGMTEQQWNFAGIEA
<u>AASAIQGNVTSIHSLLD</u>*DYKDDDDKGSDYKDHDGDYKDHD*<u>MLIPIAVGGALAGLVLIVLIAYLIG*RKRCFC*</u>

Figure 7B          (SEQ ID NO.: 17)

MLLLPFQLLAVLFPGGNSEALQAYHLDPQCWGVNVQPYSGSPANVAVYTALVEPHGRIMGLDLPDGGH
LTGPGPGDTDEAEDPEKMLANFESGKHKYRQTAMFTATMPPAVERLARSYLRRPAVVYGPGPGRRYLL
QNTALEVFMANRTSVMFNFPEQATVKKVVYSLPRVGVGTSYGLPQAGPGPGKIEPDMMSMEHSFETAS
HDGEAGPSPEVLQGPGPGKVLMASTSYLPSQVTEMFNQGRAFAAVRLPFCGHKNICSLTTIQKIPRLLVG
PGPGMPAAELALSAFLVLVFLWVHSLRRLLECFYVSVFSNAAIHVVQYCFGLVYYGPGPGLLELLHCPLG
HCHLCSEPMFTFVYPTIFPLRETPMAGLHQRRTSIGFVAYCGPGPGAHFRLVSKEKMPWDSIKLTFEATG
PRHMSFYVRTHKGSTLSQWSLGNGIPVGPGPGGRTQQMLIPAWQQVTPMAPAAATLTFEGMAGSQRL
GDWGKMIPHSNHYNSVGPGPGELQLVQLEGGGGSGTYRVGNAQPSLADCLDAGDLAQRLREHGAEVP
TEPKEGPGPGELEKFRKSEEGKQRAAAPSAASSPADVQSLKKAMSSLQNDRDRLLKELKNLGPGPGGK
HDRDLLIGTAKHGLNRTDYYIMNGPQLSFLDAYRNYAQHKRTDTQAPGSGPGPGILEVDKSGPITLLVQG
HMEGEVWGLSTHPYLPICATVSDDKTLRIWDLSPSGPGPGMLTARLLLPRLLCLQGRTTSYSTAAVLPNPI
PNPEICYNKLFINNEWHDAVGPGPG<u>EVSGLEQLESIINFEKLTEWTSSNV</u>GGPGPGMTEQQWNFAGIEA
<u>AASAIQGNVTSIHSLLD</u>*DYKDDDDKGSDYKDHDGDYKDHD*<u>MLIPIAVGGALAGLVLIVLIAYLIG*KKHCSY
QDIL*</u>

Figure 7C          (SEQ ID NO.: 18)

SEQUENCE LISTING

```
<160> NUMBER OF SEQ ID NOS: 18

<210> SEQ ID NO 1
<211> LENGTH: 993
<212> TYPE: DNA
<213> ORGANISM: Artificial Sequence
<220> FEATURE:
<223> OTHER INFORMATION: MHC-I nucleic acid for MHC-I presentation

<400> SEQUENCE: 1
atggataaaa tcacgcagta cgaaaagtca ttgtactatt gttctttcct ggaggccctc      60
gttagagatg tatgcatcgc tgcagctgcc tgtgtcgact gtcttgacag aaccaacacc     120
gcccaggtaa tggttggaaa atgtgctctg gcctaccagc tgtatgcagc cgccgcagtg     180
gtcaaagcat acctgcctgt caatgaatct ttcgccttca ctgccgattt gaggagcaat     240
actggcggcc aggcagcagc cgcaaacatc ctggctgtgt ccttcgcacc tctggtgcaa     300
```

```
ctcagtaaaa acgacaacgg aactcctgac tccgtgggag cagccgccgc acagagtaac    360
taccagcaca tcacgaattt tgagtggtgc atttccatac tggttgaact gacgcgcctg    420
gagggtgcag ctgccgctta ttacacagtg ttcgatcggg acaacaatcg ggtctctttt    480
gctaatgctg tggtgctggc cgctgccgct cacagcggac tggtcacttt ccaagccttt    540
attgatgtga tgtcaaggga acaactgaca cagacactg cagacgctgc cgcagccctg     600
gatctggccg ctttggaaga cgtctccgcc aactgtctca ctgagaccct ggaggacaag    660
aatgaaggtg tggccgctgc cgctgtcctg tcattcgtgg gccagacgag ggtgttgatg    720
atcaacgggg aagaagttga agaaacagaa ctgatgggtg ccgctgccgc agaggtgtcc    780
ggactcgagc agctggaatc tataattaac tttgaaaagt tgacggaatg gacttcctct    840
aacgtggccg ctgccgctat gacggagcaa caatggaact cgcaggcat cgaggctgcc     900 gccagcgcca tccaaggaaa cgtaacttca atccacagcc ttctggatgc tgctgctgcc    960
gaacaaaagc tcatcagtga ggaggacttg taa                                 993
```

```
<210> SEQ ID NO 2
<211> LENGTH: 1221
<212> TYPE: DNA
<213> ORGANISM: Artificial Sequence
<220> FEATURE:
<223> OTHER INFORMATION: MHC-I nucleic acid for MHC-I presentation
      (Ubiquitin, cleavable)

<400> SEQUENCE: 2
```

```
atgcagattt ttgtgaagac actgaccgga aaaactatca ccctcgaggt ggagccttcc     60
gacactatcg aaaacgtcaa ggccaagatc caggacaagg aaggcattcc acccgatcag    120
cagcgcctta tttttgcagg taagcagctg aagacggaa ggaccctgag cgactataat     180
atccagaaag aaagcacact ccacctcgtg ctcaggctcc gcggggcag ggataaaatc      240 acgcagtacg aaaagtcatt gtactattgt tctttcctgg aggccctcgt tagagatgta    300
tgcatcgctg cagctgcctg tgtcgactgt cttgacagaa ccaacaccgc ccaggtaatg    360
gttggaaaat gtgctctggc ctaccagctg tatgcagccg ccgcagtggt caaagcatac    420
ctgcctgtca atgaatcttt cgccttcact gccgatttga ggagcaatac tggcggccag    480
gcagcagccg caaacatcct ggctgtgtcc ttcgcacctc tggtgcaact cagtaaaaac    540
gacaacggaa ctcctgactc cgtgggagca gccgccgcac agagtaacta ccagcacatc    600
acgaattttg agtggtgcat ttccatactg gttgaactga cgcgcctgga gggtgcagct    660
gccgcttatt acacagtgtt cgatcgggac aacaatcggg tctcttttgc taatgctgtg    720
gtgctggccg ctgccgctca cagcggactg gtcactttcc aagcctttat tgatgtgatg    780
tcaagggaaa caactgacac agacactgca gacgctgccg cagccctgga tctggccgct    840
ttggaagacg tctccgccaa ctgtctcact gagaccctgg aggacaagaa tgaaggtgtg    900
gccgctgccg ctgtcctgtc attcgtgggc cagacgaggg tgttgatgat caacggggaa    960
gaagttgaag aaacagaact gatgggtgcc gctgccgcag aggtgtccgg actcgagcag   1020
ctggaatcta taattaactt tgaaaagttg acggaatgga cttcctctaa cgtggccgct   1080
gccgctatga cggagcaaca atggaacttc gcaggcatc aggctgccgc cagcgccatc    1140
caaggaaacg taacttcaat ccacagcctt ctggatgctg ctgctgccga acaaaagctc   1200
atcagtgagg aggacttgta a                                             1221
```

```
<210> SEQ ID NO 3
<211> LENGTH: 1215
<212> TYPE: DNA
<213> ORGANISM: Artificial Sequence
<220> FEATURE:
<223> OTHER INFORMATION: MHC-I nucleic acid for MHC-I presentation
      (Ubiquitin, non-cleavable)

<400> SEQUENCE: 3
atgcagattt tgtgaagac actgaccgga aaaactatca ccctcgaggt ggagccttcc      60
gacactatcg aaaacgtcaa ggccaagatc caggacaagg aaggcattcc acccgatcag    120
cagcgcctta tttttgcagg taagcagctg gaagacggaa ggaccctgag cgactataat    180
atccagaaag aaagcacact ccacctcgtg ctcaggctcc gcggggataa aatcacgcag    240
tacgaaaagt cattgtacta ttgttctttc ctggaggccc tcgttagaga tgtatgcatc    300
gctgcagctg cctgtgtcga ctgtcttgac agaaccaaca ccgcccaggt aatggttgga    360
aaatgtgctc tggcctacca gctgtatgca gccgccgcag tggtcaaagc atacctgcct    420
gtcaatgaat ctttcgcctt cactgccgat ttgaggagca atactggcgg ccaggcagca    480
gccgcaaaca tcctggctgt gtccttcgca cctctggtgc aactcagtaa aaacgacaac    540
ggaactcctg actccgtggg agcagccgcc gcacagagta actaccagca catcacgaat    600
tttgagtggt gcatttccat actggttgaa ctgacgcgcc tggagggtgc agctgccgct    660
tattacacag tgttcgatcg ggacaacaat cgggtctctt ttgctaatgc tgtggtgctg    720
gccgctgccg ctcacagcgg actggtcact ttccaagcct ttattgatgt gatgtcaagg    780
gaaacaactg acacagacac tgcagacgct gccgcagccc tggatctggc cgcttttggaa   840
gacgtctccg ccaactgtct cactgagacc ctggaggaca agaatgaagg tgtggccgct    900
gccgctgtcc tgtcattcgt gggccagacg agggtgttga tgatcaacgg ggaagaagtt    960
gaagaaacag aactgatggg tgccgctgcc gcagaggtgt ccggactcga gcagctggaa   1020
tctataatta actttgaaaa gttgacggaa tggacttcct ctaacgtggc cgctgccgct   1080
atgacggagc aacaatggaa cttcgcaggc atcgaggctg ccgccagcgc catccaagga   1140
aacgtaactt caatccacag ccttctggat gctgctgctg ccgaacaaaa gctcatcagt   1200
gaggaggact gtaa                                                     1215

<210> SEQ ID NO 4
<211> LENGTH: 330
<212> TYPE: PRT
<213> ORGANISM: Artificial Sequence
<220> FEATURE:
<223> OTHER INFORMATION: MHC-I polypeptide for MHC-I presentation

<400> SEQUENCE: 4

Met Asp Lys Ile Thr Gln Tyr Glu Lys Ser Leu Tyr Tyr Cys Ser Phe
1               5                   10                  15

Leu Glu Ala Leu Val Arg Asp Val Cys Ile Ala Ala Ala Cys Val
            20                  25                  30

Asp Cys Leu Asp Arg Thr Asn Thr Ala Gln Val Met Val Gly Lys Cys
        35                  40                  45

Ala Leu Ala Tyr Gln Leu Tyr Ala Ala Ala Val Val Lys Ala Tyr
    50                  55                  60

Leu Pro Val Asn Glu Ser Phe Ala Phe Thr Ala Asp Leu Arg Ser Asn
65                  70                  75                  80

Thr Gly Gly Gln Ala Ala Ala Ala Asn Ile Leu Ala Val Ser Phe Ala
                85                  90                  95
```

```
Pro Leu Val Gln Leu Ser Lys Asn Asp Asn Gly Thr Pro Asp Ser Val
            100                 105                 110

Gly Ala Ala Ala Gln Ser Asn Tyr Gln His Ile Thr Asn Phe Glu
            115                 120                 125

Trp Cys Ile Ser Ile Leu Val Glu Leu Thr Arg Leu Glu Gly Ala Ala
130                 135                 140

Ala Ala Tyr Tyr Thr Val Phe Asp Arg Asp Asn Asn Arg Val Ser Phe
145                 150                 155                 160

Ala Asn Ala Val Val Leu Ala Ala Ala His Ser Gly Leu Val Thr
                165                 170                 175

Phe Gln Ala Phe Ile Asp Val Met Ser Arg Glu Thr Thr Asp Thr Asp
            180                 185                 190

Thr Ala Asp Ala Ala Ala Leu Asp Leu Ala Ala Leu Glu Asp Val
            195                 200                 205

Ser Ala Asn Cys Leu Thr Glu Thr Leu Glu Asp Lys Asn Gly Val
            210                 215                 220

Ala Ala Ala Ala Val Leu Ser Phe Val Gly Gln Thr Arg Val Leu Met
225                 230                 235                 240

Ile Asn Gly Glu Glu Val Glu Thr Glu Leu Met Gly Ala Ala Ala
                245                 250                 255

Ala Glu Val Ser Gly Leu Glu Gln Leu Glu Ser Ile Ile Asn Phe Glu
            260                 265                 270

Lys Leu Thr Glu Trp Thr Ser Ser Asn Val Ala Ala Ala Met Thr
            275                 280                 285

Glu Gln Gln Trp Asn Phe Ala Gly Ile Glu Ala Ala Ser Ala Ile
            290                 295                 300

Gln Gly Asn Val Thr Ser Ile His Ser Leu Leu Asp Ala Ala Ala Ala
305                 310                 315                 320

Glu Gln Lys Leu Ile Ser Glu Glu Asp Leu
                325                 330

<210> SEQ ID NO 5
<211> LENGTH: 406
<212> TYPE: PRT
<213> ORGANISM: Artificial Sequence
<220> FEATURE:
<223> OTHER INFORMATION: MHC-I polypeptide for MHC-I presentation
      (Ubiquitin, cleavable)

<400> SEQUENCE: 5

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Asp Lys Ile
65                  70                  75                  80

Thr Gln Tyr Glu Lys Ser Leu Tyr Tyr Cys Ser Phe Leu Glu Ala Leu
                85                  90                  95

Val Arg Asp Val Cys Ile Ala Ala Ala Cys Val Asp Cys Leu Asp
            100                 105                 110

Arg Thr Asn Thr Ala Gln Val Met Val Gly Lys Cys Ala Leu Ala Tyr
```

```
            115                 120                 125
Gln Leu Tyr Ala Ala Ala Val Val Lys Ala Tyr Leu Pro Val Asn
    130                 135                 140
Glu Ser Phe Ala Phe Thr Ala Asp Leu Arg Ser Asn Thr Gly Gly Gln
145                 150                 155                 160
Ala Ala Ala Ala Asn Ile Leu Ala Val Ser Phe Ala Pro Leu Val Gln
                165                 170                 175
Leu Ser Lys Asn Asp Asn Gly Thr Pro Asp Ser Val Gly Ala Ala Ala
            180                 185                 190
Ala Gln Ser Asn Tyr Gln His Ile Thr Asn Phe Glu Trp Cys Ile Ser
        195                 200                 205
Ile Leu Val Glu Leu Thr Arg Leu Glu Gly Ala Ala Ala Tyr Tyr
    210                 215                 220
Thr Val Phe Asp Arg Asp Asn Asn Arg Val Ser Phe Ala Asn Ala Val
225                 230                 235                 240
Val Leu Ala Ala Ala Ala His Ser Gly Leu Val Thr Phe Gln Ala Phe
                245                 250                 255
Ile Asp Val Met Ser Arg Glu Thr Thr Asp Thr Asp Thr Ala Asp Ala
            260                 265                 270
Ala Ala Ala Leu Asp Leu Ala Ala Leu Glu Asp Val Ser Ala Asn Cys
        275                 280                 285
Leu Thr Glu Thr Leu Glu Asp Lys Asn Glu Gly Val Ala Ala Ala
    290                 295                 300
Val Leu Ser Phe Val Gly Gln Thr Arg Val Leu Met Ile Asn Gly Glu
305                 310                 315                 320
Glu Val Glu Glu Thr Glu Leu Met Gly Ala Ala Ala Glu Val Ser
                325                 330                 335
Gly Leu Glu Gln Leu Glu Ser Ile Ile Asn Phe Glu Lys Leu Thr Glu
            340                 345                 350
Trp Thr Ser Ser Asn Val Ala Ala Ala Met Thr Glu Gln Gln Trp
        355                 360                 365
Asn Phe Ala Gly Ile Glu Ala Ala Ala Ser Ala Ile Gln Gly Asn Val
    370                 375                 380
Thr Ser Ile His Ser Leu Leu Asp Ala Ala Ala Glu Gln Lys Leu
385                 390                 395                 400
Ile Ser Glu Glu Asp Leu
                405

<210> SEQ ID NO 6
<211> LENGTH: 404
<212> TYPE: PRT
<213> ORGANISM: Artificial Sequence
<220> FEATURE:
<223> OTHER INFORMATION: MHC-I polypeptide for MHC-I presentation
      (Ubiquitin, non-cleavable)

<400> SEQUENCE: 6

Met Gln Ile Phe Val Lys Thr Leu Thr Gly Lys Thr Ile Thr Leu Glu
1               5                   10                  15
Val Glu Pro Ser Asp Thr Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ser Asp Tyr Asn Ile Gln Lys Glu
    50                  55                  60
```

Ser Thr Leu His Leu Val Leu Arg Leu Arg Gly Asp Lys Ile Thr Gln
 65                  70                  75                  80

Tyr Glu Lys Ser Leu Tyr Tyr Cys Ser Phe Leu Glu Ala Leu Val Arg
                 85                  90                  95

Asp Val Cys Ile Ala Ala Ala Cys Val Asp Cys Leu Asp Arg Thr
            100                 105                 110

Asn Thr Ala Gln Val Met Val Gly Lys Cys Ala Leu Ala Tyr Gln Leu
            115                 120                 125

Tyr Ala Ala Ala Val Val Lys Ala Tyr Leu Pro Val Asn Glu Ser
        130                 135                 140

Phe Ala Phe Thr Ala Asp Leu Arg Ser Asn Thr Gly Gly Gln Ala Ala
145                 150                 155                 160

Ala Ala Asn Ile Leu Ala Val Ser Phe Ala Pro Leu Val Gln Leu Ser
            165                 170                 175

Lys Asn Asp Asn Gly Thr Pro Asp Ser Val Gly Ala Ala Ala Gln
        180                 185                 190

Ser Asn Tyr Gln His Ile Thr Asn Phe Glu Trp Cys Ile Ser Ile Leu
        195                 200                 205

Val Glu Leu Thr Arg Leu Glu Gly Ala Ala Ala Tyr Tyr Thr Val
        210                 215                 220

Phe Asp Arg Asp Asn Asn Arg Val Ser Phe Ala Asn Ala Val Val Leu
225                 230                 235                 240

Ala Ala Ala Ala His Ser Gly Leu Val Thr Phe Gln Ala Phe Ile Asp
                245                 250                 255

Val Met Ser Arg Glu Thr Thr Asp Thr Asp Thr Ala Asp Ala Ala Ala
            260                 265                 270

Ala Leu Asp Leu Ala Ala Leu Glu Asp Val Ser Ala Asn Cys Leu Thr
        275                 280                 285

Glu Thr Leu Glu Asp Lys Asn Glu Gly Val Ala Ala Ala Val Leu
        290                 295                 300

Ser Phe Val Gly Gln Thr Arg Val Leu Met Ile Asn Gly Glu Glu Val
305                 310                 315                 320

Glu Glu Thr Glu Leu Met Gly Ala Ala Ala Glu Val Ser Gly Leu
            325                 330                 335

Glu Gln Leu Glu Ser Ile Ile Asn Phe Glu Lys Leu Thr Glu Trp Thr
        340                 345                 350

Ser Ser Asn Val Ala Ala Ala Met Thr Glu Gln Trp Asn Phe
        355                 360                 365

Ala Gly Ile Glu Ala Ala Ser Ala Ile Gln Gly Asn Val Thr Ser
        370                 375                 380

Ile His Ser Leu Leu Asp Ala Ala Ala Glu Gln Lys Leu Ile Ser
385                 390                 395                 400

Glu Glu Asp Leu

<210> SEQ ID NO 7
<211> LENGTH: 1218
<212> TYPE: DNA
<213> ORGANISM: Artificial Sequence
<220> FEATURE:
<223> OTHER INFORMATION: MHC-I nucleic acid for MHC-II presentation
      (lysosomal target)

<400> SEQUENCE: 7
atgctgctgc tgccattcca gctcttggcc gtgctgttcc ccggggggaa ttctgaggat    60
aagatcaccc agtatgaaaa atccttgtat tattgtagct ttctggaagc cctggtgcga   120

```
gatgtgtgta taggcccagg gccggggtgt gttgattgcc tcgacaggac aaataccgcc      180
caggtaatgg ttggcaaatg cgcactcgca tatcaactct acggaccagg acccggcgtg      240
gtaaaggctt atctgccagt taacgagagc tttgccttca ccgcagacct gcgctccaat      300
actggtggtc aagggcccgg accaggtaat atcctcgccg tgagcttcgc ccctctggtc      360
cagctgagta aaatgacaa tggtactcct gatagtgtag gcggacccgg tccgggtcag       420
tccaattacc agcacattac caatttcgaa tggtgcatca gtatactggt tgaattgacc      480
agactcgagg ggggcccagg cccaggctac tacactgttt tcgatcgcga caataatcgg      540
gttagcttcg ctaatgcagt agtgctgggc cccgggccag ggcactccgg tctggtgacg      600
ttccaggcct tcatcgatgt aatgagccgc gagactacgg acaccgacac cgctgatggc      660
cccgggcctg gtctggatct tgcagccctg gaggatgtgt ccgctaactg tttgactgag      720
acactggagg acaagaacga gggcgtcgga ccagggcctg gtgtcctttc tttcgtcggt      780
cagacaaggg tgttgatgat caatggagaa gaggtggaag agaccgaatt gatgggaggc      840
ccagggcccg gcgaggttag cggcctggaa cagctggaga gtattatcaa ttttgaaaag      900
ctgaccgagt ggacaagctc aatgtaggc ggacctggac ccgggatgac agagcagcag      960
tggaattttg ccggtattga agctgcagcc agtgctatcc aaggcaacgt aacgagtatt     1020
cacagcctgc tcgacgacta caaagacgac gacgacaagg gcagtgacta taaggaccat     1080
gatggtgact ataaggacca cgacatcatg ctcatcccaa tcgctgtcgg aggtgctctg     1140
gccggtctcg tattgatcgt tctgatcgct tatttgatcg ggaggaagag gagtcacgca     1200
ggctaccaga ctatctag                                                  1218

<210> SEQ ID NO 8
<211> LENGTH: 1203
<212> TYPE: DNA
<213> ORGANISM: Artificial Sequence
<220> FEATURE:
<223> OTHER INFORMATION: MHC-I nucleic acid for MHC-II presentation
      (recycling endosome target)

<400> SEQUENCE: 8
atgctgctgc tgccattcca gctcttggcc gtgctgttcc ccgggggaa ttctgaggat         60 aagatcaccc agtatgaaaa atccttgtat tattgtagct ttctggaagc cctggtgcga       120
gatgtgtgta taggcccagg gccggggtgt gttgattgcc tcgacaggac aaataccgcc       180
caggtaatgg ttggcaaatg cgcactcgca tatcaactct acggaccagg acccggcgtg       240
gtaaaggctt atctgccagt taacgagagc tttgccttca ccgcagacct gcgctccaat       300
actggtggtc aagggcccgg accaggtaat atcctcgccg tgagcttcgc ccctctggtc       360
cagctgagta aaatgacaa tggtactcct gatagtgtag gcggacccgg tccgggtcag        420
tccaattacc agcacattac caatttcgaa tggtgcatca gtatactggt tgaattgacc       480
agactcgagg ggggcccagg cccaggctac tacactgttt tcgatcgcga caataatcgg       540
gttagcttcg ctaatgcagt agtgctgggc cccgggccag ggcactccgg tctggtgacg       600
ttccaggcct tcatcgatgt aatgagccgc gagactacgg acaccgacac cgctgatggc       660
cccgggcctg gtctggatct tgcagccctg gaggatgtgt ccgctaactg tttgactgag       720
acactggagg acaagaacga gggcgtcgga ccagggcctg gtgtcctttc tttcgtcggt       780
cagacaaggg tgttgatgat caatggagaa gaggtggaag agaccgaatt gatgggaggc       840
ccagggcccg gcgaggttag cggcctggaa cagctggaga gtattatcaa ttttgaaaag       900
```

```
ctgaccgagt ggacaagctc caatgtaggc ggacctggac ccgggatgac agagcagcag        960
tggaattttg ccggtattga agctgcagcc agtgctatcc aaggcaacgt aacgagtatt       1020
cacagcctgc tcgacgacta caaagacgac gacgacaagg gcagtgacta taaggaccat       1080
gatggtgact ataaggacca cgacatcatg ctcatcccaa tcgctgtcgg aggtgctctg       1140
gccggtctcg tatttgatcgt tctgatcgct tatttgatcg ggaggaaacg ctgtttctgt       1200
taa                                                                     1203

<210> SEQ ID NO 9
<211> LENGTH: 1215
<212> TYPE: DNA
<213> ORGANISM: Artificial Sequence
<220> FEATURE:
<223> OTHER INFORMATION: MHC-I nucleic acid for MHC-II presentation
      (sorting endosome target)

<400> SEQUENCE: 9
atgctgctgc tgccattcca gctcttggcc gtgctgttcc cggggggaa ttctgaggat          60 aagatcaccc agtatgaaaa atccttgtat tattgtagct ttctggaagc cctggtgcga        120
gatgtgtgta taggcccagg gccggggtgt gttgattgcc tcgacaggac aaataccgcc        180
caggtaatgg ttggcaaatg cgcactcgca tatcaactct acggaccagg acccggcgtg        240
gtaaaggctt atctgccagt taacgagagc tttgccttca ccgcagacct gcgctccaat        300
actggtggtc aagggcccgg accaggtaat atcctcgccg tgagcttcgc ccctctggtc        360
cagctgagta aaaatgacaa tggtactcct gatagtgtag gcggacccgg tccgggtcag        420
tccaattacc agcacattac caatttcgaa tggtgcatca gtatactggt tgaattgacc        480
agactcgagg gggcccagg cccaggctac tacactgttt tcgatcgcga caataatcgg        540
gttagcttcg ctaatgcagt agtgctgggc cccgggccag gcactccgg tctggtgacg        600 ttccaggcct tcatcgatgt aatgagccgc gagactacgg acaccgacac cgctgatggc        660 ccgggcctg gtctggatct tgcagccctg gaggatgtgt ccgctaactg tttgactgag        720
acactggagg acaagaacga gggcgtcgga ccagggcctg gtgtccttc tttcgtcggt        780 cagacaaggg tgttgatgat caatggagaa gaggtggaag agaccgaatt gatgggaggc        840
ccagggcccg cgaggttag cggcctgaa cagctggaga gtattatcaa ttttgaaaag        900
ctgaccgagt ggacaagctc caatgtaggc ggacctggac ccgggatgac agagcagcag        960
tggaattttg ccggtattga agctgcagcc agtgctatcc aaggcaacgt aacgagtatt       1020
cacagcctgc tcgacgacta caaagacgac gacgacaagg gcagtgacta taaggaccat       1080
gatggtgact ataaggacca cgacatcatg ctcatcccaa tcgctgtcgg aggtgctctg       1140
gccggtctcg tatttgatcgt tctgatcgct tatttgatcg ggaagaagca ctgctcatat       1200
caggacatcc tgtga                                                        1215

<210> SEQ ID NO 10
<211> LENGTH: 405
<212> TYPE: PRT
<213> ORGANISM: Artificial Sequence
<220> FEATURE:
<223> OTHER INFORMATION: MHC-I polypeptide for MHC-II presentation
      (lysosomal target)

<400> SEQUENCE: 10

Met Leu Le

```
Asn Ser Glu Asp Lys Ile Thr Gln Tyr Glu Lys Ser Leu Tyr Tyr Cys
             20                  25                  30

Ser Phe Leu Glu Ala Leu Val Arg Asp Val Cys Ile Gly Pro Gly Pro
         35                  40                  45

Gly Cys Val Asp Cys Leu Asp Arg Thr Asn Thr Ala Gln Val Met Val
     50                  55                  60

Gly Lys Cys Ala Leu Ala Tyr Gln Leu Tyr Gly Pro Gly Pro Gly Val
 65                  70                  75                  80

Val Lys Ala Tyr Leu Pro Val Asn Glu Ser Phe Ala Phe Thr Ala Asp
                 85                  90                  95

Leu Arg Ser Asn Thr Gly Gly Gln Gly Pro Gly Pro Gly Asn Ile Leu
                100                 105                 110

Ala Val Ser Phe Ala Pro Leu Val Gln Leu Ser Lys Asn Asp Asn Gly
            115                 120                 125

Thr Pro Asp Ser Val Gly Gly Pro Gly Pro Gly Gln Ser Asn Tyr Gln
        130                 135                 140

His Ile Thr Asn Phe Glu Trp Cys Ile Ser Ile Leu Val Glu Leu Thr
145                 150                 155                 160

Arg Leu Glu Gly Gly Pro Gly Pro Gly Tyr Tyr Thr Val Phe Asp Arg
                165                 170                 175

Asp Asn Asn Arg Val Ser Phe Ala Asn Ala Val Val Leu Gly Pro Gly
            180                 185                 190

Pro Gly His Ser Gly Leu Val Thr Phe Gln Ala Phe Ile Asp Val Met
        195                 200                 205

Ser Arg Glu Thr Thr Asp Thr Asp Thr Ala Asp Gly Pro Gly Pro Gly
210                 215                 220

Leu Asp Leu Ala Ala Leu Glu Asp Val Ser Ala Asn Cys Leu Thr Glu
225                 230                 235                 240

Thr Leu Glu Asp Lys Asn Glu Gly Val Gly Pro Gly Pro Gly Val Leu
                245                 250                 255

Ser Phe Val Gly Gln Thr Arg Val Leu Met Ile Asn Gly Glu Glu Val
            260                 265                 270

Glu Glu Thr Glu Leu Met Gly Gly Pro Gly Pro Gly Glu Val Ser Gly
        275                 280                 285

Leu Glu Gln Leu Glu Ser Ile Ile Asn Phe Glu Lys Leu Thr Glu Trp
290                 295                 300

Thr Ser Ser Asn Val Gly Gly Pro Gly Pro Gly Met Thr Glu Gln Gln
305                 310                 315                 320

Trp Asn Phe Ala Gly Ile Glu Ala Ala Ala Ser Ala Ile Gln Gly Asn
                325                 330                 335

Val Thr Ser Ile His Ser Leu Leu Asp Asp Tyr Lys Asp Asp Asp Asp
            340                 345                 350

Lys Gly Ser Asp Tyr Lys Asp His Asp Gly Asp Tyr Lys Asp His Asp
        355                 360                 365

Ile Met Leu Ile Pro Ile Ala Val Gly Gly Ala Leu Ala Gly Leu Val
370                 375                 380

Leu Ile Val Leu Ile Ala Tyr Leu Ile Gly Arg Lys Arg Ser His Ala
385                 390                 395                 400

Gly Tyr Gln Thr Ile
                405

<210> SEQ ID NO 11
<211> LENGTH: 400
```

<212> TYPE: PRT
<213> ORGANISM: Artificial Sequence
<220> FEATURE:
<223> OTHER INFORMATION: MHC-I polypeptide for MHC-II presentation
      (recycling endosome target)

<400> SEQUENCE: 11

```
Met Leu Leu Leu Pro Phe Gln Leu Leu Ala Val Leu Phe Pro Gly Gly
1               5                   10                  15

Asn Ser Glu Asp Lys Ile Thr Gln Tyr Glu Lys Ser Leu Tyr Tyr Cys
            20                  25                  30

Ser Phe Leu Glu Ala Leu Val Arg Asp Val Cys Ile Gly Pro Gly Pro
        35                  40                  45

Gly Cys Val Asp Cys Leu Asp Arg Thr Asn Thr Ala Gln Val Met Val
    50                  55                  60

Gly Lys Cys Ala Leu Ala Tyr Gln Leu Tyr Gly Pro Gly Pro Gly Val
65                  70                  75                  80

Val Lys Ala Tyr Leu Pro Val Asn Glu Ser Phe Ala Phe Thr Ala Asp
                85                  90                  95

Leu Arg Ser Asn Thr Gly Gly Gln Gly Pro Gly Pro Gly Asn Ile Leu
            100                 105                 110

Ala Val Ser Phe Ala Pro Leu Val Gln Leu Ser Lys Asn Asp Asn Gly
        115                 120                 125

Thr Pro Asp Ser Val Gly Gly Pro Gly Pro Gly Gln Ser Asn Tyr Gln
    130                 135                 140

His Ile Thr Asn Phe Glu Trp Cys Ile Ser Ile Leu Val Glu Leu Thr
145                 150                 155                 160

Arg Leu Glu Gly Gly Pro Gly Pro Gly Tyr Tyr Thr Val Phe Asp Arg
                165                 170                 175

Asp Asn Asn Arg Val Ser Phe Ala Asn Ala Val Val Leu Gly Pro Gly
            180                 185                 190

Pro Gly His Ser Gly Leu Val Thr Phe Gln Ala Phe Ile Asp Val Met
        195                 200                 205

Ser Arg Glu Thr Thr Asp Thr Asp Thr Ala Asp Gly Pro Gly Pro Gly
    210                 215                 220

Leu Asp Leu Ala Ala Leu Glu Asp Val Ser Ala Asn Cys Leu Thr Glu
225                 230                 235                 240

Thr Leu Glu Asp Lys Asn Glu Gly Val Gly Pro Gly Pro Gly Val Leu
                245                 250                 255

Ser Phe Val Gly Gln Thr Arg Val Leu Met Ile Asn Gly Glu Glu Val
            260                 265                 270

Glu Glu Thr Glu Leu Met Gly Gly Pro Gly Pro Gly Glu Val Ser Gly
        275                 280                 285

Leu Glu Gln Leu Glu Ser Ile Ile Asn Phe Glu Lys Leu Thr Glu Trp
    290                 295                 300

Thr Ser Ser Asn Val Gly Gly Pro Gly Pro Gly Met Thr Glu Gln Gln
305                 310                 315                 320

Trp Asn Phe Ala Gly Ile Glu Ala Ala Ala Ser Ala Ile Gln Gly Asn
                325                 330                 335

Val Thr Ser Ile His Ser Leu Leu Asp Asp Tyr Lys Asp Asp Asp Asp
            340                 345                 350

Lys Gly Ser Asp Tyr Lys Asp His Asp Gly Asp Tyr Lys Asp His Asp
        355                 360                 365

Ile Met Leu Ile Pro

Leu Ile Val Leu Ile Ala Tyr Leu Ile Gly Arg Lys Arg Cys Phe Cys
385                 390                 395                 400

<210> SEQ ID NO 12
<211> LENGTH: 404
<212> TYPE: PRT
<213> ORGANISM: Artificial Sequence
<220> FEATURE:
<223> OTHER INFORMATION: MHC-I polypeptide for MHC-II presentation
      (sorting endosome target)

<400> SEQUENCE: 12

Met Leu Leu Leu Pro Phe Gln Leu Leu Ala Val Leu Phe Pro Gly Gly
1               5                   10                  15

Asn Ser Glu Asp Lys Ile Thr Gln Tyr Glu Lys Ser Leu Tyr Tyr Cys
            20                  25                  30

Ser Phe Leu Glu Ala Leu Val Arg Asp Val Cys Ile Gly Pro Gly Pro
        35                  40                  45

Gly Cys Val Asp Cys Leu Asp Arg Thr Asn Thr Ala Gln Val Met Val
    50                  55                  60

Gly Lys Cys Ala Leu Ala Tyr Gln Leu Tyr Gly Pro Gly Pro Gly Val
65                  70                  75                  80

Val Lys Ala Tyr Leu Pro Val Asn Glu Ser Phe Ala Phe Thr Ala Asp
                85                  90                  95

Leu Arg Ser Asn Thr Gly Gly Gln Gly Pro Gly Pro Gly Asn Ile Leu
            100                 105                 110

Ala Val Ser Phe Ala Pro Leu Val Gln Leu Ser Lys Asn Asp Asn Gly
        115                 120                 125

Thr Pro Asp Ser Val Gly Gly Pro Gly Pro Gly Gln Ser Asn Tyr Gln
    130                 135                 140

His Ile Thr Asn Phe Glu Trp Cys Ile Ser Ile Leu Val Glu Leu Thr
145                 150                 155                 160

Arg Leu Glu Gly Gly Pro Gly Pro Gly Tyr Tyr Thr Val Phe Asp Arg
                165                 170                 175

Asp Asn Asn Arg Val Ser Phe Ala Asn Ala Val Val Leu Gly Pro Gly
            180                 185                 190

Pro Gly His Ser Gly Leu Val Thr Phe Gln Ala Phe Ile Asp Val Met
        195                 200                 205

Ser Arg Glu Thr Thr Asp Thr Asp Thr Ala Asp Gly Pro Gly Pro Gly
    210                 215                 220

Leu Asp Leu Ala Ala Leu Glu Asp Val Ser Ala Asn Cys Leu Thr Glu
225                 230                 235                 240

Thr Leu Glu Asp Lys Asn Glu Gly Val Gly Pro Gly Pro Gly Val Leu
                245                 250                 255

Ser Phe Val Gly Gln Thr Arg Val Leu Met Ile Asn Gly Glu Glu Val
            260                 265                 270

Glu Glu Thr Glu Leu Met Gly Gly Pro Gly Pro Gly Glu Val Ser Gly
        275                 280                 285

Leu Glu Gln Leu Glu Ser Ile Ile Asn Phe Glu Lys Leu Thr Glu Trp
    290                 295                 300

Thr Ser Ser Asn Val Gly Gly Pro Gly Pro Gly Met Thr Glu Gln Gln
305                 310                 315                 320

Trp Asn Phe Ala Gly Ile Glu Ala Ala Ala Ser Ala Ile Gln Gly Asn
                325                 330                 335

Val Thr Ser Ile His Ser Leu Leu Asp Asp Tyr Lys Asp Asp Asp Asp

```
            340             345             350
Lys Gly Ser Asp Tyr Lys Asp His Asp Gly Asp Tyr Lys Asp His Asp
        355                 360                 365
Ile Met Leu Ile Pro Ile Ala Val Gly Gly Ala Leu Ala Gly Leu Val
            370                 375                 380
Leu Ile Val Leu Ile Ala Tyr Leu Ile Gly Lys Lys His Cys Ser Tyr
385                 390                 395                 400
Gln Asp Ile Leu

<210> SEQ ID NO 13
<211> LENGTH: 2712
<212> TYPE: DNA
<213> ORGANISM: Artificial Sequence
<220> FEATURE:
<223> OTHER INFORMATION: MHC-II nucleic acid for MHC-II presentation
      (lysosomal target)

<400> SEQUENCE: 13
```

| | | | | | |
|---|---|---|---|---|---|
| atgctgctgc | tgcccttcca | gttgctggct | gtcctctttc | cggcggcaa | ctccgaggca | 60 |
| ctgcaggcct | accacctgga | tcctcaatgc | tggggcgtga | acgtgcagcc | ctactccggg | 120 |
| agccctgcca | atgtcgcagt | ttatacagct | ttggtagagc | tcatggcag | aatcatgggt | 180 |
| ctcgatcttc | cagacggcgg | gcatctcacg | ggccctggtc | cgggtgatac | cgatgaagct | 240 |
| gaggatccag | agaaaatgct | tgccaacttt | gagtccggaa | agcataagta | tcgacagaca | 300 |
| gccatgttta | ccgccaccat | gccaccagcc | gtcgagagac | tggctagatc | ctacctgagg | 360 |
| agacctgctg | tggtgtacgg | cccaggcccg | ggcaggcggt | atctgttgca | gaacacagct | 420 |
| ctcgaagtct | tcatggcaaa | tcgcacttct | gttatgttca | actttcctga | caagccacg | 480 |
| gtgaagaaag | tggtatattc | ccttcccagg | ttggggtcg | gcacaagcta | tgggctcccc | 540 |
| caagcagggc | caggaccagg | gaagattgag | cccgatatga | tgtcaatgga | acatagcttc | 600 |
| gaaacggcat | cccatgacgg | agaggctggc | ccctccccag | aagtgttgca | gggccctgga | 660 |
| cctggcaagg | ttctgatggc | atccacttcc | tacttgccct | cccaggtcac | tgagatgttt | 720 |
| aaccagggaa | gggcatttgc | agcagtcaga | ttgccttttt | gtggacacaa | aaacatctgt | 780 |
| agcctgacaa | caatccagaa | gattccacga | ctgctcgtag | gacctggacc | tggcatgccc | 840 |
| gcagccgagt | tggcactcag | cgccttcctc | gtcctcgtct | ttttgtgggt | gcattctttg | 900 |
| cgccgccttc | tcgaatgctt | ctatgtatct | gtattctcta | acgccgccat | ccatgttgta | 960 |
| caatactgtt | tcggcctcgt | gtactacggt | cctggcccg | gactcctcga | gctcctgcac | 1020 |
| tgcccacttg | gtcactgtca | tctgtgttcc | gagccgatgt | tcacgtttgt | gtaccccaca | 1080 |
| attttcccac | tcagagagac | tcctatggct | gggcttcacc | agcggcgaac | gtccatcggc | 1140 |
| ttcgtggcct | attgtggccc | aggcccaggc | gcccattttc | gccttgtgtc | aaaggaaaag | 1200 |
| atgccgtggg | acagcatcaa | actgaccttc | gaggcaaccg | gacctaggca | catgagcttc | 1260 |
| tatgtgcgca | cccacaaggg | ttctaccctc | agccagtggt | cactgggtaa | tggaattcca | 1320 |
| gtgggccctg | gaccgggagg | taggacacag | caaatgctca | ttcccgcttg | caacaggtt | 1380 |
| acacctatgg | ctccagccgc | cgccacattg | acattcgagg | gcatggccgg | atctcagagg | 1440 |
| ctgggcgact | ggggaaagat | gattccccac | agcaaccatt | acaactccgt | tgggccaggc | 1500 |
| cctggtgaac | ttcagctcgt | ccagttggag | ggcgggggcg | gcagcgggac | atatagagtc | 1560 |
| gggaacgccc | aaccatcact | cgccgattgt | ctggacgccg | ggatcttgc | ccagcgcctc | 1620 |
| agagagcatg | gcgccgaagt | gcccacagaa | cctaaagagg | gaccaggacc | cggcgagctt | 1680 |

-continued

```
gaaaagttcc gcaagtctga ggagggtaag caacgggccg ccgccccag tgccgccagc    1740 tcaccagcag acgtccagag cctgaagaag gccatgtcct ctctgcagaa tgacagggac    1800
cggctgctca aggaactgaa gaatctgggc cccggccctg ggggcaaaca cgaccgggat    1860
ctgctgattg ggaccgctaa gcacggtctg aatcgaactg attactacat catgaatgga    1920
cctcagctct catttctcga cgcatacaga aactacgccc agcataaacg aactgacaca    1980
caggctcctg gcagtggacc cggccctgga attctcgagg tggacaaaag cggccctatt    2040
actctcttgg tgcagggaca catggaggga gaggtctggg gctgtctac tcatccatac     2100 ctgcccatat cgccaccgt tagtgatgac aaaactctca gaatttggga cttgtccccg     2160
tccggcccag gtcctggtat gctcaccgct cggcttttgc tcccaaggct gctctgtctt    2220
cagggcagga ccactagtta ttcaacagcc gcagtactgc ccaatccaat cccaaacccc    2280
gagatttgtt ataataagtt gtttatcaat aacgagtggc acgacgccgt cggcccgggc    2340
cctggggaag ttagtggtct ggaacagctg gaatctatca ttaatttcga gaaactgaca    2400
gaatggactt ccagcaacgt cggggggacca ggtcctggaa tgacagagca gcagtggaat    2460
tttgccggaa ttgaggccgc tgcatctgcc atccaaggaa atgtgacatc cattcactcc    2520
ctcctcgatg attacaagga cgacgacgac aagggaagtg actacaaaga ccacgacggg    2580
gactacaagg accacgacat tatgctgatc cccatcgccg tgggcggggc cctggccggc    2640
ctcgtgctga tcgtccttat cgcctacctc atcggcagga agaggagtca cgcaggctac    2700
cagactatct ag                                                       2712
```

<210> SEQ ID NO 14
<211> LENGTH: 2697
<212> TYPE: DNA
<213> ORGANISM: Artificial Sequence
<220> FEATURE:
<223> OTHER INFORMATION: MHC-II nucleic acid for MHC-II presentation
      (recycling endosome target)

<400> SEQUENCE: 14

```
atgctgctgc tgcccttcca gttgctggct gtcctctttc ccggcggcaa ctccgaggca      60
ctgcaggcct accacctgga tcctcaatgc tggggcgtga acgtgcagcc ctactccggg     120
agccctgcca atgtcgcagt ttatacagct ttggtagagc ctcatggcag aatcatgggt     180
ctcgatcttc cagacggcgg gcatctcacg ggccctggtc cgggtgatac cgatgaagct     240
gaggatccag agaaaatgct tgccaacttt gagtccggaa agcataagta tcgacagaca     300
gccatgttta ccgccaccat gccaccagcc gtcgagagac tggctagatc ctacctgagg     360
agacctgctg tggtgtacgg cccaggcccg ggcaggcggt atctgttgca gaacacagct     420
ctcgaagtct tcatggcaaa tcgcacttct gttatgttca actttcctga caagccacg     480 gtgaagaaag tggtatattc ccttcccagg gttggggtcg gcacaagcta tgggctcccc     540
caagcagggc caggaccagg gaagattgag cccgatatga tgtcaatgga acatagcttc     600
gaaacggcat cccatgacgg agaggctggc ccctccccag aagtgttgca gggccctgga     660
cctggcaagt ttctgatggc atccacttcc tacttgccct cccaggtcac tgagatgttt     720
aaccagggaa gggcatttgc agcagtcaga ttgccttttt gtggacacaa aaacatctgt     780
agcctgacaa caatccagaa gattccacga ctgctcgtag acctggacc tggcatgccc     840 gcagccgagt tggcactcag cgccttcctc gtcctcgtct ttttgtgggt gcattctttg     900
cgccgccttc tcgaatgctt ctatgtatct gtattctcta acgccgccat ccatgttgta     960
```

```
caatactgtt tcggcctcgt gtactacggt cctggcccg gactcctcga gctcctgcac    1020
tgcccacttg gtcactgtca tctgtgttcc gagccgatgt tcacgtttgt gtaccccaca    1080
attttcccac tcagagagac tcctatggct gggcttcacc agcggcgaac gtccatcggc    1140
ttcgtggcct attgtggccc aggcccaggc gcccattttc gccttgtgtc aaaggaaaag    1200
atgccgtggg acagcatcaa actgaccttc gaggcaaccg gacctaggca catgagcttc    1260
tatgtgcgca cccacaaggg ttctacccct agccagtggt cactgggtaa tggaattcca    1320
gtgggccctg gaccgggagg taggacacag caaatgctca ttcccgcttg caacaggtt    1380 acacctatgg ctccagccgc cgccacattg acattcgagg gcatggccgg atctcagagg    1440
ctgggcgact ggggaaagat gattccccac agcaaccatt acaactccgt tgggccaggc    1500
cctggtgaac ttcagctcgt ccagttggag ggcgggggcg gcagcgggac atatagagtc    1560
gggaacgccc aaccatcact cgccgattgt ctggacgccg gggatcttgc ccagcgcctc    1620
agagagcatg gcgccgaagt gcccacagaa cctaaagagg gaccaggacc cggcgagctt    1680
gaaaagttcc gcaagtctga ggagggtaag caacggcccg ccgcccccag tgccgccagc    1740
tcaccagcag acgtccagag cctgaagaag gccatgtcct ctctgcagaa tgacagggac    1800
cggctgctca aggaactgaa gaatctgggc cccggccctg ggggcaaaca cgaccgggat    1860
ctgctgattg ggaccgctaa gcacggtctg aatcgaactg attactacat catgaatgga    1920
cctcagctct catttctcga cgcatacaga aactacgccc agcataaacg aactgacaca    1980
caggctcctg gcagtggacc cggccctgga attctcgagg tggacaaaag cggccctatt    2040
actctcttgg tgcagggaca catggaggga gaggtctggg ggctgtctac tcatccatac    2100
ctgcccatat gcgccaccgt tagtgatgac aaaactctca gaatttggga cttgtccccg    2160
tccggcccag gtcctggtat gctcaccgct cggcttttgc tcccaaggct gctctgtctt    2220
cagggcagga ccactagtta ttcaacagcc gcagtactgc ccaatccaat cccaaacccc    2280
gagatttgtt ataataagtt gtttatcaat aacgagtggc acgacgccgt cggcccgggc    2340
cctggggaag ttagtggtct ggaacagctg gaatctatca ttaatttcga gaaactgaca    2400
gaatggactt ccagcaacgt cgggggacca ggtcctggaa tgacagagca gcagtggaat    2460
tttgccggaa ttgaggccgc tgcatctgcc atccaaggaa atgtgacatc cattcactcc    2520
ctcctcgatg attacaagga cgacgacgac aagggaagtg actacaaaga ccacgacggg    2580
gactacaagg accacgacat tatgctgatc cccatcgccg tgggcggggc cctggccggc    2640
ctcgtgctga tcgtccttat cgcctacctc atcggcagga acgctgtttt ctgttaa      2697
```

<210> SEQ ID NO 15
<211> LENGTH: 2709
<212> TYPE: DNA
<213> ORGANISM: Artificial Sequence
<220> FEATURE:
<223> OTHER INFORMATION: MHC-II nucleic acid for MHC-II presentation
      (sorting endosome target)

<400> SEQUENCE: 15

```
atgctgctgc tgcccttcca gttgctggct gtcctctttc ccggcggcaa ctccgaggca     60
ctgcaggcct accacctgga tcctcaatgc tggggcgtga acgtgcagcc ctactccggg    120
agccctgcca atgtcgcagt ttatacagct ttggtagagc tcatggcag aatcatgggt    180 ctcgatcttc cagacggcgg gcatctcacg ggccctggtc cgggtgatac cgatgaagct    240
gaggatccag agaaaatgct tgccaacttt gagtccggaa agcataagta tcgacagaca    300
```

```
gccatgttta ccgccaccat gccaccagcc gtcgagagac tggctagatc ctacctgagg    360
agacctgctg tggtgtacgg cccaggcccg ggcaggcggt atctgttgca gaacacagct    420
ctcgaagtct tcatggcaaa tcgcacttct gttatgttca actttcctga caagccacg     480 gtgaagaaag tggtatattc ccttcccagg gttggggtcg gcacaagcta tgggctcccc    540
caagcagggc caggaccagg gaagattgag cccgatatga tgtcaatgga acatagcttc    600
gaaacggcat cccatgacgg agaggctggc ccctccccag aagtgttgca gggccctgga    660
cctggcaagg ttctgatggc atccacttcc tacttgccct cccaggtcac tgagatgttt    720
aaccagggaa gggcatttgc agcagtcaga ttgcctttt gtggacacaa aaacatctgt     780
agcctgacaa caatccagaa gattccacga ctgctcgtag gacctggacc tggcatgccc    840
gcagccgagt tggcactcag cgccttcctc gtcctcgtct ttttgtgggt gcattctttg    900
cgccgccttc tcgaatgctt ctatgtatct gtattctcta acgccgccat ccatgttgta    960
caatactgtt tcggcctcgt gtactacggt cctggcccg gactcctcga gctcctgcac     1020
tgcccacttg gtcactgtca tctgtgttcc gagccgatgt tcacgtttgt gtaccccaca    1080
attttcccac tcagagagac tcctatggct gggcttcacc agcggcgaac gtccatcggc    1140
ttcgtggcct attgtggccc aggcccaggc gcccatttc gccttgtgtc aaaggaaaag     1200
atgccgtggg acagcatcaa actgaccttc gaggcaaccg gacctaggca catgagcttc    1260
tatgtgcgca cccacaaggg ttctaccctc agccagtggt cactgggtaa tggaattcca    1320
gtgggccctg gaccgggagg taggacacag caaatgctca ttcccgcttg gcaacaggtt    1380
acacctatgg ctccagccgc cgccacattg acattcgagg gcatggccgg atctcagagg    1440
ctgggcgact ggggaaagat gattccccac agcaaccatt acaactccgt tgggccaggc    1500
cctggtgaac ttcagctcgt ccagttggag ggcggggggcg gcagcgggac atatagagtc    1560
gggaacgccc aaccatcact cgccgattgt ctggacgccg gggatcttgc ccagcgcctc    1620
agagagcatg gcgccgaagt gcccacagaa cctaaagagg gaccaggacc cggcgagctt    1680
gaaaagttcc gcaagtctga ggagggtaag caacgggccg ccgcccccag tgccgccagc    1740
tcaccagcag acgtccagag cctgaagaag gccatgtcct ctctgcagaa tgacagggac    1800
cggctgctca aggaactgaa gaatctgggc cccggccctg ggggcaaaca cgaccgggat    1860
ctgctgattg ggaccgctaa gcacggtctg aatcgaactg attactacat catgaatgga    1920
cctcagctct catttctcga cgcatacaga aactacgccc agcataaacg aactgacaca    1980
caggctcctg gcagtggacc cggccctgga attctcgagg tggacaaaag cggccctatt    2040
actctcttgg tgcagggaca catggaggga gaggtctggg ggctgtctac tcatccatac    2100
ctgcccatat gcgccaccgt tagtgatgac aaaaactctca gaatttggga cttgtccccg    2160
tccggcccag gtcctggtat gctcaccgct cggcttttgc tcccaaggct gctctgtctt    2220
cagggcagga ccactagtta ttcaacagcc gcagtactgc ccaatccaat cccaaacccc    2280
gagatttgtt ataataagtt gtttatcaat aacgagtggc acgacgccgt cggcccgggc    2340
cctggggaag ttagtggtct ggaacagctg gaatctatca ttaatttcga gaaactgaca    2400
gaatggactt ccagcaacgt cggggggacca ggtcctggaa tgacagagca gcagtggaat    2460
tttgccggaa ttgaggccgc tgcatctgcc atccaaggaa atgtgacatc cattcactcc    2520
ctcctcgatg attacaagga cgacgacgac aagggaagtg actacaaaga ccacgacggg    2580
gactacaagg accacgacat tatgctgatc cccatcgccg tgggcggggc cctggccggc    2640
```

```
ctcgtgctga tcgtccttat cgcctacctc atcggcaaga agcactgctc atatcaggac    2700
atcctgtga                                                            2709
```

<210> SEQ ID NO 16
<211> LENGTH: 903
<212> TYPE: PRT
<213> ORGANISM: Artificial Sequence
<220> FEATURE:
<223> OTHER INFORMATION: MHC-II polypeptide for MHC-II presentation
      (lysosomal target)

<400> SEQUENCE: 16

| | | | | | | | | | | | | | | |
|---|---|---|---|---|---|---|---|---|---|---|---|---|---|---|
| Met | Leu | Leu | Leu | Pro | Phe | Gln | Leu | Leu | Ala | Val | Leu | Phe | Pro | Gly | Gly |
| 1 | | | | 5 | | | | | 10 | | | | | 15 | |

| Asn | Ser | Glu | Ala | Leu | Gln | Ala | Tyr | His | Leu | Asp | Pro | Gln | Cys | Trp | Gly |
|---|---|---|---|---|---|---|---|---|---|---|---|---|---|---|---|
| | | | 20 | | | | 25 | | | | 30 | | | | |

| Val | Asn | Val | Gln | Pro | Tyr | Ser | Gly | Ser | Pro | Ala | Asn | Val | Ala | Val | Tyr |
|---|---|---|---|---|---|---|---|---|---|---|---|---|---|---|---|
| | | 35 | | | | 40 | | | | 45 | | | | | |

| Thr | Ala | Leu | Val | Glu | Pro | His | Gly | Arg | Ile | Met | Gly | Leu | Asp | Leu | Pro |
|---|---|---|---|---|---|---|---|---|---|---|---|---|---|---|---|
| 50 | | | | | 55 | | | | | 60 | | | | | |

| Asp | Gly | Gly | His | Leu | Thr | Gly | Pro | Gly | Pro | Gly | Asp | Thr | Asp | Glu | Ala |
|---|---|---|---|---|---|---|---|---|---|---|---|---|---|---|---|
| 65 | | | | | 70 | | | | | 75 | | | | | 80 |

| Glu | Asp | Pro | Glu | Lys | Met | Leu | Ala | Asn | Phe | Glu | Ser | Gly | Lys | His | Lys |
|---|---|---|---|---|---|---|---|---|---|---|---|---|---|---|---|
| | | | | 85 | | | | | 90 | | | | | 95 | |

| Tyr | Arg | Gln | Thr | Ala | Met | Phe | Thr | Ala | Thr | Met | Pro | Pro | Ala | Val | Glu |
|---|---|---|---|---|---|---|---|---|---|---|---|---|---|---|---|
| | | | 100 | | | | | 105 | | | | | 110 | | |

| Arg | Leu | Ala | Arg | Ser | Tyr | Leu | Arg | Arg | Pro | Ala | Val | Val | Tyr | Gly | Pro |
|---|---|---|---|---|---|---|---|---|---|---|---|---|---|---|---|
| | | 115 | | | | | 120 | | | | | 125 | | | |

| Gly | Pro | Gly | Arg | Arg | Tyr | Leu | Leu | Gln | Asn | Thr | Ala | Leu | Glu | Val | Phe |
|---|---|---|---|---|---|---|---|---|---|---|---|---|---|---|---|
| 130 | | | | | 135 | | | | | 140 | | | | | |

| Met | Ala | Asn | Arg | Thr | Ser | Val | Met | Phe | Asn | Phe | Pro | Glu | Gln | Ala | Thr |
|---|---|---|---|---|---|---|---|---|---|---|---|---|---|---|---|
| 145 | | | | | 150 | | | | | 155 | | | | | 160 |

| Val | Lys | Lys | Val | Val | Tyr | Ser | Leu | Pro | Arg | Val | Gly | Val | Gly | Thr | Ser |
|---|---|---|---|---|---|---|---|---|---|---|---|---|---|---|---|
| | | | | 165 | | | | | 170 | | | | | 175 | |

| Tyr | Gly | Leu | Pro | Gln | Ala | Gly | Pro | Gly | Pro | Gly | Lys | Ile | Glu | Pro | Asp |
|---|---|---|---|---|---|---|---|---|---|---|---|---|---|---|---|
| | | | 180 | | | | | 185 | | | | | 190 | | |

| Met | Met | Ser | Met | Glu | His | Ser | Phe | Glu | Thr | Ala | Ser | His | Asp | Gly | Glu |
|---|---|---|---|---|---|---|---|---|---|---|---|---|---|---|---|
| | | 195 | | | | | 200 | | | | | 205 | | | |

| Ala | Gly | Pro | Ser | Pro | Glu | Val | Leu | Gln | Gly | Pro | Gly | Pro | Gly | Lys | Val |
|---|---|---|---|---|---|---|---|---|---|---|---|---|---|---|---|
| | 210 | | | | | 215 | | | | | 220 | | | | |

| Leu | Met | Ala | Ser | Thr | Ser | Tyr | Leu | Pro | Ser | Gln | Val | Thr | Glu | Met | Phe |
|---|---|---|---|---|---|---|---|---|---|---|---|---|---|---|---|
| 225 | | | | | 230 | | | | | 235 | | | | | 240 |

| Asn | Gln | Gly | Arg | Ala | Phe | Ala | Ala | Val | Arg | Leu | Pro | Phe | Cys | Gly | His |
|---|---|---|---|---|---|---|---|---|---|---|---|---|---|---|---|
| | | | | 245 | | | | | 250 | | | | | 255 | |

| Lys | Asn | Ile | Cys | Ser | Leu | Thr | Thr | Ile | Gln | Lys | Ile | Pro | Arg | Leu | Leu |
|---|---|---|---|---|---|---|---|---|---|---|---|---|---|---|---|
| | | | 260 | | | | | 265 | | | | | 270 | | |

| Val | Gly | Pro | Gly | Pro | Gly | Met | Pro | Ala | Ala | Glu | Leu | Ala | Leu | Ser | Ala |
|---|---|---|---|---|---|---|---|---|---|---|---|---|---|---|---|
| | | 275 | | | | | 280 | | | | | 285 | | | |

| Phe | Leu | Val | Leu | Val | Phe | Leu | Trp | Val | His | Ser | Leu | Arg | Arg | Leu | Leu |
|---|---|---|---|---|---|---|---|---|---|---|---|---|---|---|---|
| | 290 | | | | | 295 | | | | | 300 | | | | |

| Glu | Cys | Phe | Tyr | Val | Ser | Val | Phe | Ser | Asn | Ala | Ala | Ile | His | Val | Val |
|---|---|---|---|---|---|---|---|---|---|---|---|---|---|---|---|
| 305 | | | | | 310 | | | | | 315 | | | | | 320 |

| Gln | Tyr | Cys | Phe | Gly | Leu | Val | Tyr | Tyr | Gly | Pro | Gly | Pro | Gly | Leu | Leu |
|---|---|---|---|---|---|---|---|---|---|---|---|---|---|---|---|
| | | | | 325 | | | | | 330 | | | | | 335 | |

| Glu | Leu | Leu | His | Cys | Pro | Leu | Gly | His | Cys | His | Leu | Cys | Ser | Glu | Pro |

-continued

```
                340             345             350
Met Phe Thr Phe Val Tyr Pro Thr Ile Phe Pro Leu Arg Glu Thr Pro
                    355                 360                 365
Met Ala Gly Leu His Gln Arg Arg Thr Ser Ile Gly Phe Val Ala Tyr
        370                 375                 380
Cys Gly Pro Gly Pro Gly Ala His Phe Arg Leu Val Ser Lys Glu Lys
385                 390                 395                 400
Met Pro Trp Asp Ser Ile Lys Leu Thr Phe Glu Ala Thr Gly Pro Arg
                405                 410                 415
His Met Ser Phe Tyr Val Arg Thr His Lys Gly Ser Thr Leu Ser Gln
            420                 425                 430
Trp Ser Leu Gly Asn Gly Ile Pro Val Gly Pro Gly Pro Gly Gly Arg
        435                 440                 445
Thr Gln Gln Met Leu Ile Pro Ala Trp Gln Gln Val Thr Pro Met Ala
    450                 455                 460
Pro Ala Ala Ala Thr Leu Thr Phe Glu Gly Met Ala Gly Ser Gln Arg
465                 470                 475                 480
Leu Gly Asp Trp Gly Lys Met Ile Pro His Ser Asn His Tyr Asn Ser
                485                 490                 495
Val Gly Pro Gly Pro Gly Glu Leu Gln Leu Val Gln Leu Glu Gly Gly
            500                 505                 510
Gly Gly Ser Gly Thr Tyr Arg Val Gly Asn Ala Gln Pro Ser Leu Ala
        515                 520                 525
Asp Cys Leu Asp Ala Gly Asp Leu Ala Gln Arg Leu Arg Glu His Gly
    530                 535                 540
Ala Glu Val Pro Thr Glu Pro Lys Glu Gly Pro Gly Pro Gly Glu Leu
545                 550                 555                 560
Glu Lys Phe Arg Lys Ser Glu Glu Gly Lys Gln Arg Ala Ala Ala Pro
                565                 570                 575
Ser Ala Ala Ser Ser Pro Ala Asp Val Gln Ser Leu Lys Lys Ala Met
            580                 585                 590
Ser Ser Leu Gln Asn Asp Arg Asp Arg Leu Leu Lys Glu Leu Lys Asn
        595                 600                 605
Leu Gly Pro Gly Pro Gly Gly Lys His Asp Arg Asp Leu Leu Ile Gly
    610                 615                 620
Thr Ala Lys His Gly Leu Asn Arg Thr Asp Tyr Tyr Ile Met Asn Gly
625                 630                 635                 640
Pro Gln Leu Ser Phe Leu Asp Ala Tyr Arg Asn Tyr Ala Gln His Lys
                645                 650                 655
Arg Thr Asp Thr Gln Ala Pro Gly Ser Gly Pro Gly Pro Gly Ile Leu
            660                 665                 670
Glu Val Asp Lys Ser Gly Pro Ile Thr Leu Val Gln Gly His Met
        675                 680                 685
Glu Gly Glu Val Trp Gly Leu Ser Thr His Pro Tyr Leu Pro Ile Cys
    690                 695                 700
Ala Thr Val Ser Asp Asp Lys Thr Leu Arg Ile Trp Asp Leu Ser Pro
705                 710                 715                 720
Ser Gly Pro Gly Pro Gly Met Leu Thr Ala Arg Leu Leu Pro Arg
                725                 730                 735
Leu Leu Cys Leu Gln Gly Arg Thr Thr Ser Tyr Ser Thr Ala Ala Val
            740                 745                 750
Leu Pro Asn Pro Ile Pro Asn Pro Glu Ile Cys Tyr Asn Lys Leu Phe
        755                 760                 765
```

```
Ile Asn Asn Glu Trp His Asp Ala Val Gly Pro Gly Pro Gly Glu Val
    770                 775                 780

Ser Gly Leu Glu Gln Leu Glu Ser Ile Ile Asn Phe Glu Lys Leu Thr
785                 790                 795                 800

Glu Trp Thr Ser Ser Asn Val Gly Gly Pro Gly Pro Gly Met Thr Glu
                805                 810                 815

Gln Gln Trp Asn Phe Ala Gly Ile Glu Ala Ala Ala Ser Ala Ile Gln
            820                 825                 830

Gly Asn Val Thr Ser Ile His Ser Leu Leu Asp Asp Tyr Lys Asp Asp
            835                 840                 845

Asp Asp Lys Gly Ser Asp Tyr Lys Asp His Asp Gly Asp Tyr Lys Asp
850                 855                 860

His Asp Ile Met Leu Ile Pro Ile Ala Val Gly Gly Ala Leu Ala Gly
865                 870                 875                 880

Leu Val Leu Ile Val Leu Ile Ala Tyr Leu Ile Gly Arg Lys Arg Ser
            885                 890                 895

His Ala Gly Tyr Gln Thr Ile
            900

<210> SEQ ID NO 17
<211> LENGTH: 898
<212> TYPE: PRT
<213> ORGANISM: Artificial Sequence
<220> FEATURE:
<223> OTHER INFORMATION: MHC-II polypeptide for MHC-II presentation
      (recycling endosome target)

<400> SEQUENCE: 17

```
                210                 215                 220
Leu Met Ala Ser Thr Ser Tyr Leu Pro Ser Gln Val Thr Glu Met Phe
225                 230                 235                 240

Asn Gln Gly Arg Ala Phe Ala Ala Val Arg Leu Pro Phe Cys Gly His
                245                 250                 255

Lys Asn Ile Cys Ser Leu Thr Thr Ile Gln Lys Ile Pro Arg Leu Leu
                260                 265                 270

Val Gly Pro Gly Pro Gly Met Pro Ala Ala Glu Leu Ala Leu Ser Ala
                275                 280                 285

Phe Leu Val Leu Val Phe Leu Trp Val His Ser Leu Arg Arg Leu Leu
                290                 295                 300

Glu Cys Phe Tyr Val Ser Val Phe Ser Asn Ala Ala Ile His Val Val
305                 310                 315                 320

Gln Tyr Cys Phe Gly Leu Val Tyr Tyr Gly Pro Gly Pro Gly Leu Leu
                325                 330                 335

Glu Leu Leu His Cys Pro Leu Gly His Cys His Leu Cys Ser Glu Pro
                340                 345                 350

Met Phe Thr Phe Val Tyr Pro Thr Ile Phe Pro Leu Arg Glu Thr Pro
                355                 360                 365

Met Ala Gly Leu His Gln Arg Arg Thr Ser Ile Gly Phe Val Ala Tyr
                370                 375                 380

Cys Gly Pro Gly Pro Gly Ala His Phe Arg Leu Val Ser Lys Glu Lys
385                 390                 395                 400

Met Pro Trp Asp Ser Ile Lys Leu Thr Phe Glu Ala Thr Gly Pro Arg
                405                 410                 415

His Met Ser Phe Tyr Val Arg Thr His Lys Gly Ser Thr Leu Ser Gln
                420                 425                 430

Trp Ser Leu Gly Asn Gly Ile Pro Val Gly Pro Gly Pro Gly Gly Arg
                435                 440                 445

Thr Gln Gln Met Leu Ile Pro Ala Trp Gln Gln Val Thr Pro Met Ala
                450                 455                 460

Pro Ala Ala Ala Thr Leu Thr Phe Glu Gly Met Ala Gly Ser Gln Arg
465                 470                 475                 480

Leu Gly Asp Trp Gly Lys Met Ile Pro His Ser Asn His Tyr Asn Ser
                485                 490                 495

Val Gly Pro Gly Pro Gly Glu Leu Gln Leu Val Gln Leu Glu Gly Gly
                500                 505                 510

Gly Gly Ser Gly Thr Tyr Arg Val Gly Asn Ala Gln Pro Ser Leu Ala
                515                 520                 525

Asp Cys Leu Asp Ala Gly Asp Leu Ala Gln Arg Leu Arg Glu His Gly
                530                 535                 540

Ala Glu Val Pro Thr Glu Pro Lys Glu Gly Pro Gly Pro Gly Glu Leu
545                 550                 555                 560

Glu Lys Phe Arg Lys Ser Glu Glu Gly Lys Gln Arg Ala Ala Ala Pro
                565                 570                 575

Ser Ala Ala Ser Ser Pro Ala Asp Val Gln Ser Leu Lys Lys Ala Met
                580                 585                 590

Ser Ser Leu Gln Asn Asp Arg Asp Arg Leu Leu Lys Glu Leu Lys Asn
                595                 600                 605

Leu Gly Pro Gly Pro Gly Gly Lys His Asp Arg Asp Leu Leu Ile Gly
                610                 615                 620

Thr Ala Lys His Gly Leu Asn Arg Thr Asp Tyr Tyr Ile Met Asn Gly
625                 630                 635                 640
```

-continued

```
Pro Gln Leu Ser Phe Leu Asp Ala Tyr Arg Asn Tyr Ala Gln His Lys
645 650 655

Arg Thr Asp Thr Gln Ala Pro Gly Ser Gly Pro Gly Pro Gly Ile Leu
660 665 670

Glu Val Asp Lys Ser Gly Pro Ile Thr Leu Leu Val Gln Gly His Met
675 680 685

Glu Gly Glu Val Trp Gly Leu Ser Thr His Pro Tyr Leu Pro Ile Cys
690 695 700

Ala Thr Val Ser Asp Asp Lys Thr Leu Arg Ile Trp Asp Leu Ser Pro
705 710 715 720

Ser Gly Pro Gly Pro Gly Met Leu Thr Ala Arg Leu Leu Leu Pro Arg
725 730 735

Leu Leu Cys Leu Gln Gly Arg Thr Thr Ser Tyr Ser Thr Ala Ala Val
740 745 750

Leu Pro Asn Pro Ile Pro Asn Pro Glu Ile Cys Tyr Asn Lys Leu Phe
755 760 765

Ile Asn Asn Glu Trp His Asp Ala Val Gly Pro Gly Pro Gly Glu Val
770 775 780

Ser Gly Leu Glu Gln Leu Glu Ser Ile Ile Asn Phe Glu Lys Leu Thr
785 790 795 800

Glu Trp Thr Ser Ser Asn Val Gly Gly Pro Gly Pro Gly Met Thr Glu
805 810 815

Gln Gln Trp Asn Phe Ala Gly Ile Glu Ala Ala Ala Ser Ala Ile Gln
820 825 830

Gly Asn Val Thr Ser Ile His Ser Leu Leu Asp Asp Tyr Lys Asp Asp
835 840 845

Asp Asp Lys Gly Ser Asp Tyr Lys Asp His Asp Gly Asp Tyr Lys Asp
850 855 860

His Asp Ile Met Leu Ile Pro Ile Ala Val Gly Gly Ala Leu Ala Gly
865 870 875 880

Leu Val Leu Ile Val Leu Ile Ala Tyr Leu Ile Gly Arg Lys Arg Cys
885 890 895

Phe Cys

<210> SEQ ID NO 18
<211> LENGTH: 902
<212> TYPE: PRT
<213> ORGANISM: Artificial Sequence
<220> FEATURE:
<223> OTHER INFORMATION: MHC-II polypeptide for MHC-II presentation
(sorting endosome target)

<400> SEQUENCE: 18

Met Leu Leu Leu Pro Phe Gln Leu Leu Ala Val Leu Phe Pro Gly Gly
1 5 10 15

Asn Ser Glu Ala Leu Gln Ala Tyr His Leu Asp Pro Gln Cys Trp Gly
20 25 30

Val Asn Val Gln Pro Tyr Ser Gly Ser Pro Ala Asn Val Ala Val Tyr
35 40 45

Thr Ala Leu Val Glu Pro His Gly Arg Ile Met Gly Leu Asp Leu Pro
50 55 60

Asp Gly Gly His Leu Thr Gly Pro Gly Pro Gly Asp Thr Asp Glu Ala
65 70 75 80

Glu Asp Pro Glu Lys Met Leu Ala Asn Phe Glu Ser Gly Lys His Lys
85 90 95

```
Tyr Arg Gln Thr Ala Met Phe Thr Ala Thr Met Pro Pro Ala Val Glu
            100                 105                 110

Arg Leu Ala Arg Ser Tyr Leu Arg Arg Pro Ala Val Val Tyr Gly Pro
            115                 120                 125

Gly Pro Gly Arg Arg Tyr Leu Leu Gln Asn Thr Ala Leu Glu Val Phe
130                 135                 140

Met Ala Asn Arg Thr Ser Val Met Phe Asn Phe Pro Glu Gln Ala Thr
145                 150                 155                 160

Val Lys Lys Val Val Tyr Ser Leu Pro Arg Val Gly Val Gly Thr Ser
            165                 170                 175

Tyr Gly Leu Pro Gln Ala Gly Pro Gly Pro Gly Lys Ile Glu Pro Asp
            180                 185                 190

Met Met Ser Met Glu His Ser Phe Glu Thr Ala Ser His Asp Gly Glu
            195                 200                 205

Ala Gly Pro Ser Pro Glu Val Leu Gln Gly Pro Gly Pro Gly Lys Val
210                 215                 220

Leu Met Ala Ser Thr Ser Tyr Leu Pro Ser Gln Val Thr Glu Met Phe
225                 230                 235                 240

Asn Gln Gly Arg Ala Phe Ala Ala Val Arg Leu Pro Phe Cys Gly His
            245                 250                 255

Lys Asn Ile Cys Ser Leu Thr Thr Ile Gln Lys Ile Pro Arg Leu Leu
            260                 265                 270

Val Gly Pro Gly Pro Gly Met Pro Ala Ala Glu Leu Ala Leu Ser Ala
            275                 280                 285

Phe Leu Val Leu Val Phe Leu Trp Val His Ser Leu Arg Arg Leu Leu
            290                 295                 300

Glu Cys Phe Tyr Val Ser Val Phe Ser Asn Ala Ala Ile His Val Val
305                 310                 315                 320

Gln Tyr Cys Phe Gly Leu Val Tyr Tyr Gly Pro Gly Pro Gly Leu Leu
            325                 330                 335

Glu Leu Leu His Cys Pro Leu Gly His Cys His Leu Cys Ser Glu Pro
            340                 345                 350

Met Phe Thr Phe Val Tyr Pro Thr Ile Phe Pro Leu Arg Glu Thr Pro
            355                 360                 365

Met Ala Gly Leu His Gln Arg Arg Thr Ser Ile Gly Phe Val Ala Tyr
370                 375                 380

Cys Gly Pro Gly Pro Gly Ala His Phe Arg Leu Val Ser Lys Glu Lys
385                 390                 395                 400

Met Pro Trp Asp Ser Ile Lys Leu Thr Phe Glu Ala Thr Gly Pro Arg
            405                 410                 415

His Met Ser Phe Tyr Val Arg Thr His Lys Gly Ser Thr Leu Ser Gln
            420                 425                 430

Trp Ser Leu Gly Asn Gly Ile Pro Val Gly Pro Gly Pro Gly Gly Arg
            435                 440                 445

Thr Gln Gln Met Leu Ile Pro Ala Trp Gln Val Thr Pro Met Ala
            450                 455                 460

Pro Ala Ala Ala Thr Leu Thr Phe Glu Gly Met Ala Gly Ser Gln Arg
465                 470                 475                 480

Leu Gly Asp Trp Gly Lys Met Ile Pro His Ser Asn His Tyr Asn Ser
            485                 490                 495

Val Gly Pro Gly Pro Gly Glu Leu Gln Leu Val Gln Leu Glu Gly Gly
            500                 505                 510
```

```
Gly Gly Ser Gly Thr Tyr Arg Val Gly Asn Ala Gln Pro Ser Leu Ala
        515                 520                 525

Asp Cys Leu Asp Ala Gly Asp Leu Ala Gln Arg Leu Arg Glu His Gly
    530                 535                 540

Ala Glu Val Pro Thr Glu Pro Lys Glu Gly Pro Gly Pro Gly Glu Leu
545                 550                 555                 560

Glu Lys Phe Arg Lys Ser Glu Glu Gly Lys Gln Arg Ala Ala Ala Pro
                565                 570                 575

Ser Ala Ala Ser Ser Pro Ala Asp Val Gln Ser Leu Lys Lys Ala Met
            580                 585                 590

Ser Ser Leu Gln Asn Asp Arg Asp Arg Leu Leu Lys Glu Leu Lys Asn
            595                 600                 605

Leu Gly Pro Gly Pro Gly Gly Lys His Asp Arg Asp Leu Leu Ile Gly
        610                 615                 620

Thr Ala Lys His Gly Leu Asn Arg Thr Asp Tyr Tyr Ile Met Asn Gly
625                 630                 635                 640

Pro Gln Leu Ser Phe Leu Asp Ala Tyr Arg Asn Tyr Ala Gln His Lys
                645                 650                 655

Arg Thr Asp Thr Gln Ala Pro Gly Ser Gly Pro Gly Pro Gly Ile Leu
                660                 665                 670

Glu Val Asp Lys Ser Gly Pro Ile Thr Leu Leu Val Gln Gly His Met
                675                 680                 685

Glu Gly Glu Val Trp Gly Leu Ser Thr His Pro Tyr Leu Pro Ile Cys
        690                 695                 700

Ala Thr Val Ser Asp Asp Lys Thr Leu Arg Ile Trp Asp Leu Ser Pro
705                 710                 715                 720

Ser Gly Pro Gly Pro Gly Met Leu Thr Ala Arg Leu Leu Pro Arg
            725                 730                 735

Leu Leu Cys Leu Gln Gly Arg Thr Thr Ser Tyr Ser Thr Ala Ala Val
                740                 745                 750

Leu Pro Asn Pro Ile Pro Asn Pro Glu Ile Cys Tyr Asn Lys Leu Phe
            755                 760                 765

Ile Asn Asn Glu Trp His Asp Ala Val Gly Pro Gly Pro Gly Glu Val
            770                 775                 780

Ser Gly Leu Glu Gln Leu Glu Ser Ile Ile Asn Phe Glu Lys Leu Thr
785                 790                 795                 800

Glu Trp Thr Ser Ser Asn Val Gly Gly Pro Gly Pro Gly Met Thr Glu
                805                 810                 815

Gln Gln Trp Asn Phe Ala Gly Ile Glu Ala Ala Ala Ser Ala Ile Gln
            820                 825                 830

Gly Asn Val Thr Ser Ile His Ser Leu Leu Asp Asp Tyr Lys Asp Asp
            835                 840                 845

Asp Asp Lys Gly Ser Asp Tyr Lys Asp His Asp Gly Asp Tyr Lys Asp
        850                 855                 860

His Asp Ile Met Leu Ile Pro Ile Ala Val Gly Gly Ala Leu Ala Gly
865                 870                 875                 880

Leu Val Leu Ile Val Leu Ile Ala Tyr Leu Ile Gly Lys Lys His Cys
                885                 890                 895

Ser Tyr Gln Asp Ile Leu
            900
```

TARGETED NEOEPITOPE VECTORS AND METHODS THEREFOR

This application claims priority to our U.S. provisional patent application with the Ser. No. 62/489,102, filed Apr. 24, 2017.

FIELD OF THE INVENTION

The field of the invention is compositions and methods of improved neoepitope-based immune therapeutics, especially as it relates to recombinant nucleic acid therapeutics in the treatment of cancer.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer immunotherapies targeting certain antigens common to a specific cancer have led to remarkable responses in some patients. Unfortunately, many patients failed to respond to such immunotherapy despite apparent expression of the same antigen. One possible reason for such failure could be that various effector cells of the immune system may not have been present in sufficient quantities, or may have been exhausted. Moreover, intracellular antigen processing and HLA variability among patients may have led to insufficient processing of the antigen and/or antigen display, leading to a therapeutically ineffective or lacking response.

To increase the selection of targets for immune therapy, random mutations have more recently been considered since some random mutations in tumor cells may give rise to unique tumor specific antigens (neoepitopes). As such, and at least conceptually, neoepitopes may provide a unique precision target for immunotherapy. Additionally, it has been shown that cytolytic T-cell responses can be triggered by very small quantities of peptides (e.g., Sykulev et al., *Immunity*, Volume 4, Issue 6, p 565-571, 1 Jun. 1996). Moreover, due to the relatively large number of mutations in many cancers, the number of possible targets is relatively high. In view of these findings, the identification of cancer neoepitopes as therapeutic targets has attracted much attention. Unfortunately, current data appear to suggest that all or almost all cancer neoepitopes are unique to a patient and specific tumor and fail to provide any specific indication as to which neoepitope may be useful for an immunotherapeutic agent that is therapeutically effective.

To overcome at least some of the problems associated with large numbers of possible targets for immune therapy, the neoepitopes can be filtered for the type of mutation (e.g., to ascertain missense or nonsense mutation), the level of transcription to confirm transcription of the mutated gene, and to confirm protein expression. Moreover, the so filtered neoepitope may be further analyzed for specific binding to the patient's HLA system as described in WO 2016/172722. While such system advantageously reduces the relatively large number of potential neoepitopes, the significance of these neoepitopes with respect to treatment outcome remains uncertain. Still further, and especially where multiple peptides are to be expressed in an antigen presenting cell (e.g., dendritic cell), processing of precursor proteins to generate the neoepitopes is not fully understood and contributes as such to the lack of predictability of therapeutic success.

Immune therapy can be performed using at least two conceptually distinct approaches, with the first approach based on DNA vaccination and the second approach based on use of a recombinant virus that encodes one or more antigens that are expressed in a cell infected with the virus. For example, clinical trials have suggested that plasmid DNA vaccines are safe and immunologically effective in humans at doses of 300 mcg of plasmid DNA encoding HIV rev and env proteins when administered intramuscularly. Such DNA vaccination elicited antigen-specific, IFN gamma-secreting T cell responses in HIV-seronegative patients (*J. Infect. Dis.* (2000) 181:476-83). In addition, results of a clinical trial targeting PSMA (prostate-specific membrane antigen) in patients with prostate cancer using intradermal injections of plasmid DNA and adenovirus have been reported (see *Eur. Urol.* (2000), 38:208 217). Here, 26 patients were immunized either in a prime/boost strategy with an adenoviral vector expressing PSMA followed by immunization with plasmid DNA encoding PSMA, or with plasmid DNA alone, and no significant toxicity were observed. However, therapeutic efficacy of such vaccinations, particularly in treatment of cancer has not been demonstrated using such approaches. In still other examples, adenoviral expression of cancer neoepitopes has been reported as described in US 2017/0312351. While such approaches are highly specific towards the patient and tumor of the patient, generation of sufficient quantities of viral particles that encode one or more neoepitopes is time consuming. For example, virus production to generate a single dose of $10^{11}$ virus particles will often require 6-8 weeks and in some cases even longer, and multiple administrations are often required to elicit a therapeutic effect. Depending on the type of cancer and growth speed, such production time frame can be prohibitive. In addition, immune stimulation with virally expressed proteins only is often less effective, and additional treatment modalities such as cytokines are frequently required to elicit a desirable therapeutic effect.

Thus, even though multiple methods of identification and delivery of neoepitopes to various cells are known in the art, all or almost all of them suffer from various disadvantages, particularly in terms of efficacy and time requirements. Consequently, it would be desirable to have improved systems and methods for neoepitope selection and production that increases the likelihood of a therapeutic response in immune therapy in an expedient fashion.

SUMMARY OF THE INVENTION

The inventive subject matter is directed to various immune therapeutic compositions and methods, and especially recombinant expression systems in which multiple neoepitopes are combined to form a rational-designed polypeptide with a trafficking signal to increase antigen processing and presentation and to so enhance therapeutic efficacy. Additionally, the systems and methods contemplated herein take advantage of multiple and distinct vaccination modalities that will provide both, significantly shortened time-tofirst-vaccination periods and different and complementary modes of immune stimulation.

For example, where the first vaccination modality comprises a DNA vaccination that encodes a polytope (typically comprising multiple neoepitopes and/or TAAs), the vaccine can be prepared within a few days and will provide a TLR stimulus (e.g., TLR9 stimulus), while the second vaccination modality may comprise a recombinant bacterial or yeast vaccine that encodes the polytope (typically the same polytope as the first) and will so provide a different TRL stimulus (e.g., TRL1, TLR2, TLR5, etc.). In yet another example, the first vaccination modality may comprise a bacterial or yeast vaccine that encodes the polytope and the second vaccination modality may comprise a recombinant virus that encodes the polytope, which once again will provide distinct (and typically complementary or even synergistic) innate immune stimuli.

As will be readily apparent, such multi-modality strategy will substantially reduce the time to generate the first vaccination as DNA, bacterial, and yeast vaccines can be prepared within a few days rather than several weeks as is the case with most viral vaccines. Moreover, due to the distinct forms of delivery, contemplated vaccine compositions and methods will also take advantage of the distinct immune stimulatory effects provided by the different modalities and will as such be particularly useful in a prime/boost regimen. Additionally, it should be recognized that contemplated systems and methods take advantage of substantially the same polytope across the different vaccine modalities. In other words, once antigens with potential therapeutic effect are determined for a patient, a recombinant nucleic acid encoding these antigens can be assembled into a polytope cassette that can then be used across multiple vaccine platforms.

In one aspect of the inventive subject matter, the inventors contemplate a method of generating recombinant expression constructs for use in immune therapy in a mammal. Such methods will typically include a step of generating a first recombinant nucleic acid having a sequence that encodes a polytope, wherein the polytope comprises a plurality of filtered neoepitope sequences, wherein the polytope further comprises a trafficking element that directs the polytope to a sub-cellular location selected from the group consisting of a recycling endosome, a sorting endosome, and a lysosome, and wherein the first recombinant nucleic acid comprises a first promoter operably linked to the sequence that encodes the polytope to drive expression of the polytope in the mammal. In another step, a second recombinant nucleic acid is generated having the same sequence that encodes the polytope, wherein the second recombinant nucleic acid comprises a second promoter operably linked to the sequence that encodes the polytope to drive expression of the polytope in a non-mammalian cell;

For example, in exemplary embodiments the first promoter may be a constitutive promoter or a promoter that is inducible by hypoxia, IFN-gamma, or IL-8. Additionally, the trafficking element may be a CD1b leader sequence, a CD1a tail, a CD1c tail, or a LAMP1-transmembrane sequence. Most typically, the filtered neoepitope sequences are filtered by comparing tumor versus matched normal of the same patient, and/or filtered to have binding affinity to an MHC complex of equal or less than 200 nM. While in some aspects, the filtered neoepitope sequences are calculated to bind to MHC-I and the trafficking element directs the polytope to the recycling endosome, sorting endosome, or lysosome, in other aspects the filtered neoepitope sequences are calculated to bind to MHC-II and the trafficking element directs the polytope to the recycling endosome, sorting endosome, or lysosome.

Where desired, the first recombinant nucleic acid further may further comprise an additional sequence that encodes a second polytope, wherein the second polytope comprises a second trafficking element that directs the second polytope to a different sub-cellular location and wherein the second polytope comprises a second plurality of filtered neoepitope sequences. In some embodiments, at least one of the filtered neoepitope sequences and at least one of the second filtered neoepitope sequences may be the same.

It is still further contemplated that the first recombinant nucleic acid further comprises a sequence that encodes at least one of a co-stimulatory molecule, an immune stimulatory cytokine, and a protein that interferes with or down-regulates checkpoint inhibition. For example, suitable co-stimulatory molecules include CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and/or LFA3, while suitable immune stimulatory cytokine include IL-2, IL-12, IL-15, IL-15 super agonist (ALT803), IL-21, IPS1, and/or LMP1, and/or suitable proteins that interfere include antibodies against or antagonists of CTLA-4, PD-1, TIM1 receptor, 2B4, and/or CD160.

While not limiting to the inventive subject matter, the first recombinant nucleic acid may be replicated in a bacterial cell or a yeast cell, and/or the first recombinant nucleic acid may be an expression vector or a shuttle vector for generation of a recombinant virus (e.g., adenovirus, optionally with at least one of an E1 and an E2b gene deleted). It is also contemplated that such methods may also include a step of formulating the first recombinant nucleic acid into a pharmaceutical formulation for injection.

Most typically, the second promoter is a constitutive bacterial or a yeast promoter. Therefore, suitable non-mammalian cells include *E. coli* cell and *Saccharomyces cerevisiae*. In such cases, methods may include the additional steps of transfecting the second recombinant nucleic acid into a bacterial cell or a yeast cell; expressing the polytope in the bacterial cell or the yeast cell; and formulating the bacterial cell or the yeast cell into a pharmaceutical formulation for injection.

Consequently, the inventors also contemplate a recombinant bacterial or yeast expression vector for immune therapy of a mammal. Most preferably, such vector will include a recombinant nucleic acid having a sequence that encodes a polytope operably linked to a bacterial or yeast promoter to drive expression of the polytope, wherein the polytope comprises a trafficking element that directs the polytope to a sub-cellular location of a mammalian immune competent cell selected from the group consisting of recycling endosome, sorting endosome, and lysosome; and wherein the polytope comprises a plurality of filtered neoepitope sequences.

Preferably, but not necessarily, the promoter is a constitutive promoter, while the trafficking element is selected from the group consisting of a CD1b leader sequence, a CD1a tail, a CD1c tail, and a LAMP1-transmembrane sequence. As noted earlier, the filtered neoepitope sequences may be filtered by comparing tumor versus matched normal of the same patient, and the filtered neoepitope sequences bind to MHC-I and/or MHC-II, and the trafficking element directs the polytope to the recycling endosome, sorting endosome, or lysosome. It is still further contemplated that the recombinant nucleic acid may also comprise an additional sequence that encodes a second polytope, wherein the second polytope comprises a second trafficking element that directs the second polytope to a different sub-cellular location and wherein the second polytope comprises a second plurality of filtered neoepitope sequences. As before, at least one of the filtered neoepitope sequences and at least one of the second filtered neoepitope sequences may be identical.

In still further contemplated aspects, the expression vector is a bacterial expression vector or a yeast expression vector. Therefore, recombinant yeast cells and bacterial cells transfected with the vector contemplated above are particularly contemplated. These cells may then be formulated into a pharmaceutical composition comprising the recombinant yeast cells or bacterial cells.

In a further aspect of the on inventive subject matter, the inventors also contemplate a method of preparing first and second treatment compositions for an individual having a tumor. Such methods will typically include a step of identifying a plurality of expressed neoepitope sequences from omics data of the tumor, wherein each of the expressed neoepitope sequences have a calculated binding affinity of equal or less than 500 nM to at least one of MHC-I and MHC-II of the individual, and a further step of generating a first recombinant nucleic acid having a sequence that encodes a polytope, wherein the polytope comprises the plurality of expressed neoepitope sequences. Preferably, the polytope further comprises a trafficking element that directs the polytope to a sub-cellular location selected from the group consisting of a recycling endosome, a sorting endosome, and a lysosome, and the first recombinant nucleic acid comprises a first promoter operably linked to the sequence that encodes the polytope to drive expression of the polytope in a cell of the individual. In another step, the first recombinant nucleic is formulated into a DNA vaccine formulation to so obtain the first treatment composition. In yet another step, a second recombinant nucleic acid is generated that includes the sequence that encodes the polytope, wherein the second recombinant nucleic acid comprises a second promoter operably linked to the sequence that encodes the polytope to drive expression of the polytope in a bacterial cell or a yeast cell, and in a further step, the bacterial cell or the yeast cell is transfected with the second recombinant nucleic acid and expressing the polytope in the bacterial cell or the yeast cell. In a still further step, the transfected bacterial cell or the yeast cell is formulated into a cell-based vaccine formulation to so obtain the second treatment composition.

Most typically, the expressed neoepitope sequences are identified using incremental synchronous alignment of omics data from the tumor and omics data from a non-tumor sample of the same individual. It is further generally preferred that the first recombinant nucleic acid is an expression vector, and/or that the trafficking element is a CD1b leader sequence, a CD1a tail, a CD1c tail, or a LAMP1-transmembrane sequence. The second promoter is preferably a constitutive bacterial or a yeast promoter, and the bacterial cell or the yeast cell is preferably E. coli cell or Saccharomyces cerevisiae. Most typically, the cell-based vaccine formulation is formulated for injection. Furthermore, where desired, such method may further comprise a step of generating a third recombinant nucleic acid that is a viral expression vector that includes the sequence that encodes the polytope, wherein the third recombinant nucleic acid comprises a third promoter operably linked to the sequence that encodes the polytope to drive expression of the polytope in a cell of the individual.

In still another aspect of the on inventive subject matter, the inventors also contemplate a method of preparing first and second treatment compositions for an individual having a tumor that includes a step of identifying a plurality of expressed neoepitope sequences from omics data of the tumor, wherein the expressed neoepitope sequences have a calculated binding affinity of equal or less than 500 nM to at least one of MHC-I and MHC-II of the individual; and a further step of generating a first recombinant nucleic acid having a sequence that encodes a polytope, wherein the polytope comprises the plurality of expressed neoepitope sequences, wherein the first recombinant nucleic acid is a viral expression vector. Preferably, the polytope further comprises a trafficking element that directs the polytope to a sub-cellular location selected from the group consisting of a recycling endosome, a sorting endosome, and a lysosome, and the first recombinant nucleic acid comprises a first promoter operably linked to the sequence that encodes the polytope to drive expression of the polytope in a cell of the individual. In a further step, viral particles are generated from the viral expression vector and the viral particles are formulated into a viral vaccine formulation to so obtain the first treatment composition. Such methods will also include a step of generating a second recombinant nucleic acid having the sequence that encodes the polytope, wherein the second recombinant nucleic acid comprises a second promoter operably linked to the sequence that encodes the polytope to drive expression of the polytope in a non-mammalian cell, and a further step of transfecting a bacterial cell or a yeast cell with the second recombinant nucleic acid and expressing the polytope in the bacterial cell or the yeast cell. The so transfected bacterial cell or the yeast cell is then formulated into a cell-based vaccine formulation to so obtain the second treatment composition.

Most typically, the plurality of expressed neoepitope sequences are identified using incremental synchronous alignment of omics data from the tumor and omics data from a non-tumor sample of the same individual, and/or the trafficking element is a CD1b leader sequence, a CD1a tail, a CD1c tail, or a LAMP1-transmembrane sequence. Likewise, it is preferred that the first promoter is a constitutive promoter or that the first promoter is inducible by hypoxia, IFN-gamma, or IL-8, and/or the second promoter is a constitutive bacterial or a yeast promoter. In further contemplated embodiments, the viral expression vector is an adenoviral expression vector, optionally having E1 and E2b genes deleted. While not limiting to the inventive subject matter, it is generally preferred that the non-mammalian cell or the yeast cell is an E. coli cell or a Saccharomyces cerevisiae cell, and/or that the viral vaccine formulation and the cell-based vaccine formulation are both formulated for injection.

Various objects, features, aspects and advantages of the inventive subject matter will become more apparent from the following detailed description of preferred embodiments, along with the accompanying drawing in which like numerals represent like components.

BRIEF DESCRIPTION OF THE DRAWING

FIG. 1 is a schematic representation of various neoepitope arrangements.

FIG. 2 is an exemplary and partial schematic for selecting preferred arrangements of neoepitopes.

Prior Art FIG. 3 is a schematic illustration of antigen processing in the cytoplasm and MHC-I presentation.

Prior Art FIG. 4 is a schematic illustration of antigen processing in the lysosomal and endosomal compartment and MHC-II presentation.

FIGS. 5A-5C are exemplary sequence arrangements for class I antigen processing in the cytoplasm and MHC-I presentation.

FIGS. 6A-6C are exemplary sequence arrangements for class I antigen processing in the cytoplasm and MHC-II presentation.

FIGS. 7A-7C are exemplary sequence arrangements for class II antigen processing in the cytoplasm and MHC-II presentation.

DETAILED DESCRIPTION

Figure 8:
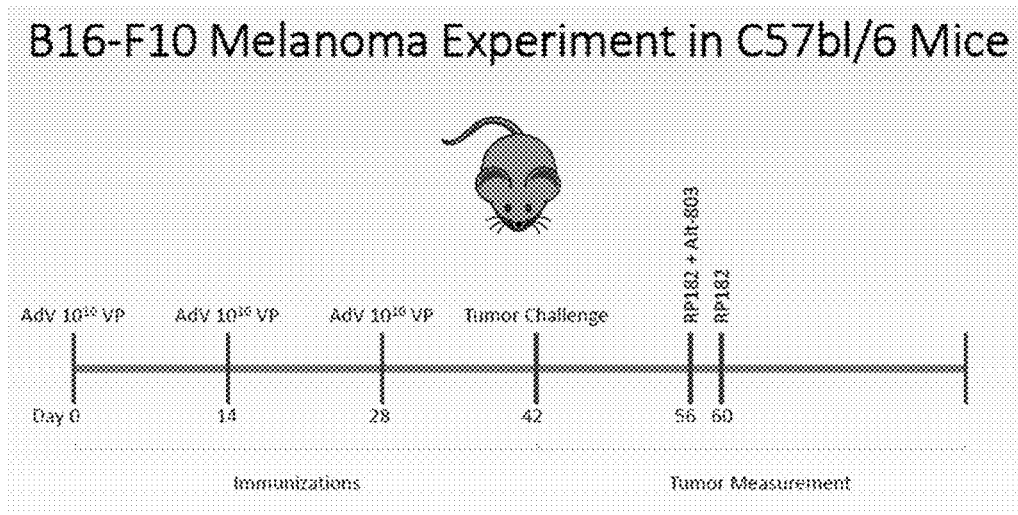
FIG. 8 is an exemplary prophylactic vaccination schedule for B16-F10 melanoma.

The inventors have now discovered that various aspects in tumor antigen-based and/or neoepitope-based immune therapy can further be improved by not only targeting the antigens or neoepitopes towards specific processing and cell surface presentation pathways, but also by using different vaccine modalities that preferably trigger different immune stimulatory pathways.

Therefore, in addition to a viral cancer vaccine that is based on a recombinant virus that triggers in a host cell expression of tumor associated or tumor specific antigens, the same (and/or additional) antigens may be expressed from a DNA vaccine and/or provided in yeast and/or bacterial cells that are genetically engineered to express these antigens. For example, where a plasmid is used in a DNA vaccine, innate immune response mechanisms against free DNA (e.g., TLR9- or STING-based) may be triggered along with the adaptive immune response based on in vivo expression of the free DNA. In another example, where a viral expression vector is employed as part of a viral vaccine in which a virus infects patient cells, such infection will typically trigger different innate immune response mechanisms (typically TLR2, TLR4, TLR 7, TLR 8, TLR 9). In still another example, where a bacterial or yeast vaccine is used in which the bacterium or yeast has expressed the antigen(s), such vaccine vaccination will once more trigger distinct innate immune response mechanisms (typically TLR1-3 for bacterial and TLR1-4 for yeast). As will be readily appreciated, triggering of various and distinct innate immune response mechanisms may provide complementary or even synergistic enhancement of the vaccine compositions.

Thus, it should be appreciated that the compositions and methods presented herein will preferably include use of at least two different vaccine modalities. For example, the first modality may be a modality selected from the group consisting of a DNA vaccine, protein vaccine, a bacterial vaccine, a yeast vaccine, and a viral vaccine, while the second/subsequent modality may be another, different, modality selected from the same group. Most preferably, the antigens present in any of the modalities will overlap or be the same to take advantage of a prime/boost effect upon repeated antigenic challenge.

In addition, it should be recognized that beyond the benefit of triggering multiple distinct innate immune pathways, contemplated compositions and methods also allow for a rapid start of treatment if a patient with respect to the point in time at which the tumor relevant antigens in the patient were identified. Indeed, it should be recognized that a DNA vaccine can be prepared based on the relevant antigens within a few days, typically within less than a week and even less than 4 days, or even less 48 hours. Moreover, bacterial or yeast vaccines can be also prepared using (the same) antigens within a few days, typically within less than 2 weeks, and more typically within less than 1 week. At the same time, a viral vaccine can be prepared when the patient already received the first vaccines (e.g., DNA vaccine, bacterial vaccine, and/or yeast vaccine).

Viewed from a different perspective, it should be appreciated that the compositions and methods presented herein will include one or more tumor associated antigens, tumor specific antigens, and/or neoepitopes that are specific to the patient and the tumor in the patient to allow for targeted treatment. Moreover, such treatment may advantageously be tailored to achieve one or more specific immune reactions, including an innate immune response, a $CD4^+$ biased immune response, a $CD8^+$ biased immune response, antibody biased immune response, and/or a stimulated immune response (e.g., reducing checkpoint inhibition and/or by activation of immune competent cells using cytokines). Most typically, such effects are in achieved in the context of the neoepitopes originating from the recombinant nucleic acid that can be administered via one or more routes in one or more distinct formats (e.g., as recombinant plasmid and as recombinant virus).

Antigens

With respect to suitable therapeutic antigens it is contemplated that various antigens are deemed suitable for use herein. However, particularly preferred antigens include tumor associated antigens (e.g., CEA, MUC1, brachyury), tumor specific antigens (e.g., HER2, PSA, PSMA, etc.), and especially tumor and patient specific antigens (i.e., neoepitopes). Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a content filter through which silent and other non-relevant (e.g., non-expressed) mutations are eliminated. It should also be appreciated that neoepitope sequences can be defined as sequence stretches with relatively short length (e.g., 8-12 mers or 14-20mers) wherein such stretches will include the change(s) in the amino acid sequences. Most typically, but not necessarily, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic wild type or normal (i.e., from corresponding healthy tissue of the same patient) amino acid and N is a changed amino acid (relative to wild type or relative to matched normal). Therefore, the neoepitope sequences contemplated herein include sequence stretches with relatively short length (e.g., 5-30 mers, more typically 8-12 mers, or 14-20 mers) wherein such stretches include the change(s) in the amino acid sequences. Where desired, additional amino acids may be placed upstream or downstream of the changed amino acid, for example, to allow for additional antigen processing in the various compartments (e.g., for proteasome processing in the cytosol, or specific protease processing in the endosomal and/or lysosomal compartments) of a cell.

Thus, it should be appreciated that a single amino acid change may be presented in numerous neoepitope sequences that include the changed amino acid, depending on the position of the changed amino acid. Advantageously, such sequence variability allows for multiple choices of neoepitopes and as such increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 8-12 amino acids, or 14-20 amino acids, with the changed amino acid preferably centrally located or otherwise situated in a manner that improves its binding to MHC. For example, where the epitope is to be presented by the MHC-I complex, a typical neoepitope length will be about 8-12 amino acids, while the typical neoepitope length for presentation via MHC-II complex will have a length of about 14-20 amino acids. As will be readily appreciated, since the position of the changed amino acid in the neoepitope may be other than central, the actual peptide sequence and with that actual topology of the neoepitope may vary considerably, and the neoepitope sequence with a desired binding affinity to the MHC-I or MHC-II presentation and/or desired protease processing will typically dictate the particular sequence.

Of course, it should be appreciated that the identification or discovery of neoepitopes may start with a variety of biological materials, including fresh biopsies, frozen, or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and in some cases protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination of the same patient. Therefore, data sets suitable for use herein include unprocessed or processed data sets, and exemplary preferred data sets include those having BAM format, SAM format, GAR format, FASTQ format, or FASTA format, as well as BAM-BAM, SAMBAM, and VCF data sets. However, it is especially preferred that the data sets are provided in BAM format or as BAMBAM diff objects as is described in US2012/0059670A1 and US2012/0066001A1. Moreover, it should be noted that the data sets are reflective of a tumor and a matched normal sample of the same patient. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor and/or metastatic site, etc. In most cases, the matched normal sample of the patient is blood, or a non-diseased tissue from the same tissue type as the tumor.

Likewise, the computational analysis of the sequence data may be performed in numerous manners. In most preferred methods, however, analysis is performed in silico by incremental location-guided synchronous alignment of tumor and normal samples as, for example, disclosed in US 2012/0059670 and US 2012/0066001 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Viewed from a different perspective, a patient- and cancer-specific in silico collection of sequences can be established that encode neoepitopes having a predetermined length of, for example, between 5 and 25 amino acids and include at least one changed amino acid. Such collection will typically include for each changed amino acid at least two, at least three, at least four, at least five, or at least six members in which the position of the changed amino acid is not identical. Such collection advantageously increases potential candidate molecules suitable for immune therapy and can then be used for further filtering (e.g., by subcellular location, transcription/expression level, MHC-I and/or II affinity, etc.) as is described in more detail below. Of course, it should be appreciated that these neoepitope sequences can be readily back-translated into the corresponding nucleic acid sequences to so generate a nucleic acid sequence that encodes the neoepitope. Most typically, but not necessarily, such back-translation will take into account the proper codon usage of the organism in which the nucleic acid is being expressed.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. Exemplary neoepitope data for these cancers can be found in International application WO 2016/172722, incorporated by reference herein.

Depending on the type and stage of the cancer, as well as the patient's immune status it should be recognized that not all of the identified neoepitopes will necessarily lead to a therapeutically equally effective reaction in a patient. Indeed, it is well known in the art that only a fraction of neoepitopes will generate an immune response. To increase likelihood of a therapeutically desirable response, the initially identified neoepitopes can be further filtered. Of course, it should be appreciated that downstream analysis need not take into account silent mutations for the purpose of the methods presented herein. However, preferred mutation analyses will provide in addition to the particular type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, at least 30%, at least 40%, or at least 50% of expression level of the corresponding matched normal sequence, thus ensuring that the (neo) epitope is at least potentially 'visible' to the immune system. Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNAseq, qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)). Consequently, it should be appreciated that the above methods will provide patient and tumor specific neoepitopes, which may be further filtered by sub-cellular location of the protein containing the neoepitope (e.g., membrane location), the expression strength (e.g., overexpressed as compared to matched normal of the same patient), etc.

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, the patient and tumor specific neoepitopes may be filtered to remove those known sequences, yielding a sequence set with a plurality of neoepitope sequences having substantially reduced false positives.

Once the desired level of filtering for the neoepitope is accomplished (e.g., neoepitope filtered by tumor versus normal, and/or expression level, and/or sub-cellular location, and/or patient specific HLA-match, and/or known variants), a further filtering step is contemplated that takes into account the gene type that is affected by the neoepitope. For example, suitable gene types include cancer driver genes, genes associated with regulation of cell division, genes associated with apoptosis, and genes associated with signal transduction. However, in especially preferred aspects, cancer driver genes are particularly preferred (which may span by function a variety of gene types, including receptor genes, signal transduction genes, transcription regulator genes, etc.). In further contemplated aspects, suitable gene types may also be known passenger genes and genes involved in metabolism.

With respect to the identification or other determination (e.g., prediction) of a gene as being a cancer driver gene, various methods and prediction algorithms are known in the art, and are deemed suitable for use herein. For example, suitable algorithms include MutsigCV (*Nature* 2014, 505 (7484):495-501), ActiveDriver (*Mol Syst Biol* 2013, 9:637), MuSiC (*Genome Res* 2012, 22(8):1589-1598), Oncodrive-Clust (*Bioinformatics* 2013, 29(18):2238-2244), OncodriveFM (*Nucleic Acids Res* 2012, 40(21):e169), OncodriveFML (*Genome Biol* 2016, 17(1):128), Tumor Suppressor and Oncogenes (TUSON) (*Cell* 2013, 155(4): 948-962), 20/20+, and oncodriveROLE (*Bioinformatics* (2014) 30 (17): i549-i555). Alternatively, or additionally, identification of cancer driver genes may also employ various sources for known cancer driver genes and their association with specific cancers. For example, the Intogen Catalog of driver mutations (2016.5; URL: www.intogen.org) contains the results of the driver analysis performed by the Cancer Genome Interpreter across 6,792 exomes of a pan-cancer cohort of 28 tumor types.

Nevertheless, despite filtering, it should be recognized that not all neoepitopes will be visible to the immune system as the neoepitopes also need to be processed where present in a larger context (e.g., within a polytope) and presented on the MHC complex of the patient. In that context, it must be appreciated that only a fraction of all neoepitopes will have sufficient affinity for presentation. Consequently, and especially in the context of immune therapy it should be apparent that neoepitopes will be more likely effective where the neoepitopes are properly processed, bound to, and presented by the MHC complexes. Viewed from another perspective, treatment success will be increased with an increasing number of neoepitopes that can be presented via the MHC complex, wherein such neoepitopes have a minimum affinity to the patient's HLA-type. Consequently, it should be appreciated that effective binding and presentation is a combined function of the sequence of the neoepitope and the particular HLA-type of a patient. Therefore, HLA-type determination of the patient tissue is typically required. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each subtype being determined to at least 2-digit or at least 4-digit depth. However, greater depth (e.g., 6 digit, 8 digit) is also contemplated.

Once the HLA-type of the patient is ascertained (using known chemistry or in silico determination), a structural solution for the HLA-type is calculated and/or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., Nucleic Acids Res. 2008 Jul. 1; 36(Web Server issue): W509-W512.). Neoepitopes with high affinity (e.g., less than 100 nM, less than 75 nM, less than 50 nM) for a previously determined HLA-type are then selected for therapy creation, along with the knowledge of the patient's MHC-I/II subtype.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types. For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, URL: www.allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in WO 2017/035392, incorporated by reference herein.

Once patient and tumor specific neoepitopes and HLA-type are identified, further computational analysis can be performed by in silico docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as is further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), RankPep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type. Moreover, where desired, binding of corresponding wild type sequences (i.e., neoepitope sequence without amino acid change) can be calculated to ensure high differential affinities. For example, especially preferred high differential affinities in MHC binding between the neoepitope and its corresponding wild type sequence are at least 2-fold, at least 5-fold, at least 10-fold, at least 100-fold, at least 500-fold, at least 1000-fold, etc.).

Binding affinity and particularly differential binding affinity may also be determined in vitro using various systems and methods. For example, antigen presenting cells of a patient or cells with matched HLA-type can be transfected with a nucleic acid (e.g., viral, plasmid, linear DNA, RNA, etc.) to express one or more neoepitopes using constructs as described in more detail below. Upon expression and antigen processing, the neoepitopes can then be identified in the MHC complex on the outside of the cell, either using specific binders to the neoepitope or using a cell based system (e.g., PBMC of the patient) in which T cell activation or cytotoxic NK cell activity can be observed in vitro. Neoepitopes with differential activity (elicit a stronger signal or immune response as compared to the corresponding wild type epitope) will then be selected for therapy creation.

Recombinant Nucleic Acids/Polytopes

Upon proper selection of filtered neoepitopes (or tumor associated antigens or tumor specific antigens), a recombinant nucleic acid can be constructed that forms the basis of all downstream vaccine compositions. Most typically, the desired nucleic acid sequences (for expression from virus infected cells) are under the control of appropriate regulatory elements well known in the art. As will also be readily appreciated, the choice of regulatory elements will be dictated by the system in which the recombinant nucleic acid is to be expressed. Therefore, suitable regulatory elements include constitutively active or inducible bacterial and yeast promoters (and associated inducer and/or repressor sequences where desired), as well as eukaryotic (and preferably mammal/human) promoter sequences. For example, where the recombinant nucleic acid is used in a DNA vaccine, suitable promoter elements include constitutive strong promoters (e.g., SV40, CMV, UBC, EF1A, PGK, CAGG promoter). On the other hand, where the recombinant nucleic acid is part of a viral expression vector, contemplated promoters also include inducible promoters, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

Similarly, where the recombinant nucleic acid is used to generate a bacterial and/or yeast vaccine in which the bacterium or yeast expresses the neoepitope or other therapeutic antigen, suitable promoters include strong constitutive or inducible bacterial and yeast promoters. For example, suitable bacterial promoters for expression of antigens/a polytope include the T7 promoter, the Tac promoter, the BAD promoter, the Trc promoter, etc. Likewise, yeast contemplated yeast promoters include the AOX1 promoter, the GAL promoter, the GDS promoter, the ADH promoter, etc.

In this context, it should be appreciated that the inventors have discovered that the manner of neoepitope arrangement and rational-designed trafficking of the neoepitopes can have a substantial impact on the efficacy of various immune therapeutic compositions as is further described in more detail below. For example, single neoepitopes can be expressed individually from the respective recombinant constructs that are delivered as a single plasmid, viral expression construct, etc. Alternatively, multiple neoepitopes can be separately expressed from individual promoters to form individual mRNA that are then individually translated into the respective neoepitopes, or from a single mRNA comprising individual translation starting points for each neoepitope sequence (e.g., using 2A or IRES signals). Notably, while such arrangements are generally thought to allow for controlled delivery of proper neoepitope peptide, efficacy of such expression systems has been less than desirable (data not shown).

In contrast, where multiple neoepitopes were expressed from a single transcript to so form a single transcript that is then translated into a single polytope (i.e., polypeptide with a series of concatemerically linked neoepitopes, optionally with intervening linker sequences) expression, processing, and antigen presentation was found to be effective. Notably, the expression of polytopes requires processing by the appropriate proteases (e.g., proteasome, endosomal proteases, lysosomal proteases) within a cell to yield the neoepitope sequences, and polytopes led to improved antigen processing and presentation for most neoepitopes as compared to expression of individual neoepitopes, particularly where the individual neoepitopes had a relatively short length (e.g., less than 25 amino acids; results not shown). Moreover, such approach also allows rational design of protease sensitive sequence motifs between the neoepitope peptide sequences to so assure or avoid processing by specific proteases as the proteasome, endosomal proteases, and lysosomal proteases have distinct cleavage preferences. Therefore, polytopes may be designed that include not only linker sequences to spatially separate neoepitopes, but also sequence portions (e.g., between 3-15 amino acids) that will be preferentially cleaved by a specific protease.

Therefore, the inventors contemplate recombinant nucleic acids and expression vectors (e.g., viral expression vectors) that comprise a nucleic acid segment that encodes a polytope wherein the polytope is operably coupled to a desired promoter element, and wherein individual neoepitopes are optionally separated by a linker and/or protease cleavage or recognition sequence. For example, FIG. 1 exemplarily illustrates various contemplated arrangements for neoepitopes for expression from an adenoviral expression system (here: AdV5, with deletion of E1 and E2b genes). Here, Construct 1 exemplarily illustrates a neoepitope arrangement that comprises eight neoepitopes ('minigene') with a total length of 15 amino acids in concatemeric series without intervening linker sequences, while Construct 2 shows the arrangement of Construct 1 but with inclusion of nine amino acid linkers between each neoepitope sequence. Of course, and as already noted above, it should be recognized that the exact length of the neoepitope sequence is not limited to 15 amino acids, and that the exact length may vary considerably. However, in most cases, where neoepitope sequences of between 8-12 amino acids are flanked by additional amino acids, the total length will typically not exceed 25 amino acids, or 30 amino acids, or 50 amino acids. Likewise, it should be noted that while FIG. 1 denotes G-S linkers, various other linker sequences are also suitable for use herein. Such relatively short neoepitopes are especially beneficial where presentation of the neoepitope is intended to be via the MHC-I complex.

In this context, it should be appreciated that suitable linker sequences will provide steric flexibility and separation of two adjacent neoepitopes. However, care must be taken to as to not choose amino acids for the linker that could be immunogenic/form an epitope that is already present in a patient. Consequently, it is generally preferred that the polytope construct is filtered once more for the presence of epitopes that could be found in a patient (e.g., as part of normal sequence or due to SNP or other sequence variation). Such filtering will apply the same technology and criteria as already discussed above.

Similarly, Construct 3 exemplarily illustrates a neoepitope arrangement that includes eight neoepitopes in concatemeric series without intervening linker sequences, and Construct 4 shows the arrangement of Construct 3 with inclusion of nine amino acid linkers between each neoepitope sequence. As noted above, it should be recognized that the exact length of such neoepitope sequences is not limited to 25 amino acids, and that the exact length may vary considerably. However, in most cases, where neoepitope sequences of between 14-20 amino acids are flanked by additional amino acids, the total length will typically not exceed 30 amino acids, or 45 amino acids, or 60 amino acids. Likewise, it should be noted that while FIG. 1 denotes G-S linkers for these constructs, various other linker sequences are also suitable for use herein. Such relatively long neoepitopes are especially beneficial where presentation of the neoepitope is intended to be via the MHC-II complex.

In this example, it should be appreciated that the 15-aa minigenes are MHC Class I targeted tumor mutations selected with 7 amino acids of native sequence on either side, and that the 25-aa minigenes are MHC Class II targeted tumor mutations selected with 12 amino acids of native sequence on either side. The exemplary 9 amino acid linkers are deemed to have sufficient length such that "unnatural" MHC Class I epitopes will not form between adjacent minigenes. Polytope sequences tended to be processed and presented more efficiently than single neoepitopes (data not shown), and addition of amino acids beyond 12 amino acids for MHC-I presentation and addition of amino acids beyond 20 amino acids for MHC-I presentation appeared to allow for somewhat improved protease processing.

To maximize the likelihood that customized protein sequences remain intracellular for processing and presentation by the HLA complex, neoepitope sequences may be arranged in a manner to minimize hydrophobic sequences that may direct trafficking to the cell membrane or into the extracellular space. Most preferably, hydrophobic sequence or signal peptide detection is done either by comparison of sequences to a weight matrix (see e.g., *Nucleic Acids Res.* 1986 Jun. 11; 14(11): 4683-4690) or by using neural networks trained on peptides that contain signal sequences (see e.g., *Journal of Molecular Biology* 2004, Volume 338, Issue 5, 1027-1036). FIG. 2 depicts an exemplary scheme of arrangement selection in which a plurality of polytope sequences are analyzed. Here, all positional permutations of all neoepitopes are calculated to produce a collection of arrangements. This collection is then processed through a weight matrix and/or neural network prediction to generate a score representing the likelihood of presence and/or strength of hydrophobic sequences or signal peptides. All positional permutations are then ranked by score, and the permutation(s) with a score below a predetermined threshold or lowest score for likelihood of presence and/or strength of hydrophobic sequences or signal peptides is/are used to construct a customized neoepitope expression cassette.

With respect to the total number of neoepitope sequences in a polytope it is generally preferred that the polytope comprise at least two, or at least three, or at least five, or at least eight, or at least ten neoepitope sequences. Indeed, the payload capacity of the host organism of the recombinant DNA is generally contemplated the limiting factor, along with the availability of filtered and appropriate neoepitopes. For example, adenoviral expression vectors, and particularly Adv5 are especially preferred as such vectors can accommodate up to 14 kb in recombinant payload. Likewise, bacterial and yeast systems can accommodate even larger payloads, typically in excess of 50 kb. On the other hand, where the recombinant DNA is used in a DNA vaccine, suitable sizes will typically range between 5 kb and 20 kb.

In still further contemplated aspects of the inventive subject matter, it should be noted that the neoepitopes/polytopes can be directed towards a specific sub-cellular compartment (e.g., cytosol, endosome, lysosome), and with that, towards a particular MHC presentation type. Such directed expression, processing, and presentation is particularly advantageous as contemplated compositions may be prepared that direct an immune response towards a $CD8^+$ type response (where the polytope is directed to the cytoplasmic space) or towards a $CD4^+$ type response (where the polytope is directed to the endosomal/lysosomal compartment). Moreover, it should be recognized that polytopes that would ordinarily be presented via the MHC-I pathway can be presented via the MHC-II pathway (and thereby mimic cross-presentation of neoepitopes). Therefore, it should be appreciated that neoepitope and polytope sequences may be designed and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane.

Moreover, it is contemplated that proteolytic degradation of the polytope can also be enhanced using various methods, and especially contemplated methods include addition of a cleavable or non-cleavable ubiquitin moiety to the N-terminus, and/or placement of one or more destabilizing amino acids (e.g., N, K, C, F, E, R, Q) to the N-terminus of the polytope where the presentation is directed towards MHC-I. On the other hand, where presentation is directed towards MHC-II, cleavage sites for particular endosomal or lysosomal proteases can be engineered into the polytope to so facilitate of promote antigen processing.

Therefore, in contemplated aspects of the inventive subject matter, signal and/or leader peptides may be used for trafficking neoepitopes and/or polytopes to the endosomal and lysosomal compartment, or for retention in the cytoplasmic space. For example, where the polytope is to be exported to the endosomal and lysosomal compartment, a leader peptide such as the CD1b leader peptide may be employed to sequester the (nascent) protein from the cytoplasm. Additionally, or alternatively, targeting presequences and/or targeting peptides can be employed. The presequences of the targeting peptide may be added to the N-terminus and/or C-terminus and typically comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus.

In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531). For example, lysosomal targeting can be achieved using a LAMP1-TM (transmembrane) sequence, while recycling endosomes can be targeted via the CD1a tail targeting sequence, and sorting endosomes can be targeted via the CD1c tail targeting sequence as is shown in more detail further below.

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein such that the protein is retained in the cell facing the cytosol. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

In still further contemplated aspects of the inventive subject matter, the polytope may also comprise one or more transmembrane segments that will direct the neoepitope after processing to the outside of the cell membrane to so be visible to immune competent cells. There are numerous transmembrane domains known in the art, and all of those are deemed suitable for use herein, including those having a single alpha helix, multiple alpha helices, alpha/beta barrels, etc. For example, contemplated transmembrane domains can comprise comprises the transmembrane region(s) of the alpha, beta, or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, or PAG/Cbp. Where a fusion protein is desired, it is contemplated that the recombinant chimeric gene has a first portion that encodes the transmembrane region(s), wherein the first portion is cloned in frame with a second portion that encodes the inhibitory protein. It should be noted that such presentation will not result in MHC-complex presentation and as such provides a neoepitope presentation independent of MHC/T-cell receptor interaction, which may further open additional avenues for immune recognition and trigger antibody production against the neoepitopes.

Alternatively, or additionally, the polytope may also be designed to include signal sequences for protein export of one or more neoepitope to thereby force a transfected cell to produce and secrete one or more neoepitopes. For example, the SPARC leader sequence may be added to a neoepitope or polytope sequence, leading to in vivo secretion of the neoepitope or polytope sequence into the extracellular space. Advantageously, such secreted neoepitopes or polytopes are then taken up by immune competent cells, and especially antigen presenting cells and dendritic cells that in turn process and display the neoepitopes, typically via MHC-II pathways.

In still further contemplated aspects, the polytope may also be designed as a chimeric polytope that includes at least a portion of, and more typically an entire tumor associated antigen (e.g., CEA, PSMA, PSA, MUC1, AFP, MAGE, HER2, HCC1, p62, p90, etc.). Most notably, tumor associated antigens are generally processed and presented via the MHC-II pathway. Therefore, instead of using compartment specific signal sequences and/or leader sequences, the processing mechanism for tumor associated antigens can be employed for MHC-II targeting.

Therefore, it should be appreciated that immune therapeutic compositions may be prepared that can deliver one or more neoepitopes to various sub-cellular locations, and with that generate distinct immune responses. For example, Prior Art FIG. 3 schematically illustrates a scenario where the polytope is predominantly processed in the proteasome of the cytoplasm and presented via the MHC-I complex, which is recognized by the T-cell receptor of a $CD8^+$ T-cell. Consequently, targeting polytope processing to the cytosolic compartment will skew the immune response towards a $CD8^+$ type response. On the other hand, Prior Art FIG. 4 schematically illustrates a scenario where the polytope is predominantly processed in the endosomal compartment and presented via the MHC-II complex, which is recognized by the T-cell receptor of a $CD4^+$ T-cell. Consequently, targeting polytope processing to the endosomal or lysosomal compartment will skew the immune response towards a $CD4^+$ type response. In addition, it should be appreciated that such targeting methods allow for specific delivery of a polytope or neoepitope peptide to an MHC subtype having the highest affinity with the peptide, even if that peptide would otherwise not be presented by that MHC subtype. Therefore, and as noted earlier, peptides for MHC-I presentation will generally be designed to have 8-12 amino acids (plus additional amino acids for flexibility in protease processing), while peptides for MHC-II presentation will be designed to have 14-20 amino acids (plus additional amino acids for flexibility in protease processing). In the examples below, further amino acids were added to allow for processing flexibility in the cytoplasmic, proteasome, or endosomal compartments.

In still further contemplated aspects of the inventive subject matter, it should be noted that trafficking modes of the neoepitope or polytope may be combined to accommodate one or more specific purposes. For example, sequential administration of the same neoepitopes or polytope with different targeting may be particularly beneficial in a prime-boost regimen where in a first administration the patient in inoculated with a recombinant virus to infect the patients cells, leading to antigen expression, processing, and presentation (e.g., predominantly MHC-I presentation) that will result in a first immune response originating from within a cell. The second administration of the same neoepitopes bound to albumin may then be employed as a boost as the so delivered protein is taken up by antigen presenting cells, leading in most cases to a distinct antigen presentation (e.g., predominantly MHC-II presentation). Where the same neoepitopes or polytope is trafficked to the cell surface for cell surface bound MHC-independent presentation, ADCC responses or NK mediated cell killing may be promoted. In still further contemplated aspects, and as illustrated in the examples below, immunogenicity of neoepitopes may be enhanced by cross presentation or MHC-II directed presentation. Notably, as cancer cell neoepitopes are typically internally generated and recycled, and with that preferentially presented via the MHC-I system, contemplated systems and methods now allow for presentation of such neoepitopes via MHC-II, which may be more immunogenic as is shown in more detail below. In addition, multiple and distinct trafficking of the same neoepitopes or polytopes may advantageously increase or supplement an immune response due to the stimulation of various and distinct components of the cellular and humoral immune system.

Of course, it should be appreciated that multiple and distinct trafficking of the same neoepitopes or polytopes may be achieved in numerous manners. For example, differently trafficked neoepitopes or polytopes may be administered separately using the same (e.g., viral expression vector) or different (e.g., viral expression vector and albumin bound) modality. Similarly, and especially where the therapeutic agent is an expression system (e.g., viral or bacterial), the recombinant nucleic acid may include two distinct portions that encode the same, albeit differently trafficked neoepitope or polytope (e.g., first portion trafficked to first location (e.g., cytosol or endosomal or lysosomal), second portion trafficked to a second, distinct location (e.g., cytosol or endosomal or lysosomal, secreted, membrane bound)). Likewise, a first administration may employ viral delivery of cytoplasm targeted neoepitopes or polytope, while a second administration is typically at least a day, two days, four days, a week, or two weeks after the first administration and may employ viral delivery of endosomal or lysosomal targeted or secreted neoepitopes or polytope.

In addition, it should be appreciated that where the recombinant nucleic acid is used in a DNA, bacterial, or yeast vaccine, the manner of uptake of these modalities will at least partially dictate intracellular trafficking. Most typically, DNA, bacterial, or yeast vaccines are taken up by endocytotic or related processes and as such will be preferentially routed to the endosomal or lysosomal compartments. Such routing can be further enhanced (at least in the case of DNA vaccines) using appropriate trafficking signals as already described above or counteracted by use of a cytoplasmic retention sequence. However, other embodiments, it should be appreciated that polytopes delivered via DNA, bacterial, or yeast vaccines need not have a trafficking signal at all. Such polytopes will then preferentially processed/presented via the MHC-II system.

Additionally, it is contemplated that the expression construct, and especially the recombinant viral expression vector or DNA plasmid for a DNA vaccine, may further encode at least one, more typically at least two, even more typically at least three, and most typically at least four co-stimulatory molecules to enhance the interaction between the infected cells (e.g., antigen presenting cells) and T-cells. For example, suitable co-stimulatory molecules include CD80, CD86, CD30, CD40, CD30L, CD40L, ICOS-L, B7-H3, B7-H4, CD70, OX40L, 4-1BBL, while other stimulatory molecules with less defined (or understood) mechanism of action include GITR-L, TIM-3, TIM-4, CD48, CD58, TL1A, ICAM-1, LFA3, and members of the SLAM family. However, especially preferred molecules for coordinated expression with the cancer-associated sequences include CD80 (B7-1), CD86 (B7-2), CD54 (ICAM-1) and CD11 (LFA-1). In addition to co-stimulatory molecules, the inventors also contemplate that one or more cytokines or cytokine analogs may be expressed from the recombinant nucleic acid, and especially preferred cytokines and cytokine analogs include IL-2, IL-15, and IL-a5 superagonist (ALT-803). Moreover, it should be appreciated that expression of the co-stimulatory molecules and/or cytokines will preferably be coordinated such that the neoepitopes or polytope are expressed contemporaneously with one or more co-stimulatory molecules and/or cytokines. Thus, it is typically contemplated that the co-stimulatory molecules and/or cytokines are produced from a single transcript (which may or may not include the sequence portion encoding the polytope), for example, using an internal ribosome entry site or 2A sequence, or from multiple transcripts.

Likewise, it is contemplated that the viral vector may also include a sequence portion that encodes one or more peptide ligands that bind to a checkpoint receptor. Most typically, binding will inhibit or at least reduce signaling via the receptor, and particularly contemplated receptors include CTLA-4 (especially for CD8$^+$ cells), PD-1 (especially for CD4$^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors. Once more, it should be appreciated that expression of the peptide molecules will preferably be coordinated such that the neoepitopes or polytope are expressed contemporaneously with one or more of the peptide ligands. Thus, it is typically contemplated that the peptide ligands are produced from a single transcript (which may or may not include the sequence portion encoding the polytope), for example, using an internal ribosome entry site or 2A sequence, or from multiple transcripts.

It should be appreciated that all of the above noted co-stimulatory genes and genes coding for inhibitory proteins that interfere with/down-regulate checkpoint inhibition are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

Consequently, contemplated expression constructs will preferably include a sequence portion that encodes one or more polytopes, wherein at least one, and more typically at least two, or all of the polytopes will include a trafficking signal that will result in preferential trafficking of the polytope to at least one, and more typically at least two different sub-cellular locations.

For example, the first polytope may be directed towards the cytoplasm (and may include an additional cleavable or non-cleavable ubiquitin) while the second polytope may be directed towards the endosomal or lysosomal compartment. Or the first polytope may be directed towards the endosomal or lysosomal compartment while the second polytope may be directed towards the cell membrane or be secreted. As noted before, the encoded polytope will comprise at least two neoepitopes, optionally separated by a linker. Moreover, such contemplated expression constructs will also include a sequence portion that encodes one or more co-stimulatory molecules and/or cytokines, and may also include one or more inhibitory proteins that interfere with/down-regulate checkpoint inhibition. Most typically, the expression construct will also include regulatory sequences operably coupled to the above sequence portions to drive contemporaneous expression of the polytope and the co-stimulatory molecules, cytokines, and/or inhibitory proteins. Suitable promoter elements are known in the art, and especially preferred promoters include the constitutive and inducible promoters discussed above.

Vaccine Compositions

Upon identification of desired neoepitopes, one or more immune therapeutic agents may be prepared using the sequence information of the neoepitopes, preferably configured as a polytope as described above. Preferably, the immune therapeutic agents include at least two of a DNA vaccine that includes a recombinant nucleic acid that encodes at least one antigen (and more typically at least two, three, four, or more antigens) that is present in the tumor, a bacterial vaccine in which a bacterium expresses at least one antigen (and more typically at least two, three, four, or more antigens) that is present in the tumor, a yeast vaccine in which a bacterium expresses at least one antigen (and more typically at least two, three, four, or more antigens) that is present in the tumor, and a viral vaccine that comprises a viral expression vector that includes a recombinant nucleic acid that encodes at least one antigen (and more typically at least two, three, four, or more antigens) that is present in the tumor.

With respect to recombinant nucleic acids for expression and DNA vaccination systems it is contemplated that the recombinant nucleic acid may be an RNA or a DNA. With respect to the use of RNA, DNA, or other recombinant vectors that lead to the expression of the tumor antigens and/or neoepitopes, especially contemplated nucleic acids include plasmid vectors that may be supercoiled, coiled, relaxed, or even linearized. For example, and among other suitable choices, contemplated vectors include vectors used in cloning one or more sequence portions used in the preparation of the viral expression vector. Thus, especially contemplated vectors include transfer or shuttle vectors, and various general cloning vectors (e.g., having a bacterial origin of replication, a selection marker (e.g., antibiotic resistance or fluorescent protein), and a multiple cloning site). Suitable vectors are well known in the art and are typically based on a plasmid with replicative capability in bacteria for cloning and production of substantial quantities. Proper vector selection may further be determined by its particular use (e.g., shuttle vector for adenovirus, lentivirus, or baculovirus, etc.), choice of inducible or constitutive promoter (e.g., CMV, UbC), choice of permanent or transient expression, manner of transfection (e.g., lipofection, electroporation, etc.), capacity for the recombinant payload, etc.

It should still further be noted that plasmids may be methylated or unmethylated, which may be controlled by directed enzymatic in vitro reactions or more simply by in vivo replication of the plasmid in a methylation competent or a methylation deficient host. Still further, it should be appreciated that the plasmid may further have one or more nucleic acid portions that are known to trigger an innate immune response (e.g., CpG islands or other sequence motifs that interact with Toll-like receptors such as TLR3, TLR 7, TLR 8, TLR 9, RIG-I-like receptors, STING, and/or intracellular DNA sensors such as NLRP3/CIAS1).

Most typically, and as already noted above, contemplated plasmids and other nucleic acids will include one or more sequence elements that encode the preferably patient- and tumor specific neoepitopes or the polytope, most preferably operably coupled to regulatory elements that permit or drive the expression of the neoepitope or polytope in eukaryotic cells, and especially mammalian cells (e.g., human). Moreover, it should be noted that the neoepitope or polytope may include the trafficking signals for routing the peptide to the desired sub-cellular location as also discussed herein. Therefore, especially preferred plasmids include plasmids used in the production of a viral expression vector, and as such will already include all regulatory elements needed for expression and/or trafficking of the polytope in a mammalian cell. Thus cloning vectors and shuttle vectors are especially preferred.

As will be appreciated, plasmids contemplated herein may be administered in numerous manners known in the art, and suitable delivery modes include injection (intramuscular, intravenous, intradermal), delivery via gene gun or other ballistic transfer, or by liposome mediated transfer. Therefore, contemplated compositions will particularly include injectable formulations comprising nucleic acid lipoplexes and other DNA-lipid or DNA lipoprotein complexes. Advantageously, the choice of delivery may be used to polarize the immune response towards either Th1 (via injection using saline) or Th2 (via gene gun delivery) response as described elsewhere (see e.g., J Immunol Mar. 1, 1997, 158 (5) 2278-2284). In especially preferred aspects, vaccination with DNA will preferably be performed by intravenous injection as is discussed in more detail below, however, other routes (including intramuscular, intradermal, subcutaneous, intra-arterial) are also deemed suitable for use herein, while administration of the viral expression vector (typically using a recombinant virus) will preferably be performed by subcutaneous injection.

Without wishing to be bound by any specific theory or hypothesis, it is believed that the use of plasmids and other 'naked' nucleic acids (e.g., linear DNA RNA) will provide a first opportunity to generate an immune response that is both non-specific and specific to the patient's neoepitope. Non-specific reactions are deemed to arise from a component of the innate immune response against foreign nucleic acids, for example, where the nucleic acid is unmethylated (e.g., via TLR-9). In addition, expression of the neoepitope or polytope in the cells transfected with the plasmid will also promote adaptive immune responses.

In addition to the use of DNA vaccination, contemplated plasmids may also be used in the production of a viral or yeast expression vector that can be employed to produce a recombinant virus (e.g., lentivirus, adenovirus) or yeast for subsequent administration to the patient. Where the plasmid is used for production of a yeast or viral expression system, all known expression systems are deemed suitable for use herein. For example, suitable materials and protocols can be found in the non-profit plasmid repository Addgene or in the AdEasy adenoviral vector system (commercially available from Agilent). Similarly, there are numerous yeast expression systems known in the art and all of those are deemed suitable for use herein. Such second administration can be viewed as a boost regimen to the DNA vaccination as the mammal was already primed by the plasmid vector. Of course, it should be recognized that where the prime vaccination was a DNA vaccination with a plasmid as described above, the boost may use various alternate formats, including a vaccination with the neoepitope peptides or polytope using more conventional vaccine formulations. Further suitable DNA vaccines are described, for example, in US 2014/0178438.

With respect to bacterial expression and vaccination systems it is contemplated that all bacterial strains are deemed suitable, and especially include species from Salmonella, Clostridium, Bacillus, Lactobacillus, Bifidobacterium, etc., particularly where such strains are non-pathogenic, genetically engineered to have reduced toxicity, and/or were irradiated prior to administration. Historically, most bacteria strains have been deemed unsuitable for introducing into the blood stream or transplanting into an organ or tissue, as most bacteria express lipopolysaccharides that trigger immune responses and cause endotoxic responses, which can lead potentially fatal sepsis (e.g., CD-14 mediated sepsis) in patients. Thus, one especially preferred bacterial strain is based on a genetically modified bacterium which expresses endotoxins at a level low enough not to cause an endotoxic response in human cells and/or insufficient to induce a CD-14 mediated sepsis when introduced to the human body.

One preferred bacterial species is a genetically modified Escherichia coli (E. coli) strain due to its fast growth (e.g., one complete cell cycle in 20 min) and availability of many strains optimized for protein overexpression upon induction (e.g., lac promoter induction with IPTG, etc.). Most typically, the genetic modification will reduce or remove production of most lipopolysaccharide components leading to endotoxic response. For example, one exemplary bacteria strain with modified lipopolysaccharide synthesis includes ClearColi® BL21(DE3) electrocompetent cells. This bacterial strain is BL21 with a genotype F-ompT hsdSB (rB– mB–) gal dcm lon λ(DE3) [lacI lacUV5-T7 gene 1 ind1 sam7 nin5]) msbA148 ΔgutQΔkdsD ΔlpxLΔlpxMΔpagPΔlpxPAeptA. In this context, it should be appreciated that several specific deletion mutations (ΔgutQ ΔkdsD ΔlpxL ΔlpxMΔpagPΔlpxPAeptA) encode the modification of LPS to Lipid $IV_A$, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-κB and production of proinflammatory cytokines. Lipid $IV_A$, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria.

Alternatively, the inventors also contemplate that the patient's own endosymbiotic bacteria can be used as a vehicle to express human disease-related antigens in vivo to elicit immune response at least locally. As used herein, the patient's endosymbiotic bacteria refers bacteria residing in the patient's body regardless of the patient's health condition without invoking any substantial immune response. Thus, it is contemplated that the patient's endosymbiotic bacteria is a normal flora of the patient. For example, the patient's endosymbiotic bacteria may include E. coli or

*Streptococcus* that can be commonly found in human intestine or stomach. In these embodiments, patient's own endosymbiotic bacteria can be obtained from the patient's biopsy samples from a portion of intestine, stomach, oral mucosa, or conjunctiva, or in fecal samples. The patient's endosymbiotic bacteria can then be cultured in vitro and transfected with nucleotides encoding human disease-related antigen(s).

Therefore, it should be appreciated that the bacteria used in the methods presented herein may be from a strain that produces LPS, or that are genetically engineered to have reduced or abrogated expression of one or more enzymes leading to the formation of LPS that is recognized by a TLR, and particularly TLR4. Most typically, such bacteria will be genetically modified to express in an inducible manner at least one human disease-related antigen for immunotherapy. Among other options, induction of expression may be done with synthetic compounds that are not ordinarily found in a mammal (e.g., IPTG, substituted benzenes, cyclohexanone-related compounds) or with compounds that naturally occur in a mammal (e.g., sugars (including 1-arabinose, 1-rhamnose, xylose, and sucrose), ε-caprolactam, propionate, or peptides), or induction may be under the control of one or more environmental factors (e.g., temperature or oxygen sensitive promoter).

Contemplated recombinant nucleic acids that encode the tumor antigens or the polytope can be inserted into an expression vector that has a specific promoter (e.g., inducible promoter, etc.) to drive expression of the antigens or polytope in the bacterium. The vector is then transfected into the bacterium (e.g., ClearColi® BL21(DE3) electrocompetent cells) following conventional methods, or any other type of competent bacterium expressing low endotoxin level that is insufficient to induce a CD-14 mediated sepsis when introduced to the human body), or to patient's own endosymbiotic bacterium that is optionally cultured in vitro before transformation as described above.

With respect to yeast expression and vaccination systems it is contemplated that all known yeast strains are deemed suitable for use herein. However, it is preferred that the yeast is a recombinant *Saccharomyces* train that is genetically modified with a nucleic acid construct as discussed above that leads to expression of at least one of the tumor antigens to thereby initiate an immune response against the tumor. Nevertheless, it is noted that any yeast strain can be used to produce a yeast vehicle of the present invention. Yeasts are unicellular microorganisms that belong to one of three classes: Ascomycetes, Basidiomycetes and Fungi Imperfecti. One consideration for the selection of a type of yeast for use as an immune modulator is the pathogenicity of the yeast. In preferred embodiments, the yeast is a non-pathogenic strain such as *Saccharomyces cerevisiae* as non-pathogenic yeast strains minimize any adverse effects to the individual to whom the yeast vehicle is administered. However, pathogenic yeast may also be used if the pathogenicity of the yeast can be negated using pharmaceutical intervention.

For example, suitable genera of yeast strains include *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in a preferred aspect, *Saccharomyces* is used. Species of yeast strains that may be used in the invention include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha,* *Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*.

It should further be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful due to it being relatively easy to manipulate and being "Generally Recognized As Safe" or "GRAS" for use as food additives (GRAS, FDA proposed Rule 62FR18938, Apr. 17, 1997). Therefore, the inventors particularly contemplate a yeast strain that is capable of replicating plasmids to a particularly high copy number, such as a *S. cerevisiae* cir strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

Expression of contemplated antigens/neoepitopes in yeast can be accomplished using techniques known to those skilled in the art. Most typically, a nucleic acid molecule encoding at least neoepitope or other protein is inserted into an expression vector such manner that the nucleic acid molecule is operatively linked to a transcription control sequence to be capable of effecting either constitutive or regulated expression of the nucleic acid molecule when transformed into a host yeast cell. As will be readily appreciated, nucleic acid molecules encoding one or more antigens and/or other proteins can be on one or more expression vectors operatively linked to one or more expression control sequences. Particularly important expression control sequences are those which control transcription initiation, such as promoter and upstream activation sequences.

Any suitable yeast promoter can be used in the present invention and a variety of such promoters are known to those skilled in the art and have generally be discussed above. Promoters for expression in *Saccharomyces cerevisiae* include promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SECT) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the alpha-factor, GAPDH, and CYC1 genes. Transcription control sequences to express genes in methyltrophic yeast include the transcription control regions of the genes encoding alcohol oxidase and formate dehydrogenase.

Likewise, transfection of a nucleic acid molecule into a yeast cell according to the present invention can be accomplished by any method by which a nucleic acid molecule administered into the cell and includes diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins. Further exemplary yeast expression systems, methods, and conditions suitable for use herein are described in US20100196411A1, US2017/0246276, or US 2017/0224794, and US 2012/0107347.

With respect to viral expression and vaccination systems it is contemplated that all therapeutic recombinant viral expression systems are deemed suitable for use herein so long as such viruses are capable to lead to expression of the recombinant payload in an infected cell. For example, suitable viruses include genetically modified alphaviruses, adenoviruses, adeno-associated viruses, herpes viruses, lentiviruses, etc. However, adenoviruses are particularly preferred. For example, genetically modified adenoviruses are preferred that are suitable not only for multiple vaccinations but also vaccinations in individuals with preexisting immunity to the adenovirus (see e.g., WO 2009/006479 and WO 2014/031178), typically achieved by deletion of the E2b gene and other late proteins to reduce immunogenicity. Moreover, due to these specific deletions, such genetically modified viruses were replication deficient and allowed for relatively large recombinant cargo. For example, WO 2014/031178 describes the use of such genetically modified viruses to express CEA (colorectal embryonic antigen) to provide an immune reaction against colon cancer. Moreover, relatively high titers of recombinant viruses can be achieved using genetically modified human 293 cells as has been reported (e.g., *J Virol.* 1998 February; 72(2): 926-933).

Regardless of the type of recombinant virus it is contemplated that the virus may be used to infect patient (or non-patient) cells ex vivo or in vivo. For example, the virus may be injected subcutaneously or intravenously, or may be administered intranasaly or via inhalation to so infect the patients cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells.

As noted above, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

Alternatively, or additionally, it should be recognized that the antigen/neoepitope or polytope may also be administered as peptide, optionally bound to a carrier protein to so act as a peptide vaccine. Among other suitable carrier proteins, human albumin or lactoferrin are particularly preferred. Such carrier proteins may be in native conformation, or pretreated to form nanoparticles with exposed hydrophobic domains (see e.g., *Adv Protein Chem Struct Biol.* 2015; 98:121-43) to which the neoepitope or polytope can be coupled. Most typically, coupling of the neoepitope or polytope to the carrier protein will be non-covalent. Similar to the secreted neoepitopes or polytopes, carrier protein-bound neoepitopes or polytopes will be taken up by the immune competent cells, and especially antigen presenting cells and dendritic cells that in turn process and display the neoepitopes, typically via MHC-II pathways.

Formulations

Where the vaccine is a viral vaccine (e.g., an adenovirus, and especially AdV with E1 and E2b deleted), it is contemplated that the recombinant viruses may then be individually or in combination used as a therapeutic vaccine in a pharmaceutical composition, typically formulated as a sterile injectable composition with a virus titer of between $10^6$-$10^{13}$ virus particles, and more typically between $10^9$-$10^{12}$ virus particles per dosage unit. Alternatively, virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody.

Similarly, where the vaccine is a bacterial or yeast vaccine, the bacteria or yeast cells are preferably irradiated prior to administration to prevent further propagation. Most typically, administration is as a therapeutic vaccine in a pharmaceutical composition, typically formulated as a sterile injectable composition with a cell titer of between $10^6$-$10^9$ cells, and more typically between $10^8$-$10^{11}$ cells per dosage unit. Most preferably, the vaccine formulation is administered intramuscularly, subcutaneously, or intratumorally. DNA vaccines will typically be administered as is well known in the art, preferably by intravenous injection of the DNA in a buffered solution as a pharmaceutical composition. While not limiting to the inventive subject matter, the total dose of DNA per administration will typically be in the range of 0.1 mcg to several 10 mg, or between 10 mcg to several 1,000 mcg.

Where desired, additional therapeutic modalities may be employed which may be neoepitope based (e.g., synthetic antibodies against neoepitopes as described in WO 2016/172722), alone or in combination with autologous or allogenic NK cells, and especially haNK cells or taNK cells (e.g., both commercially available from NantKwest, 9920 Jefferson Blvd. Culver City, CA 90232). Where haNK or taNK cells are employed, it is particularly preferred that the haNK cell carries a recombinant antibody on the CD16 variant that binds to a neoepitope of the treated patient, and where taNK cells are employed it is preferred that the chimeric antigen receptor of the taNK cell binds to a neoepitope of the treated patient. The additional treatment modality may also be independent of neoepitopes, and especially preferred modalities include cell-based therapeutics such as activated NK cells (e.g., aNK cells, commercially available from NantKwest, 9920 Jefferson Blvd. Culver City, CA 90232), and non cell-based therapeutics such as chemotherapy and/or radiation. In still further contemplated aspects, immune stimulatory cytokines, and especially IL-2, IL15, and IL-21 may be administered, alone or in combination with one or more checkpoint inhibitors (e.g., ipilimumab, nivolumab, etc.). Similarly, it is still further contemplated that additional pharmaceutical intervention may include administration of one or more drugs that inhibit immune suppressive cells, and especially MDSCs Tregs, and M2 macrophages. Thus, suitable drugs include IL-8 or interferon-γ inhibitors or antibodies binding IL-8 or interferon-γ, as well as drugs that deactivate MDSCs (e.g., NO inhibitors, arginase inhibitors, ROS inhibitors), that block development of or differentiation of cells to MDSCs (e.g., IL-12, VEGF-inhibitors, bisphosphonates), or agents that are toxic to MDSCs (e.g., gemcitabine, cisplatin, 5-FU). Likewise, drugs like cyclophosphamide, daclizumab, and anti-GITR or anti-OX40 antibodies may be used to inhibit Tregs.

Protocols

Therefore, the inventors contemplate various exemplary strategies for treatment with the compositions contemplated herein. Most typically, treatments will include at least two, or at least three distinct vaccine modalities that are administered in a sequential fashion. For example in some embodiments, the initial administration will be a DNA vaccine that is followed by administration of a bacterial vaccine. The bacterial vaccine may optionally be followed by a yeast vaccine. Following the bacterial or yeast vaccine administration may then be a viral vaccine administration. In another example, the initial administration will be a bacterial vaccine that is optionally followed by administration of a yeast vaccine. Following the bacterial or yeast vaccine administration may then be a viral vaccine administration. In still another example, the initial administration will be a DNA vaccine, which is followed by a viral vaccine administration. As will be readily appreciated, each of the modalities can be administered once, or repeatedly as desired. For example, the DNA vaccine may be given once, while a subsequent bacterial and/or yeast vaccine may be administered twice, three times or more, before administration of a viral vaccine commences. Similarly, multiple bacterial or yeast vaccine compositions may be administered prior to a viral vaccine composition. In the same way, the DNA, bacterial, and/or yeast vaccine may be given once and the viral vaccine may be given multiple times. Therefore, it should be noted that in a prime/boost regimen, the prime vaccination may use a modality that is different from the boost vaccination (e.g., DNA, bacterial, or yeast vaccination as prime, viral vaccination as boost).

It should further be recognized that the administrations of the specific modalities will be spaced apart by several days to allow an immune response to develop. Most typically, the first administration will be spaced apart from the second administration by at least two days, more typically by at least four days, even more typically by at least one week, and most typically by two weeks or even longer. Moreover, it should be noted that the immune system of the patient may also be pre-conditioned using immune stimulatory cytokines (e.g., IL-2, IL-15, IL-21) or cytokine analogs (e.g., ALT-803), using checkpoint inhibitors or Treg or M2 macrophage inhibitors to reduce immune suppression, or using cytokines that support an immune response and generation of immune memory (e.g., IL-12).

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment. As will also be appreciated, contemplated treatments may be repeated over time, particularly where new neoepitopes have developed (e.g., as a result of clonal expansion).

Moreover, it is noted that additional treatment regimens may be implemented to assist contemplated methods and compositions. Such additional treatment regimens will preferably be performed to increase 'visibility' of a tumor to the immune system. For example, to trigger overexpression or transcription of stress signals, it is contemplated that chemotherapy and/or radiation may be employed using at a low-dose regimen, preferably in a metronomic fashion. For example, it is generally preferred that such treatment will use doses effective to affect at least one of protein expression, cell division, and cell cycle, preferably to induce apoptosis or at least to induce or increase the expression of stress-related genes (and particularly NKG2D ligands). Thus, in further contemplated aspects, such treatment will include low dose treatment using one or more chemotherapeutic agents. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375.

With respect to the particular drug used in low-dose regimens, it is contemplated that all chemotherapeutic agents are deemed suitable. Among other suitable drugs, kinase inhibitors, receptor agonists and antagonists, anti-metabolic, cytostatic and cytotoxic drugs are all contemplated herein. However, particularly preferred agents include those identified to interfere or inhibit a component of a pathway that drives growth or development of the tumor.

Suitable drugs can be identified using pathway analysis on omics data as described in, for example, WO 2011/139345 and WO 2013/062505. Most notably, so achieved expression of stress-related genes in the tumor cells will result in surface presentation of NKG2D, NKP30, NKP44, and/or NKP46 ligands, which in turn activate NK cells to specifically destroy the tumor cells. Thus, it should be appreciated that low-dose chemotherapy may be employed as a trigger in tumor cells to express and display stress related proteins, which in turn will trigger NK-cell activation and/or NK-cell mediated tumor cell killing. Additionally, NK-cell mediated killing will be associated with release of intracellular tumor specific antigens, which is thought to further enhance the immune response.

EXAMPLES

Exemplary Sequence Arrangements

Neoepitope sequences were determined in silico by location-guided synchronous alignment of tumor and normal samples as, for example, disclosed in US 2012/0059670 and US 2012/0066001 using BAM files and BAM servers. Specifically, DNA analysis of the tumor was from the B16-F10 mouse melanoma line and matched normal was blood from C57bl/6 parental mouse DNA. The results were filtered for expression by RNA sequencing of this tumor cell line. Neoepitopes that were found expressed were further analyzed for binding affinity towards murine MHC-I (here: Kb) and MHC-II (here: I-Ab). Selected binders (with affinity of equal or less than 200 nM) were further analyzed after a further step of dbSNP filtering using positional permutations of all neoepitopes that were then processed through a weight matrix and neural network prediction to generate a score representing the likelihood of presence and/or strength of hydrophobic sequences or signal peptides. The best scoring arrangement (lowest likelihood of hydrophobic sequences or signal peptides) for the polytope (not shown) was used for further experiments. Neoepitopes were prioritized by detection in RNAseq or other quantitative system that yielded expression strength for a specific gene harboring the neoepitope mutation.

Table 1 shows exemplary neoepitopes that were expressed as determined by RNAseq along with gene name and mutated amino acid and position of the mutated amino acid. The neoepitope listed with * was discarded after dbSNP filtering as that neoepitope occurred as variant Rs71257443 in 28% of the population.

TABLE 1

| Gene | Position | Neoepitope-a | Neoepitope-b |
|---|---|---|---|
| VIPR2 | V73M | GETVTMPCP | |
| LILRB3 | T187N | VGPVNPSHR* | |
| FCRL1 | R286C | GLGAQCSEA | |
| FAT4 | S1613L | RKLTTELTI | PERRKLTTE |
| PIEZO2 | T2356M | MDWVWMDTT | VWMDTTLSL |
| SIGLEC14 | A292T | GKTLNPSQT | REGKTLNPS |
| SIGLEC1 | D1143N | VRNATSYRC | NVTVRNATS |
| SLC4A11 | Q678P | FAMAQIPSL | AQIPSLSLR |

Table 2 shows further examples of neoepitopes in which the position of the mutated amino acid was changed, and shows further alternate sequences for MHC-I presentation (9-mer) and MHC-II presentation (15-mer). The neoepitope sequence for MHC-II presentation was back-translated to the corresponding nucleic acid sequence, which is also shown in Table 2.

TABLE 2

| Gene | Change | Neoepitope-a | Neoepitope-b | Extended 15 mer | Nucleotide Sequence |
|---|---|---|---|---|---|
| SLC4A11 | Q678P | FAMAQIPSL | AQIPSLSLR | PFAMAQIPSLSLRAV | CCCTTCGCCATGGCC CAGATCCCCAGCCTG AGCCTGAGGGCCGTG |
| SIGLEC1 | D1143N | VRNATSYRC | NVTVRNATS | LPNVTVRNATSYRCG | CTGCCCAACGTGACC GTGAGGAACGCCACC AGCTACAGGTGCGGC |
| SIGLEC14 | A292T | GKTLNPSQT | REGKTLNPS | SWFREGKTLNPSQTS | AGCTGGTTCAGGGAG GGCAAGACCCTGAAC CCCAGCCAGACCAGC |
| PIEZO2 | T2356M | MDWVWMDTT | VWMDTTLSL | AVMDWVWMDTTLSLS | GCCGTGATGGACTGG GTGTGGATGGACACC ACCCTGAGCCTGAGC |
| FAT4 | S1613L | RKLTTELTI | PERRKLTTE | LGPERRKLTTELTII | CTGGGCCCCGAGAGG AGGAAGCTGACCACC GAGCTGACCATCATC |
| FCRL1 | R286C | GLGAQCSEA | | NNGLGAQCSEAVTLN | AACAACGGCCTGGGC GCCCAGTGCAGCGAG GCCGTGACCCTGAAC |
| VIPR2 | V73M | GETVTMPCP | | NVGETVTMPCPKVFS | AACGTGGGCGAGACC GTGACCATGCCCTGC CCCAAGGTGTTCAGC |
| FLRT2 | R346W | EQVWGMAVR | | CQGPEQVWGMAVREL | TGCCAGGGCCCCGAG CAGGTGTGGGGCATG GCCGTGAGGGAGCTG |

Sequence Trafficking

Model cancer: Murine B16-F10 melanoma (derived from C57/B16 mouse) was used tumors were screened in a tumor versus normal manner as described above, and expressed mutant epitopes were identified in the B16F10 melanoma cell line. Candidate neoepitopes were further filtered as described above using sequencing data analysis and binding analysis to murine MHC I (H2-Kb, H2-Dd) and MHC II (I-Ab). Nine distinct polytope constructs were then prepared for testing various trafficking schemes, and each construct was prepared as the corresponding recombinant nucleic acid under the control of a CMV promoter. Each construct was cloned into an AdV5 expression vector that had deleted E1 and E2b genes, and the resulting recombinant virus was then used for transfection of mice as is further discussed below.

More specifically, three polytope constructs included MHC I binding neoepitopes for MHC-I presentation and were therefore targeted to the cytoplasmic compartment. While one construct had an unmodified N-terminus, another construct had an N-terminal non-cleavable ubiquitin, and yet another construct had an N-terminal cleavable ubiquitin. Ubiquitination was used to target the proteasome in the cytosol. Three further polytope constructs included MHC I binding neoepitopes for MHC-II presentation and were therefore targeted to the lysosomal/endosomal compartments compartment. While one construct had lysosomal targeting sequence, another construct had a recycling endosomal targeting sequence, and yet another construct had a sorting endosomal targeting sequence. Three additional polytope constructs included MHC II binding neoepitopes for MHC-II presentation and were also targeted to the lysosomal/endosomal compartments compartment. Once more, one construct had lysosomal targeting sequence, another construct had a recycling endosomal targeting sequence, and yet another construct had a sorting endosomal targeting sequence. These nine constructs had sequence arrangements as follows.

In the following exemplary sequences, for MHC-I presentation, ubiquitin (cleavable and non-cleavable) were used for proteasome targeting, while the CD1b leader peptide was used as an export leader peptide for trafficking the polypeptide out of the cytosol for all MHC-II directed sequences. LAMP1-TM/cytoplasmic tail was used as a lysosomal targeting sequence, while LAMP1-TM/CD1a tail was used as a recycling endosomes targeting sequence, and LAMP1-TM/CD1c tail was used as a sorting endosomes targeting domain.

It should further be noted that various internal controls were also used in the above polypeptides to account for expression and presentation. More specifically, the SIINFEKL peptide was used as an internal control for a MHC I restricted (Kb) peptide epitope, while the Esat6 peptide was used as an internal control for a secreted protein for MHC II presentation. FLAG-tag was used as an internal control epitope for detection of expression, and cMYC used as an internal control Tag for simple protein detection.

Exemplary Constructs for MHC-I Epitopes Directed to MHC-I Presentation (Traffic Through Proteasome, Cytoplasmic Targeting)

Polyepitope only: 12aa-A$'''$-12aa-AAAA-12aa-B$'''$-12aa-AAAA-(12aa-X$'''$-12aa-AAAA)$_n$-SIINFEKL-AAAA-Esat6-cMYC. FIG. 5A exemplarily depicts the polypeptide structure of such arrangement where the SIINFEKL motif is underlined, the Esat6 motif is in italics, and where the cMY motif is in bold type font. The nucleotide sequence for FIG. 5A is SEQ ID NO: 1, and the polypeptide sequence for FIG. 5A is SEQ ID NO: 4.

Polyepitope and cleavable ubiquitin GGR N-terminus: Ubiquitin-GGR-12aa-A$'''$-12aa-AAAA-12aa-B$'''$-12aa-AAAA-(12aa-X$'''$-12aa-AAAA)$_n$-SIINFEKL-AAAA-Esat6-cMYC. FIG. 5B exemplarily depicts the polypeptide structure of such arrangement where the cleavable ubiquitin moiety is italics and underlined, the SIINFEKL motif is underlined, the Esat6 motif is in italics, and where the cMY motif is in bold type font. The nucleotide sequence for FIG. 5B is SEQ ID NO: 2, and the polypeptide sequence for FIG. 5B is SEQ ID NO: 5.

Polyepitope and non-cleavable ubiquitin G N-terminus: Ubiquitin-G-12aa-A$'''$-12aa-AAAA-12aa-B$'''$-12aa-AAAA-(12aa-X$'''$-12aa-AAAA)$_n$-SIINFEKL-AAAA-Esat6-cMYC. FIG. 5C exemplarily depicts the polypeptide structure of such arrangement where the cleavable ubiquitin moiety is italics and underlined, the SIINFEKL motif is underlined, the Esat6 motif is in italics, and where the cMY motif is in bold type font. The nucleotide sequence for FIG. 5C is SEQ ID NO: 3, and the polypeptide sequence for FIG. 5C is SEQ ID NO: 6.

Exemplary Constructs for MHC-I Epitopes Directed to MHC-II Presentation (Export from Cytoplasm, Traffic Through Endo/Lysosome)

Lysosomal targeting of Kb epitope peptides: (CD1b leader peptide)-20aa-A$'''$-20aa-GPGPG-20aa B$'''$-20aa-GPGPG-(20aa-X$'''$-20aa-GPGPG-)$_n$-Esat6-FlagTag-LAMP1TM/cytoplasmic tail. FIG. 6A exemplarily depicts the polypeptide structure of such arrangement where the CD1b leader peptide moiety is bold, the Esat6 motif is in underlined, the Flag-tag motif is italics, and where the LAMP1TM/cytoplasmic tail is in bold/underline type font. The nucleotide sequence for FIG. 6A is SEQ ID NO: 7, and the polypeptide sequence for FIG. 6A is SEQ ID NO: 10.

Recycling lysosome targeting of Kb epitope peptides: (CD1b leader peptide)-20aa-A$'''$-20aa-GPGPG-20aa B$'''$-20aa-GPGPG-(20aa-X$'''$-20aa-GPGPG-)$_n$-Esat6-FlagTag-LAMP1TM/CD1a tail. FIG. 6B exemplarily depicts the polypeptide structure of such arrangement where the CD1b leader peptide moiety is bold, the Esat6 motif is in underlined, the Flag-tag motif is italics, and where the LAMP1TM motif is in bold/underline type font, and the CD1a targeting motif is underline/italics. The nucleotide sequence for FIG. 6B is SEQ ID NO: 8, and the polypeptide sequence for FIG. 6B is SEQ ID NO: 11.

Sorting endosome targeting of Kb epitope peptides: (CD1b leader peptide)-20aa-A$'''$-20aa-GPGPG-20aa B$'''$-20aa-GPGPG-(20aa-X$'''$-20aa-GPGPG-)$_n$-Esat6-FlagTag-LAMP1TM/CD1c tail. FIG. 6C exemplarily depicts the polypeptide structure of such arrangement where the CD1b leader peptide moiety is bold, the Esat6 motif is in underlined, the Flag-tag motif is italics, and where the LAMP1TM motif is in bold/underline type font, and the CD1c targeting motif is underline/italics. The nucleotide sequence for FIG. 6C is SEQ ID NO: 9, and the polypeptide sequence for FIG. 6C is SEQ ID NO: 12.

Exemplary Constructs for MHC-II Epitopes Directed to MHC-II Presentation (Export from Cytoplasm, Traffic Through Endo/Lysosome)

Lysosomal targeting of IAb epitope peptides: (CD1b leader peptide)-20aa-A$'''$-20aa-GPGPG-20aa B$'''$-20aa- GPGPG-(20aa-X'''-20aa-GPGPG-)$_n$-Esat6-FlagTag-LAMP1TM/cytoplasmic tail. FIG. 7A exemplarily depicts the polypeptide structure of such arrangement where the CD1b leader peptide moiety is bold, the SIINFEKL and Esat6 motifs are underlined, the Flag-tag motif is italics, and where the LAMP1TM/cytoplasmic tail is in bold/underline type font. The nucleotide sequence for FIG. 7A is SEQ ID NO: 13, and the polypeptide sequence for FIG. 7A is SEQ ID NO: 16.

Recycling lysosome targeting of IAb epitope peptides: (CD1b leader peptide)-20aa-A'''-20aa-GPGPG-20aa B'''-20aa-GPGPG-(20aa-X'''-20aa-GPGPG-)$_n$-Esat6-FlagTag-LAMP1TM/CD1a tail. FIG. 7B exemplarily depicts the polypeptide structure of such arrangement where the CD1b leader peptide moiety is bold, the SIINFEKL and Esat6 motifs are underlined, the Flag-tag motif is italics, where the LAMP1TM motif is in bold/underline type font, and where the CD1a tail is in bold/italics. The nucleotide sequence for FIG. 7B is SEQ ID NO: 14, and the polypeptide sequence for FIG. 7B is SEQ ID NO: 17.

Sorting endosome targeting of IAb epitope peptides: (CD1b leader peptide)-20aa-A'''-20aa-GPGPG-20aa B'''-20aa-GPGPG-(20aa-X'''-20aa-GPGPG-)$_n$-Esat6-FlagTag-LAMP1TM/CD1c tail. FIG. 7C exemplarily depicts the polypeptide structure of such arrangement where the CD1b leader peptide moiety is bold, the SIINFEKL and Esat6 motifs are underlined, the Flag-tag motif is italics, where the LAMP1TM motif is in bold/underline type font, and where the CD1c tail is in bold/italics. The nucleotide sequence for FIG. 7C is SEQ ID NO: 15, and the polypeptide sequence for FIG. 7C is SEQ ID NO: 18.

In Vivo Vaccination

Figure 9A:
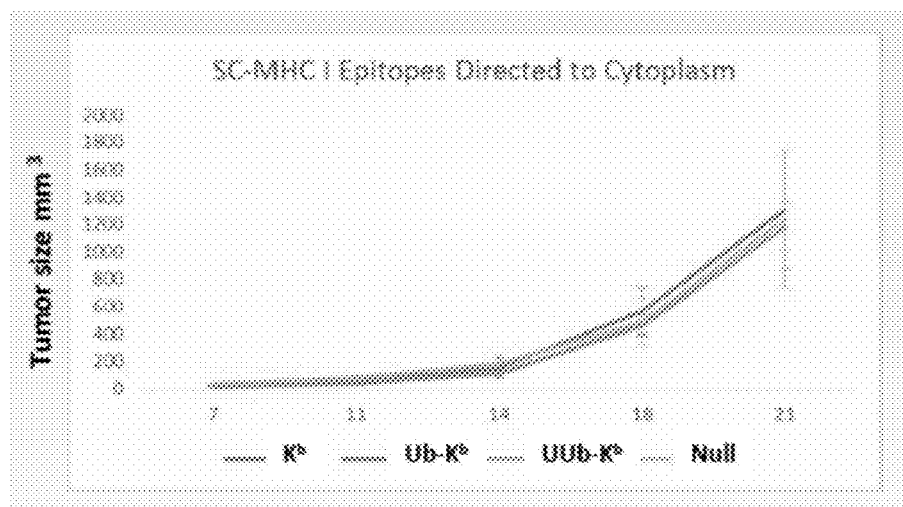
FIGS. 9A-9C are graphs depicting exemplary results for the anti-tumor vaccination using subcutaneous injection of the vaccine.
Figure 9B:
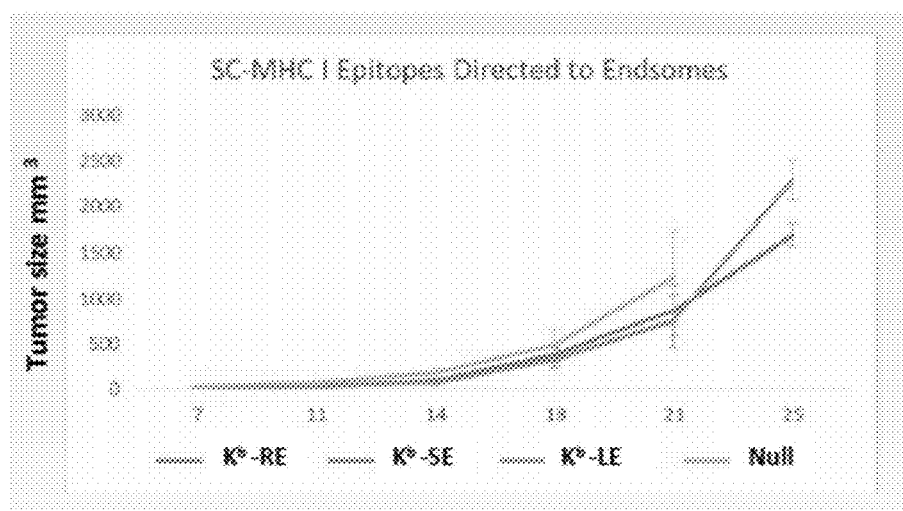
Figure 9C:
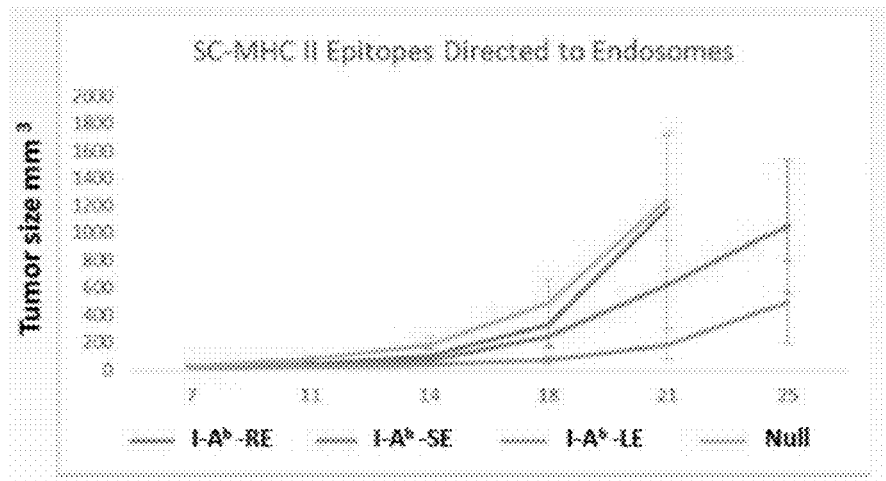

FIG. 8 depicts an exemplary in vivo vaccination experiment where nine groups of C57bl/6 mice were immunized with nine distinct recombinant Ad5 viruses comprising the sequence arrangements substantially as described above. Immunization followed a biweekly schedule of administration with distinct routes for separate groups of animals (subcutaneous and intravenous) as is schematically shown in FIG. 8. Tumor challenge with B16-F10 melanoma cells was at day 42, followed by administration of an M2 macrophage suppressive drug (RP 182) and IL-15 superagonist (Alt-803). FIGS. 9A-9C depict exemplary results for subcutaneous administration, while FIGS. 10A-10C depict exemplary results for intravenous administration.

Notably, subcutaneous injection of adenovirus encoding Class I polytopes directed to the cytoplasm and MHC-I presentation did not provide a significant immune protection, regardless of the presence or absence of ubiquitination as can be taken from FIG. 9A. On the other hand, where the Class I polytopes were directed to the endosomal and lysosomal compartments for processing and presentation via MHC-II, some protective immunity was observed for direction to the recycling endosomal compartment and lysosomal compartment as is evident from FIG. 9B. Even stronger immune protection was observed when Class II polytopes were directed to the endosomal and lysosomal compartments for processing and presentation via MHC-II. Here, the strongest protection was observed for lysosomal and sorting endosomal compartments as is shown in FIG. 9C.

Figure 10A:
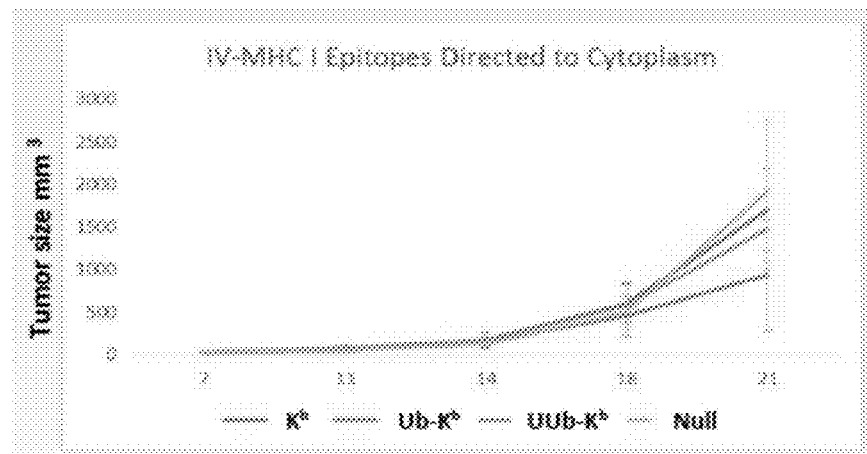
FIGS. 10A-10C are graphs depicting exemplary results for the anti-tumor vaccination using intravenous injection of the vaccine.
Figure 10B:
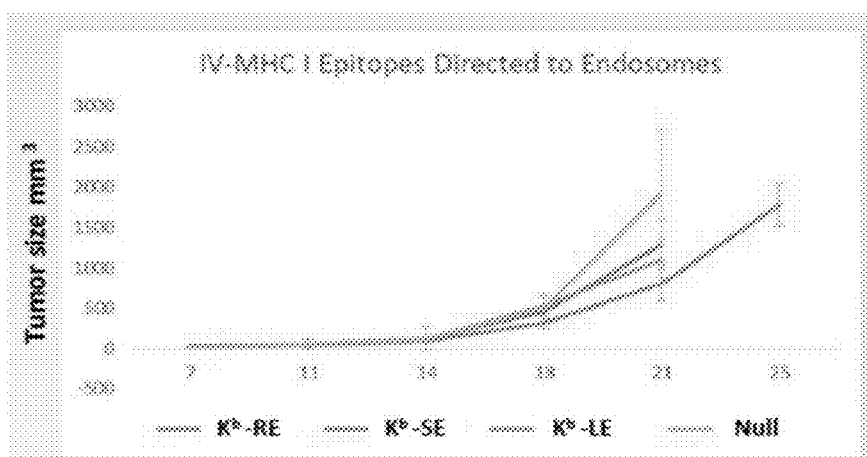
Figure 10C:
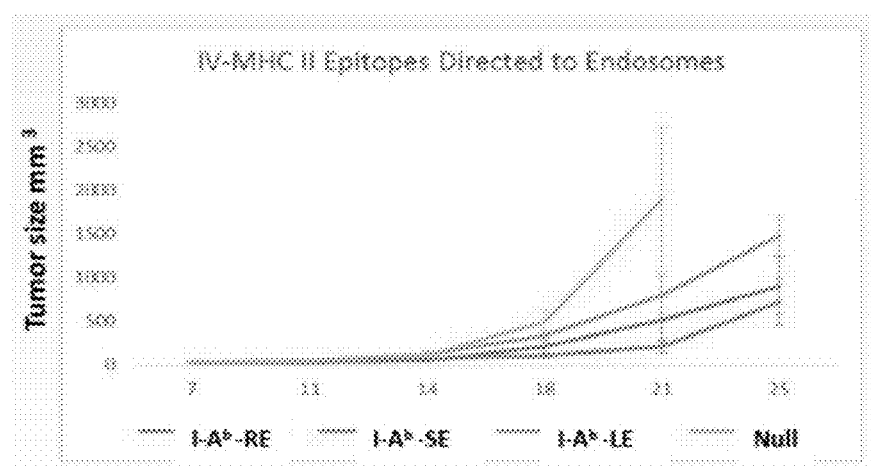

When immunization was performed with the same viral constructs, albeit via intravenous injection, protective effect of neoepitope vaccination was observed for Class I neoepitopes directed to the cytoplasm where the polytope included cleavable ubiquitin, and some protective effect was observed where the polytope included non-cleavable ubiquitin as can be seen from FIG. 10A. Notably, when the Class I polytopes were directed to the endosomal and lysosomal compartment, stronger protective effect was observed in all vaccinations as is shown in FIG. 10B. Moreover, strong protective effect was observed when Class II polytopes were directed to the endosomal and lysosomal compartments for processing and presentation via MHC-II. Here, the strongest protection was observed for recycling and sorting endosomal compartments as is shown in the graph of FIG. 10C.

Comparison of Routes and Vectors

Figure 11A:
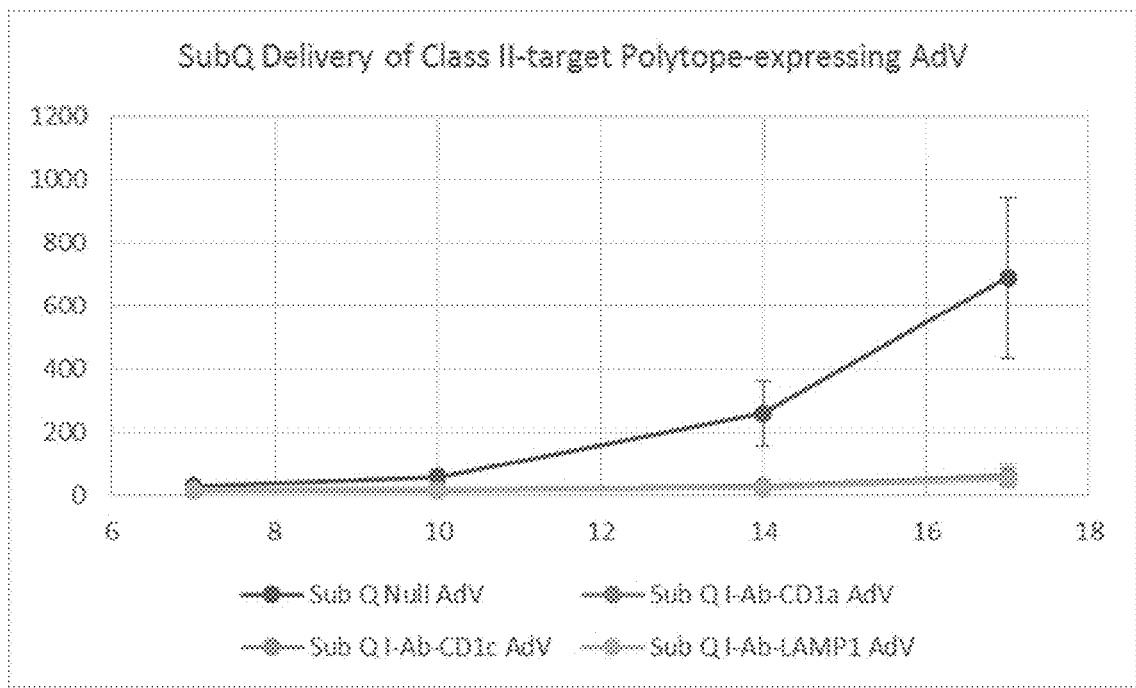
FIGS. 11A-11E are graphs depicting exemplary results for selected DNA and viral vaccine compositions and selected routes of administration.
Figure 11B:
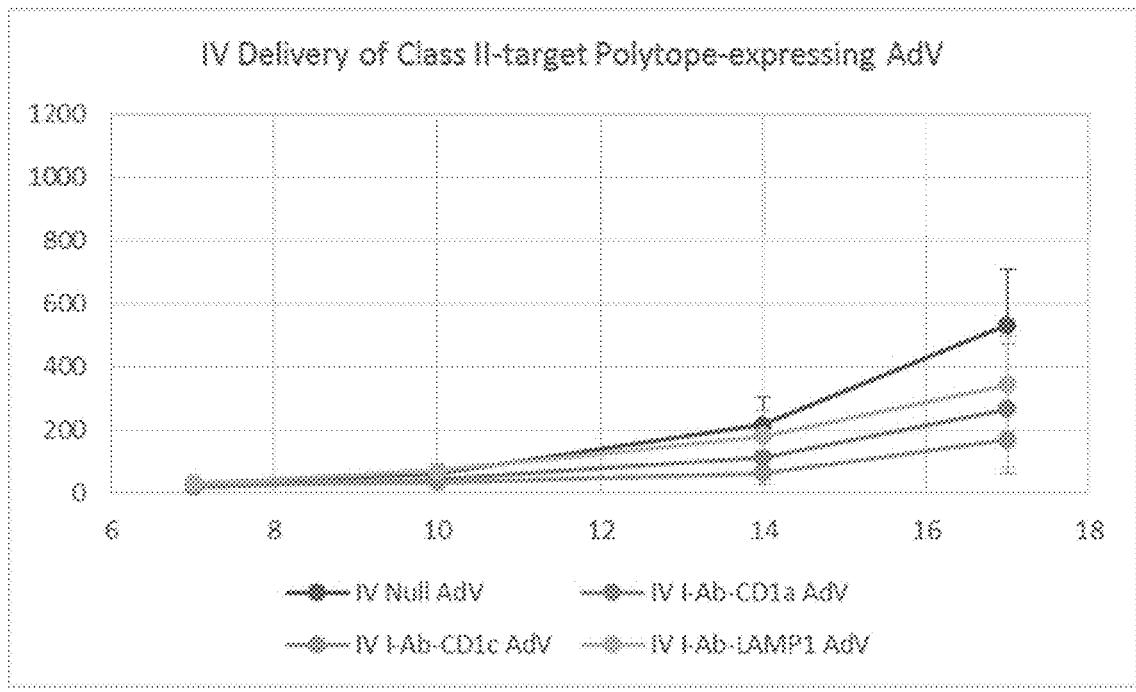

In still further experiments, the inventors further investigated if the actual route of administration and type of expression vector had an effect on the therapeutic efficacy. To that end, a substantially identical mouse model as described above was employed and the polytope was constructed from neoepitopes from B16F10 melanoma cells. FIGS. 11A and 11B show exemplary results for the experiments where the expression vector was an adenovirus. As can be readily seen, subcutaneous administration of an adenoviral expression system encoding MHC II targeted polytope conferred a significant immune protective effect for all sub-cellular locations while a null vector failed to provide immune protective effect as can be taken from FIG. 11A. Notably, when the same vector constructs were tested using intravenous administration, immune protective effect was less pronounced as can be taken from FIG. 11B.

Figure 11C:
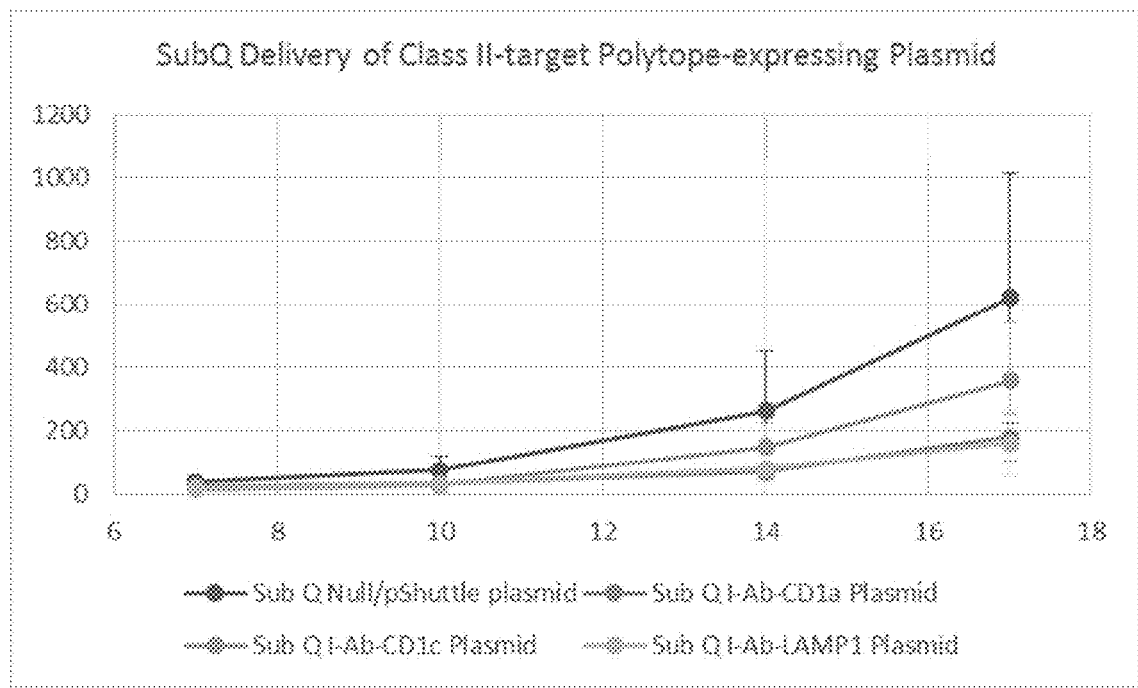
Figure 11D:
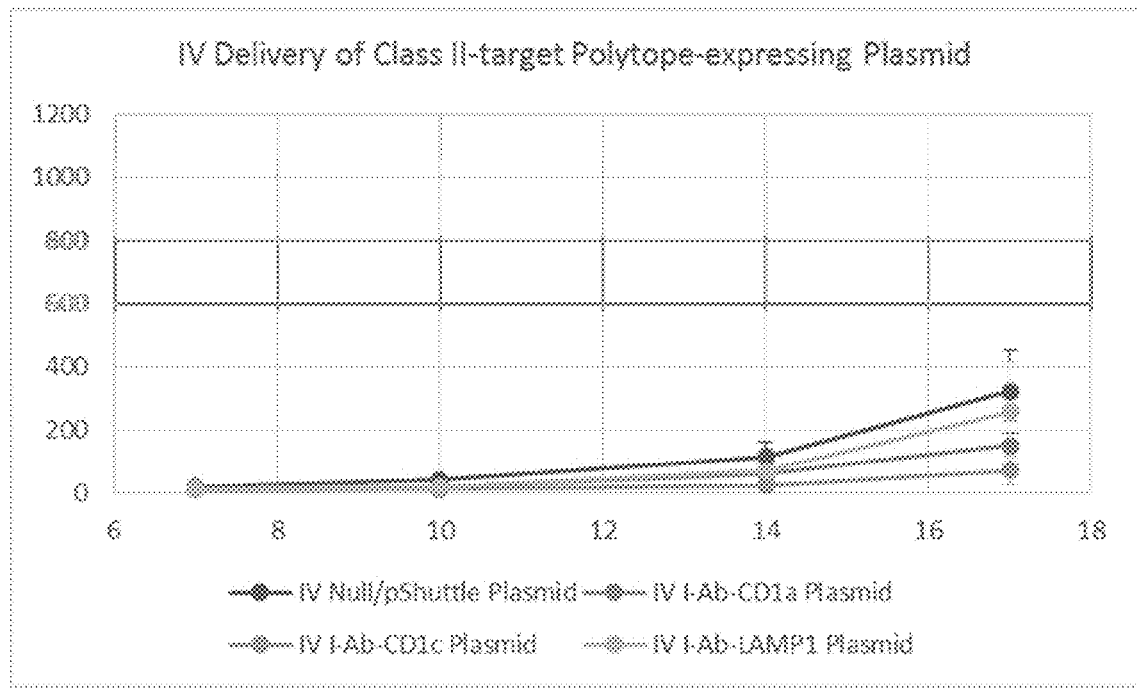

Conversely, where the expression vector was a plasmid (here: shuttle vector for generating the adenoviral expression vector) targeting MHC II presentation as above, subcutaneous administration of the plasmid conferred a notable immune protective effect versus null vector as is shown in FIG. 11C. Moreover, and unexpectedly, where the same plasmid was administered by intravenous injection, a substantial immune protective effect was observed, even for the null vector as can be taken from FIG. 11D. While not wishing to be bound by any particular theory or hypothesis, the inventors therefore contemplate that the immune protective effect may be at least in part due to an innate and an adaptive immune response.

Figure 11E:
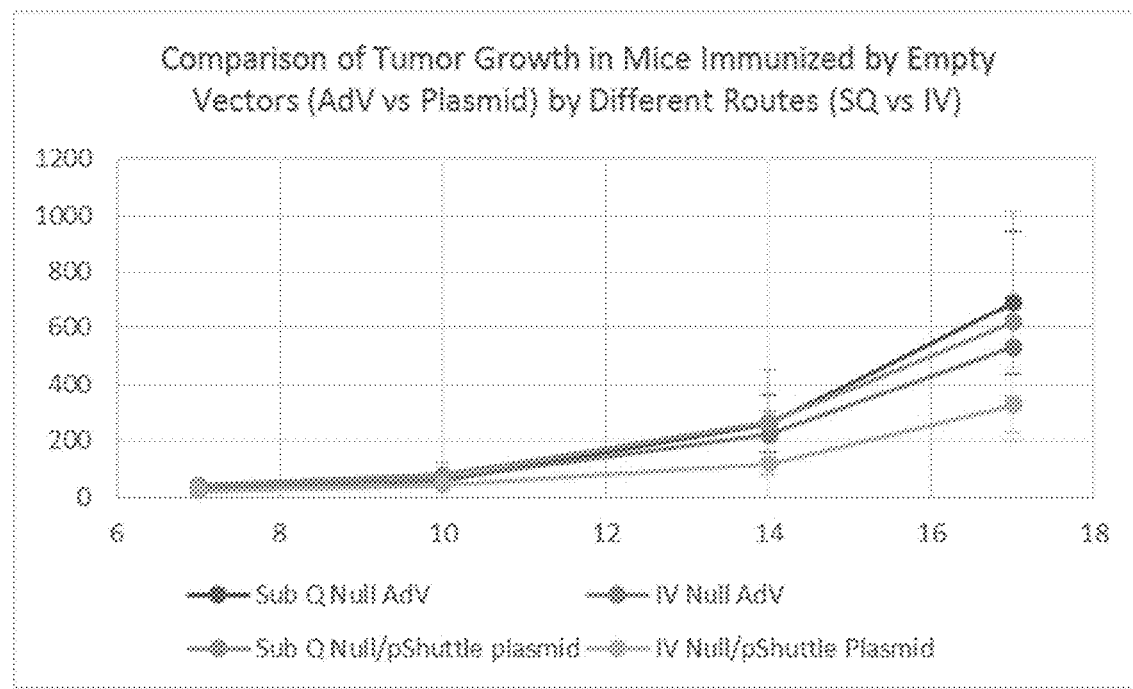

FIG. 11E illustrates a comparison between use of different routes using empty plasmid ('null') versus empty viral ('null') expression vector. As can be readily seen from the results, subcutaneous administration did not confer immune protective effect, while the strongest immune protective effect was observed by intravenous administration of null plasmid.

Figure 12:
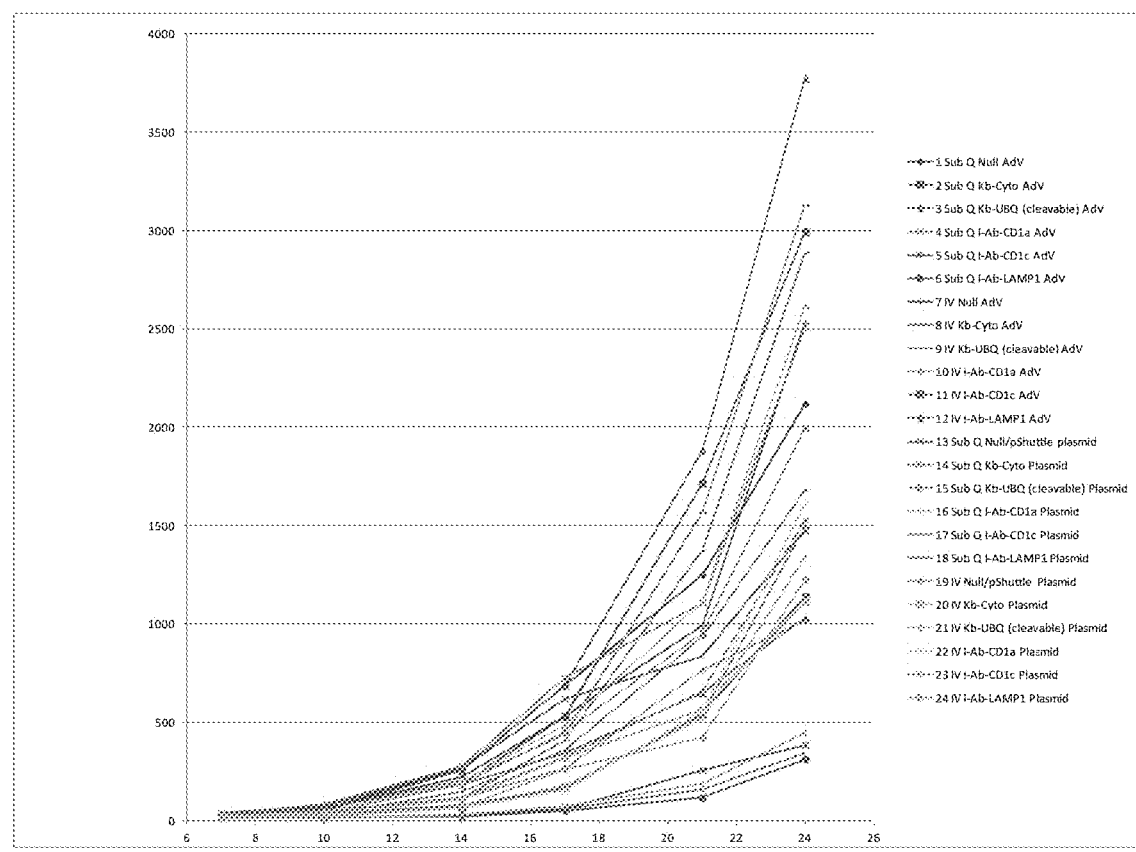
FIG. 12 is a graph depicting exemplary results for the anti-tumor effect using DNA and viral vaccines with various compositions and routes.

FIG. 12 depicts the data shown in Table 3 below where the type of expression vector is shown as "Type", and the route of administration indicated as "Route". The particular MHC targeting and targeting of sub-cellular location is shown under "Nucleic Acid", while tumor volume is indicated for the dates measured after implantation of B16-F10 melanoma cells.

TABLE 3

| # | Type | Route | Nucleic Acid | Day 7 | Day 10 | Day 14 | Day 17 | Day 21 | Day 24 |
|---|------|-------|--------------|-------|--------|--------|--------|--------|--------|
| 1 | AdV | Sub Q | Null AdV | 29.49791667 | 57.92242 | 260.014833 | 688.7629 | 1246.774 | 2119.323 |
| 2 | AdV | Sub Q | $K^b$-Cyto AdV | 23.97941667 | 39.50383 | 187.24075 | 529.0868 | 1715.039 | 2993.372 |

TABLE 3-continued

| # | Type | Route | Nucleic Acid | Day 7 | Day 10 | Day 14 | Day 17 | Day 21 | Day 24 |
|---|---|---|---|---|---|---|---|---|---|
| 3 | AdV | Sub Q | $K^b$-UBQ (cleavable) AdV | 26.4185 | 50.95125 | 253.255 | 685.7033 | 1882.06 | 3773.93 |
| 4 | AdV | Sub Q | I-$A^b$-CD1a AdV | 16.135 | 16.195 | 26.6793333 | 60.27433 | 157.3007 | 341.9303 |
| 5 | AdV | Sub Q | I-$A^b$-CD1c AdV | 15.75 | 17.37667 | 29.32725 | 59.65917 | 257.8108 | 385.198 |
| 6 | AdV | Sub Q | I-$A^b$-LAMP1 AdV | 17.64666667 | 18.82333 | 21.9275 | 50.01192 | 116.2528 | 310.7113 |
| 7 | AdV | IV | Null AdV | 29.06025 | 60.5985 | 219.399833 | 531.3525 | 990.4138 | 2527.871 |
| 8 | AdV | IV | $K^b$-Cyto AdV | 36.07041667 | 48.72017 | 113.244 | 408.8533 | 1372.974 | 2887.699 |
| 9 | AdV | IV | $K^b$-UBQ (cleavable) AdV | 26.62333333 | 65.407 | 202.246667 | 438.495 | 1565.227 | 3128.09 |
| 10 | AdV | IV | I-$A^b$-CD1a AdV | 22.08333333 | 44.61333 | 114.910333 | 267.6967 | 767.7163 | 1018.658 |
| 11 | AdV | IV | I-$A^b$-CD1c AdV | 28.1535 | 34.5925 | 62.64375 | 169.7857 | 542.2878 | 1140.391 |
| 12 | AdV | IV | I-$A^b$-LAMP1 AdV | 29.82733333 | 70.32883 | 183.320333 | 344.7302 | 648.9571 | 1033.862 |
| 13 | Plasmid | Sub Q | Null/pShuttle plasmid | 38.22775 | 76.19925 | 263.548875 | 620.3451 | 837.5773 | 1473.021 |
| 14 | Plasmid | Sub Q | $K^b$-Cyto Plasmid | 31.7225 | 81.33738 | 277.45375 | 724.6457 | 1107.705 | 2506.988 |
| 15 | Plasmid | Sub Q | $K^b$-UBQ (cleavable) Plasmid | 19.42 | 40.41075 | 181.246 | 454.0527 | 951.4715 | 1995.16 |
| 16 | Plasmid | Sub Q | I-$A^b$-CD1a Plasmid | 25.595 | 32.52 | 70.540625 | 179.315 | 522.0373 | 1340.285 |
| 17 | Plasmid | Sub Q | I-$A^b$-CD1c Plasmid | 15.19 | 28.58125 | 149.4485 | 358.5129 | 933.2926 | 1681.392 |
| 18 | Plasmid | Sub Q | I-$A^b$-LAMP1 Plasmid | 19.6025 | 32.69625 | 80.381875 | 160.4238 | 542.5311 | 1493.744 |
| 19 | Plasmid | IV | Null/pShuttle Plasmid | 21.3825 | 42.272 | 116.60725 | 324.2005 | 659.2577 | 1528.49 |
| 20 | Plasmid | IV | $K^b$-Cyto Plasmid | 14.155 | 30.05125 | 106.206 | 319.6288 | 562.9468 | 1113.58 |
| 21 | Plasmid | IV | $K^b$-UBQ (cleavable) Plasmid | 20.4275 | 45.167 | 198.383625 | 486.2856 | 1111.359 | 2619.425 |
| 22 | Plasmid | IV | I-$A^b$-CD1a Plasmid | 16.45 | 22.293 | 61.65325 | 151.3369 | 554.821 | 1612.671 |
| 23 | Plasmid | IV | I-$A^b$-CD1c Plasmid | 11.725 | 13.7225 | 27.265125 | 73.65725 | 184.9038 | 447.9333 |
| 24 | Plasmid | IV | I-$A^b$-LAMP1 Plasmid | 15.6875 | 19.625 | 70.805875 | 259.7303 | 422.639 | 1223.331 |

As can be readily seen from the data presented here, targeting MHC-II matched neoepitopes of a polytope and targeting the polytope towards MHC-II presentation via CD1c, LAMP1, and CD1a was significantly effective when administered intravenously in plasmid form, and subcutaneously in adenovirus form. Notably, and as also reflected in the data, targeting MHC-I was significantly less effective to provide immune protection.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of stimulating an immune response in a patient, the method comprising:
   a) generating a recombinant nucleic acid having a sequence that encodes a polytope, wherein the polytope comprises a plurality of filtered neoepitope sequences, wherein the neoepitope sequences are filtered in silico by comparing tumor versus matched normal control of the same patient; wherein the neoepitope sequences are filtered in silico to have binding affinity to MHC-II of equal or less than 200 nM; wherein the recombinant nucleic acid further comprises a trafficking element that directs the polytope to a sub-cellular location selected from the group consisting of a recycling endosome, a sorting endosome, and a lysosome;
   b) cloning the recombinant nucleic acid into an adenoviral vector;
   c) formulating the recombinant adenovirus into an immune therapy composition; and
   d) administering the immune therapy composition to the patient by subcutaneous injection.

2. The method of claim 1 wherein the trafficking element is selected from the group consisting of a CD1b leader sequence, a CD1a tail, a CD1c tail, and a LAMP1-transmembrane sequence.

3. The method of claim 1 wherein the recombinant nucleic acid further comprises an additional sequence that encodes a second polytope, wherein the second polytope comprises a second trafficking element that directs the second polytope to a different sub-cellular location than the first polytope and wherein the second polytope comprises a second plurality of filtered neoepitope sequences.

4. The method of claim 3 wherein at least one of the filtered neoepitope sequences and at least one of the second filtered neoepitope sequences are identical.

5. The method of claim 1 wherein the recombinant nucleic acid further comprises a sequence that encodes at least one of a co-stimulatory molecule, an immune stimulatory cytokine, and a protein that interferes with or down-regulates checkpoint inhibition.

6. The method of claim 5 wherein the co-stimulatory molecule is selected from the group consisting of CD80, CD86, CD30, CD40, CD30L, CD40L, ICOS-L, B7-H3, B7-H4, CD70, OX40L, 4-IBBL, GITR-L, TIM-3, TIM-4, CD48, CD58, TLIA, ICAM-I, and LFA3.

7. The method of claim 5 wherein the immune stimulatory cytokine is selected from the group consisting of IL-2, IL-12, IL-15, IL-15 super agonist (ALT803), IL-21, IPS1, and LMP1.

8. The method of claim 5 wherein the protein that interferes is an antibody or an antagonist of CTLA-4, PD-1, TIM1 receptor, 2B4, or CD160.

9. The method of claim 1 wherein the recombinant adenovirus, optionally has at least one of an E1 and an E2b gene deleted.

10. The method of claim 1 further comprising generating a second recombinant nucleic acid having the sequence that encodes the polytope, wherein the second recombinant nucleic acid comprises a promoter operably linked to the sequence that encodes the polytope to drive expression of the polytope in a non-mammalian cell.

* * * * *